(12) United States Patent
Shigematsu et al.

(10) Patent No.: US 7,667,050 B2
(45) Date of Patent: Feb. 23, 2010

(54) SALT SUITABLE FOR AN ACID GENERATOR AND A CHEMICALLY AMPLIFIED POSITIVE RESIST COMPOSITION CONTAINING THE SAME

(75) Inventors: Junji Shigematsu, Osaka (JP); Isao Yoshida, Ikeda (JP); Yukako Harada, Settsu (JP); Masumi Suetsugu, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 201 days.

(21) Appl. No.: 11/889,596

(22) Filed: Aug. 15, 2007

(65) Prior Publication Data

US 2008/0086014 A1    Apr. 10, 2008

(30) Foreign Application Priority Data

Aug. 22, 2006   (JP) .............................. 2006-225059

(51) Int. Cl.
*C07C 309/19*   (2006.01)
*C07D 333/46*   (2006.01)
(52) U.S. Cl. ........................................ 549/78; 560/150
(58) Field of Classification Search ........................ None
See application file for complete search history.

(56) References Cited

U.S. PATENT DOCUMENTS

| | | | |
|---|---|---|---|
| 6,348,297 B1 | 2/2002 | Uetani et al. |
| 6,383,713 B1 | 5/2002 | Uetani et al. |
| 6,548,220 B2 | 4/2003 | Uetani et al. |
| 6,548,221 B2 | 4/2003 | Uetani et al. |
| 6,824,957 B2 | 11/2004 | Okino et al. |
| 6,893,792 B2 | 5/2005 | Miya et al. |
| 6,908,722 B2 | 6/2005 | Ebata et al. |
| 7,262,321 B2 | 8/2007 | Harada et al. |
| 7,301,047 B2 | 11/2007 | Yoshida et al. |
| 7,304,175 B2 | 12/2007 | Harada et al. |
| 2003/0194639 A1 | 10/2003 | Miya et al. |
| 2006/0019042 A1 | 1/2006 | Nojima et al. |
| 2006/0194982 A1 | 8/2006 | Harada et al. |
| 2007/0078269 A1 | 4/2007 | Harada et al. |
| 2007/0100096 A1 | 5/2007 | Harada et al. |
| 2007/0100158 A1 | 5/2007 | Harada et al. |
| 2007/0100159 A1 | 5/2007 | Yoshida et al. |
| 2007/0122750 A1 | 5/2007 | Yamaguchi et al. |
| 2007/0148702 A1 | 6/2007 | Nakamura et al. |
| 2007/0184382 A1 | 8/2007 | Yamaguchi et al. |
| 2008/0193874 A1 | 8/2008 | Takata et al. |

FOREIGN PATENT DOCUMENTS

| | | |
|---|---|---|
| EP | 1041442 A1 | 10/2000 |
| EP | 1077391 A1 | 2/2001 |
| EP | 1167349 A1 | 1/2002 |
| GB | 2441032 A | 2/2008 |
| JP | 2002-202607 A | 7/2002 |
| JP | 2002-265436 A | 9/2002 |
| JP | 2003-122012 A | 4/2003 |
| JP | 2003-131383 A | 5/2003 |
| JP | 2004-4561 A | 1/2004 |
| JP | 2004-117959 A | 4/2004 |
| JP | 2006-306856 A | 11/2006 |

*Primary Examiner*—Fiona T Powers
(74) *Attorney, Agent, or Firm*—Birch, Stewart, Kolasch & Birch, LLP

(57) ABSTRACT

The present invention provides a salt represented by the formula (I):

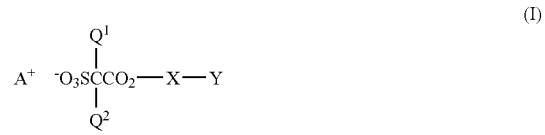

wherein

X represents a C3-C30 divalent group containing at least one divalent alicyclic hydrocarbon group, and at least one —$CH_2$— in the C3-C30 divalent group may be substituted with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be substituted with —O— or —CO—, $Q^1$ and $Q^2$ each independently represent a fluorine atom or a C1-C6 perfluoroalkyl group, and $A^+$ represents an organic counter ion.

26 Claims, No Drawings

SALT SUITABLE FOR AN ACID GENERATOR AND A CHEMICALLY AMPLIFIED POSITIVE RESIST COMPOSITION CONTAINING THE SAME

This nonprovisional application claims priority under 35 U.S.C. § 119(a) on Patent Application No. 2006-225059 filed in JAPAN on Aug. 22, 2006, the entire contents of which are hereby incorporated by reference.

FIELD OF THE INVENTION

The present invention relates to a salt suitable for an acid generator used for a chemically amplified resist composition which is used in fine processing of semiconductors, and a chemically amplified positive resist composition containing the same.

BACKGROUND OF THE INVENTION

A chemically amplified positive resist composition used for semiconductor microfabrication employing a lithography process contains an acid generator comprising a compound generating an acid by irradiation.

In semiconductor microfabrication, it is desirable to form patterns having high resolution, and it is expected for a chemically amplified resist composition to give such patterns.

US 2003/0194639 A1 also discloses a chemically amplified resist composition containing the salt represented by the following formulae:

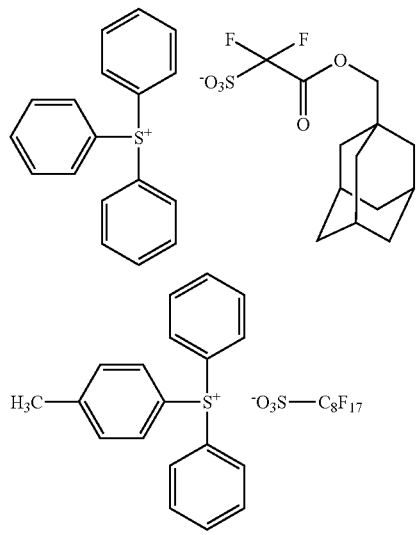

or the like as the acid generator.

SUMMARY OF THE INVENTION

An object of the present invention is to provide a salt suitable for an acid generator capable of providing chemically amplified resist compositions giving patterns having higher resolution.

Other objects of the present invention are to provide a synthetic intermediate for the salt and to provide a process for producing the synthetic intermediate or the salt.

Still another object of the present invention is to provide a chemically amplified resist composition containing the salt.

These and other objects of the present invention will be apparent from the following description.

The present invention relates to the followings:

<1> A salt represented by the formula (I):

wherein

X represents a C3-C30 divalent group containing at least one divalent alicyclic hydrocarbon group, and at least one —$CH_2$— in the C3-C30 divalent group may be substituted with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be substituted with —O— or —CO—, $Q^1$ and $Q^2$ each independently represent a fluorine atom or a C1-C6 perfluoroalkyl group, and $A^+$ represents an organic counter ion;

<2> The salt according to <1>, wherein $Q^1$ and $Q^2$ each independently represent a fluorine atom or a trifluoromethyl group;

<3> The salt according to <1> or <2>, wherein the organic counter ion is at least one cation selected from a cation represented by the formula (IIa):

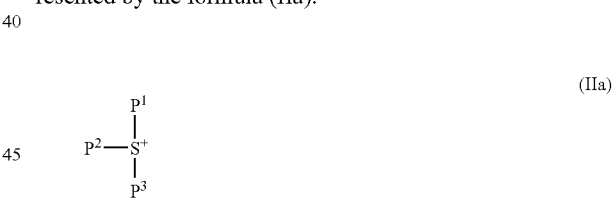

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

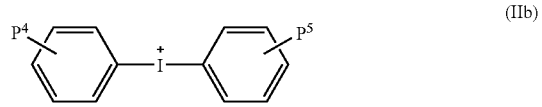

wherein $P^4$ and $P^5$ each independently represent a hydrogen atom, a hydroxyl group, a C1-C12 alkyl group or a C1-C12 alkoxy group, a cation represented by the formula (IIc):

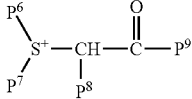

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxocycloalkyl group together with the adjacent —CHCO—, and at least one —$CH_2$— in the divalent acyclic hydrocarbon group may be replaced with —CO—, —O— or —S—, and a cation represented by the formula (IId):

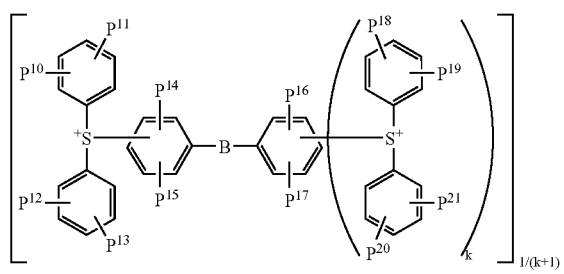

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1;

<4> The salt according to <1> or <2>, wherein the organic counter ion is a cation represented by the formula (IIIa), (IIIb) or (IIIc):

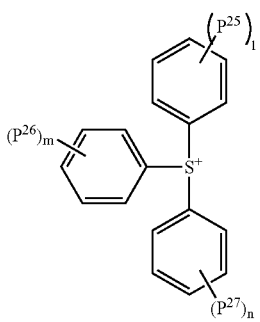

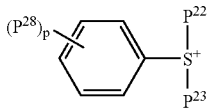

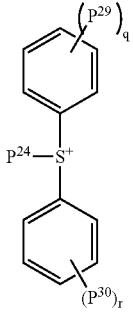

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5;

<5> The salt according to <1> or <2>, wherein the organic counter ion is a cation represented by the formula (IIId) or (IIIe):

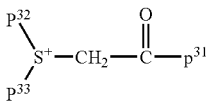

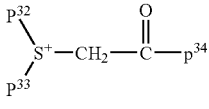

wherein $P^{31}$ represents an aromatic group which may be substituted, $P^{32}$ and $P^{33}$ are bonded to form a C3-C12 divalent acyclic hydrocarbon group which forms a ring together with the adjacent $S^+$, and at least one —$CH_2$— in the divalent acyclic hydrocarbon group may be replaced with —CO—, —O— or —S—, and $P^{34}$ represents a C1-C12 alkyl group;

<6> The salt according to any one of <1> to <5>, wherein the C3-C30 divalent alicyclic hydrocarbon group contains a cyclopentane, cyclohexane, adamantane or norbornane ring which may be substituted with at least one selected from a C1-C6 alkyl group, a C1-C6 alkoxy group, a C1-C4 perfluoroalkyl group, a C1-C6 hydroxyalkyl group, a hydroxyl group and a cyano group and at least one —$CH_2$— in the divalent alicyclic hydrocarbon group may be substituted with —CO— or —O—;

<7> The salt according to any one of <1> to <6>, wherein the C3-C30 cyclic hydrocarbon group contains at least one selected from a cyclopentane, cyclohexane, benzene, naphthalene, anthrathene, phenathrene and fluorene rings which may be substituted with at least one selected from a C1-C6 alkyl group, a C1-C6 alkoxy group, a C1-C4 perfluoroalkyl group, a C1-C6 hydroxyalkyl group, a hydroxyl group and a cyano group and at least one —CH$_2$— in the cyclic hydrocarbon group may be substituted with —CO— or —O—;

<8> The salt according to <1>, wherein the salt represented by the formula (I) is one represented by the formula (IVa), (IVb) or (IVc);

<9> The salt according to <1>, wherein the salt is one represented by the formula (Va), (Vb), (Vc), (Vd), (Ve) or (Vf):

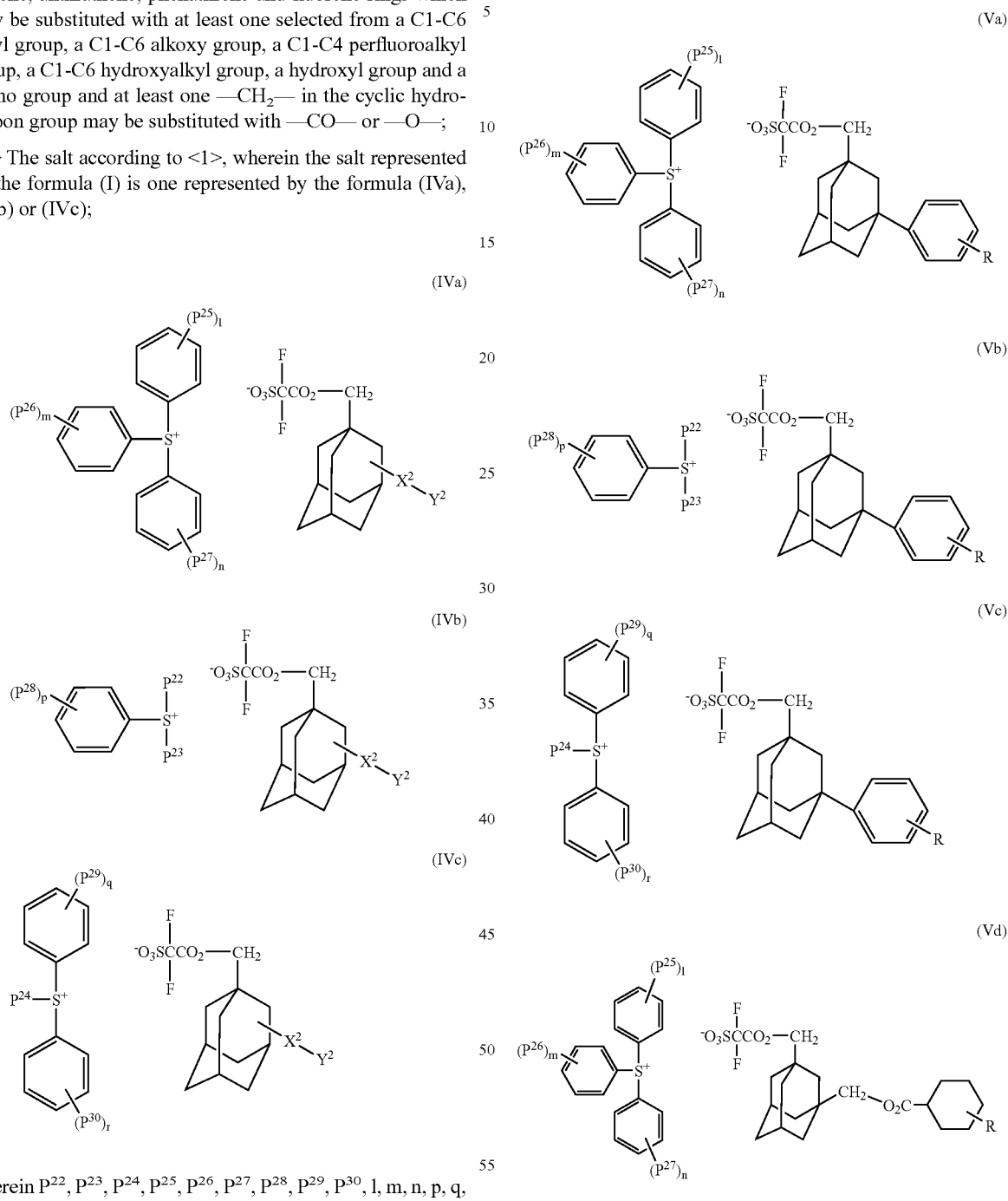

wherein P$^{22}$, P$^{23}$, P$^{24}$, P$^{25}$, P$^{26}$, P$^{27}$, P$^{28}$, P$^{29}$, P$^{30}$, l, m, n, p, q, and r are the same as defined in <4>, and Y$^2$ represents a cyclopentyl, cyclohexyl, phenyl, naphthyl, anthryl, phenanthryl or fluorenyl group which may be substituted with at least one group selected from a C1-C6 alkyl group, a C1-C6 alkoxy group, a C1-C4 perfluoroalkyl group, a C1-C6 hydroxyalkyl group, a hydroxyl group and a cyano group, and X$^2$ represents a single bond or a C1-C6 divalent hydrocarbon group and at least one —CH$_2$— in the C1-C6 divalent hydrocarbon group may be replaced with —CO— or —O—;

-continued (Vf)

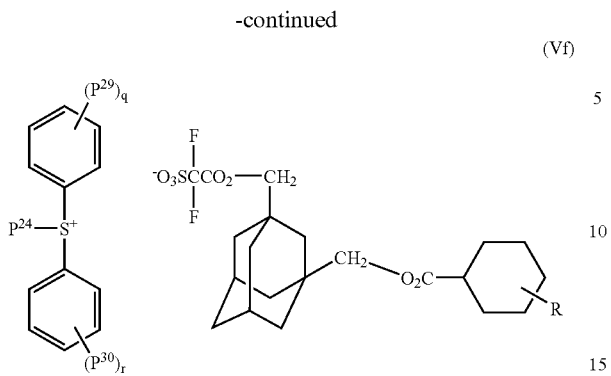

wherein $P^{22}$, $P^{23}$, $P^{24}$, $P^{25}$, $P^{26}$, $P^{27}$, $P^{28}$, $P^{29}$, $P^{30}$, l, m, n, p, q and r are the same as defined in <4>, and R represents a hydrogen atom, a C1-C6 alkyl group, a C1-C6 alkoxy group, a C1-C4 perfluoroalkyl group, a C1-C6 hydroxyalkyl group, a hydroxyl group or a cyano group;

<10> The salt according to <1>, wherein the salt represented by the formula (I) is one represented by the formula (IVd) or (IVe);

(IVd)

(IVe)

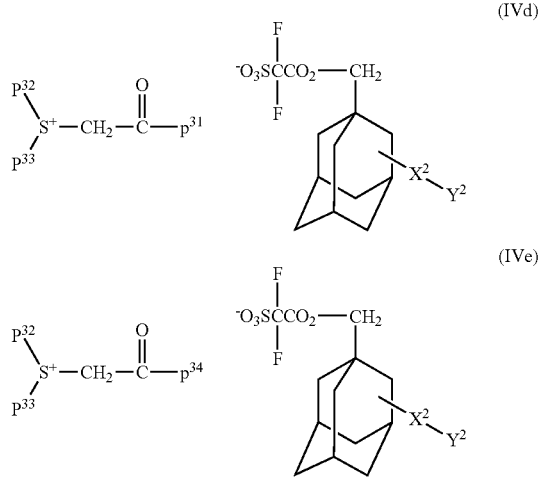

wherein $P^{31}$, $P^{32}$, $P^{33}$ and $P^{34}$ are the same as defined in <5> and $X^2$ and $Y^2$ are the same as defined in <8>;

<11> The salt according to <1>, wherein the salt is one represented by the formula (Vg), (Vh), (Vi) or (Vj):

(vg)

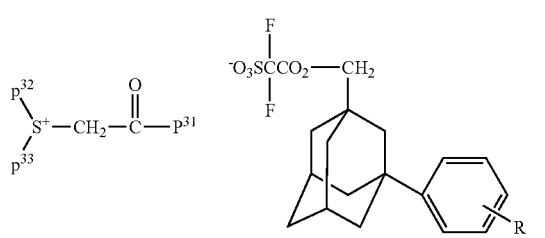

-continued (vh)

(vi)

(vj)

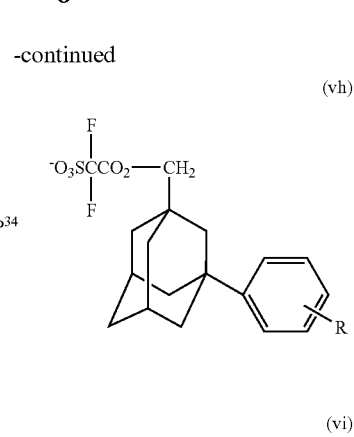

wherein $P^{31}$, $P^{32}$, $P^{33}$ and $P^{34}$ are the same as defined in <5> and R is the same as defined in <9>;

<12> A salt represented by the formula (VI):

(VI)

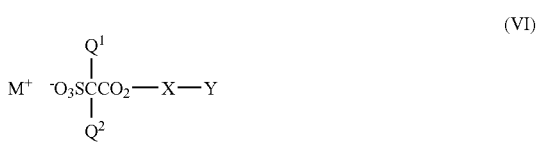

wherein

X represents a C3-C30 divalent group containing at least one divalent alicyclic hydrocarbon group, and at least one —$CH_2$— in the C3-C30 divalent group may be substituted with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be substituted with —O— or —CO—, $Q^1$ and $Q^2$ each independently represent a fluorine atom or a C1-C6 perfluoroalkyl group, and $M^+$ represents Li, Na, K or Ag;

<13> A process for production of a salt represented by the formula (VI):

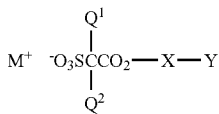 (VI)

wherein
X represents a C3-C30 divalent group containing at least one divalent alicyclic hydrocarbon group, and at least one —CH$_2$— in the C3-C30 divalent group may be substituted with —O— or —CO—,
Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be substituted with —O— or —CO—,
Q$^1$ and Q$^2$ each independently represent a fluorine atom or a C1-C6 perfluoroalkyl group, and M$^+$ represents Li, Na, K or Ag, which comprises reacting a compound represented by the formula (IX):

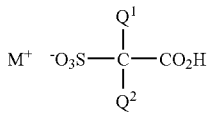 (IX)

wherein Q$^1$, Q$^2$ and M are the same as defined above, with a compound represented by the formula (VII):

HO—X—OH (VII)

wherein X is the same as the defined above, and a compound represented by the formula (VIII):

H—Y (VIII)

wherein Y is the same as defined above;

<14> A process for production of a salt represented by the formula (IV):

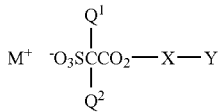 (VI)

wherein
X represents a C3-C30 divalent group containing at least one divalent alicyclic hydrocarbon group, and at least one —CH$_2$— in the C3-C30 divalent group may be substituted with —O— or —CO—,
Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be substituted with —O— or —CO—,
Q$^1$ and Q$^2$ each independently represent a fluorine atom or a C1-C6 perfluoroalkyl group, and M$^+$ represents Li, Na, K or Ag,
which comprises reacting a compound represented by the formula (IX):

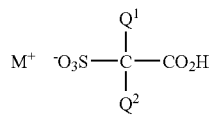 (IX)

wherein Q$^1$, Q$^2$ and M are the same as defined above, with a compound represented by the formula (X):

HO—X—Y (X)

wherein X and Y are the same as defined above;

<15> A process for production of a salt represented by the formula (I):

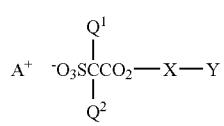 (I)

wherein
X represents a C3-C30 divalent group containing at least one divalent alicyclic hydrocarbon group, and at least one —CH$_2$— in the
C3-C30 divalent group may be substituted with —O— or —CO—,
Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be substituted with —O— or —CO—,
Q$^1$ and Q$^2$ each independently represent a fluorine atom or a C1-C6 perfluoroalkyl group, and A$^+$ represents an organic counter ion, which comprises reacting a salt represented by the formula (IV):

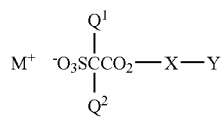 (VI)

wherein X and Y are the same as defined above and M$^+$ represents Li, Na, K or Ag, with a compound represented by the formula (XI):

A$^+$Z$^-$ (XI)

wherein A$^+$ is the same as defined above and Z represents F, Cl, Br, I, BF$_4$, AsF$_6$, SbF$_6$, PF$_6$ or ClO$_4$;

<16> A process for production of a salt represented by the formula (I):

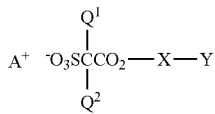
(I)

wherein

X represents a C3-C30 divalent group containing at least one divalent alicyclic hydrocarbon group, and at least one —$CH_2$— in the C3-C30 divalent group may be substituted with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be substituted with —O— or —CO—, $Q^1$ and $Q^2$ each independently represent a fluorine atom or a C1-C6 perfluoroalkyl group, and $A^+$ represents an organic counter ion, which comprises reacting a salt represented by the formula (XII):

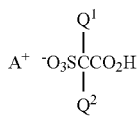
(XII)

wherein $Q^1$, $Q^2$ and $A^+$ are the same as defined above, with a compound represented by the formula (VII):

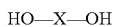  (VII)

wherein X is the same as the defined above, and a compound represented by the formula (VIII):

  (VIII)

wherein Y is the same as defined above;

<17> A process for production of a salt represented by the formula (I):

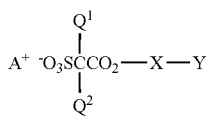
(I)

wherein

X represents a C3-C30 divalent group containing at least one divalent alicyclic hydrocarbon group, and at least one —$CH_2$— in the C3-C30 divalent group may be substituted with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be substituted with —O— or —CO—, $Q^1$ and $Q^2$ each independently represent a fluorine atom or a C1-C6 perfluoroalkyl group, and $A^+$ represents an organic counter ion, which comprises reacting a salt represented by the formula (XIII):

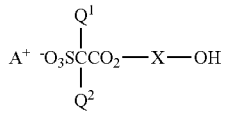
(XIII)

wherein $Q^1$, $Q^2$, $A^+$ and X are the same as defined above, with a compound represented by the formula (VIII):

  (VIII)

wherein Y is the same as defined above;

<18> A chemically amplified positive resist composition comprising a salt represented by the formula (I):

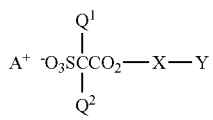
(I)

wherein

X represents a C3-C30 divalent group containing at least one divalent alicyclic hydrocarbon group, and at least one —$CH_2$— in the C3-C30 divalent group may be substituted with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be substituted with —O— or —CO—, $Q^1$ and $Q^2$ each independently represent a fluorine atom or a C1-C6 perfluoroalkyl group, and $A^+$ represents an organic counter ion, and a resin which contains a structural unit which has an acid-labile group and which itself is insoluble or poorly soluble in an aqueous alkali solution but becomes soluble in an aqueous alkali solution by the action of an acid;

<19> The chemically amplified positive resist composition according to <18>, wherein $Q^1$ and $Q^2$ each independently represent a fluorine atom or a trifluoromethyl group;

<20> The chemically amplified positive resist composition according to <18> or <19>, wherein the organic counter ion is at least one cation selected from a cation represented by the formula (IIa):

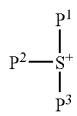
(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

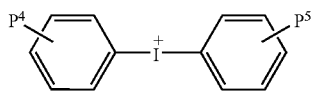
(IIb)

wherein $P^4$ and $P^5$ each independently represent a hydrogen atom, a hydroxyl group, a C1-C12 alkyl group or a C1-C12 alkoxy group, a cation represented by the formula (IIc):

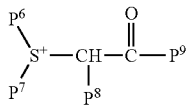
(IIc)

wherein
$P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —$CH_2$— in the divalent acyclic hydrocarbon group may be substituted with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded to form a divalent acyclic hydrocarbon group which forms a 2-oxo-cycloalkyl group together with the adjacent —CHCO—, and at least one —$CH_2$— in the divalent acyclic hydrocarbon group may be substituted with —CO—, —O— or —S—, and a cation represented by the formula (IId):

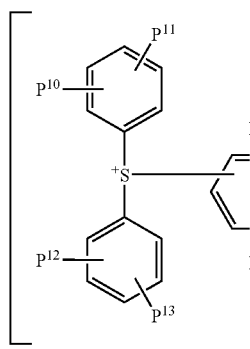
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1;

<21> The chemically amplified positive resist composition according to <18> or <19>, wherein the organic counter ion is a cation represented by the formula (IIIa), (IIIb) or (IIIc):

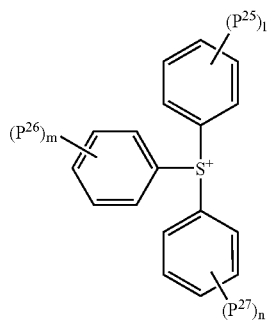
(IIIa)

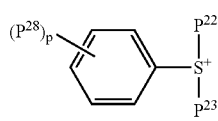
(IIIb)

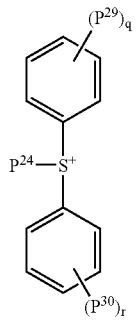
(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5;

<22> The chemically amplified positive resist composition according to <18> or <19>, wherein the organic counter ion is a cation represented by the formula (IIId) or (IIIe):

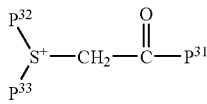
(IIId)

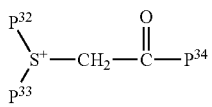
(IIIe)

wherein $P^{31}$ represents an aromatic group which may be substituted, $P^{32}$ and $P^{33}$ are bonded to form a C3-C12 divalent acyclic hydrocarbon group which forms a ring together with the adjacent S$^+$, and at least one —CH$_2$— in the divalent acyclic hydrocarbon group may be replaced with —CO—, —O— or —S—, and $P^{34}$ represents a C1-C12 alkyl group;

<23> The chemically amplified positive resist composition according to any one of <18> to <22>, wherein the resin contains a structural unit derived from a monomer having a bulky and acid-labile group;

<24> The chemically amplified positive resist composition according to any one of <18> to <22>, wherein the resin contains a structure unit derived from hydroxystyrene;

<25> The chemically amplified positive resist composition according to <24>, wherein a resin contains a structural unit which is derived from hydroxystyrene and in which a part of hydroxyl groups are protected with acid-labile groups in addition to the structural unit derived from hydroxystyrene;

<26> The chemically amplified positive resist composition according to any one of <18> to <25>, wherein the chemically amplified positive resist composition further comprises a basic compound.

DESCRIPTION OF PREFERRED EMBODIMENTS

The present invention provides a salt represented by the formula (I) (hereinafter, simply referred to as Salt (I)).

The C3-C30 divalent group contains at least one divalent alicyclic hydrocarbon group. At least one —CH$_2$— in the C3-C30 divalent group may be substituted with —O— or —CO—. It is preferred that the C3-C30 divalent group contains a divalent alicyclic hydrocarbon group.

The C3-C30 divalent group may include a C1-C6 alkoxy group, a C1-C4 perfluoroalkyl group, a C1-C6 hydroxyalkyl group, a hydroxyl group or a cyano group. Examples of the C1-C6 alkoxy group include a methoxy, ethoxy, n-propoxy, isopropoxy, n-butoxy, sec-butoxy, tert-butoxy, n-pentyloxy and n-hexyloxy group. Examples of the C1-C4 perfluoroalkyl group include a trifluoromethyl, pentafluoroethyl, heptafluoropropyl and nonafluorobutyl group. Examples of the C1-C6 hydroxyalkyl group include a hydroxymethyl, 2-hydroxyethyl, 3-hydroxypropyl, 4-hydroxybutyl and 6-hydroxyhexyl group.

As the C3-C30 divalent group, the C6-C20 divalent group is preferable and the C6-C15 divalent group is more preferable.

The divalent alicyclic hydrocarbon group may include the C1-C6 alkoxy group, the C1-C4 perfluoroalkyl group, the C1-C6 hydroxyalkyl group, the hydroxyl group or the cyano group. At least one —CH$_2$— in the divalent alicyclic hydrocarbon group may be substituted with —O— or —CO—.

Examples of the divalent alicyclic hydrocarbon group include a cyclopentanediyl group, a cyclohexanediyl group, a norbornanediyl group, a decahydronaphthalenediyl group, an adamantanediyl group, a cyclohexadienediyl group, and the following groups.

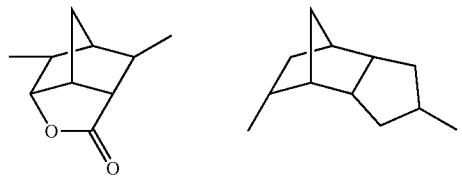

In the above formulae, the straight line with an open end shows a bond extended from an adjacent group.

Preferred examples of the divalent alicyclic hydrocarbon group include the followings.

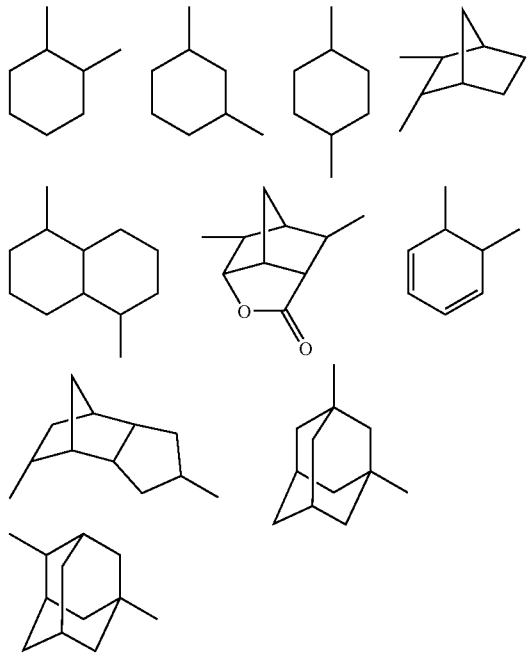

In the above formulae, the straight line with an open end shows a bond extended from an adjacent group.

The C3-C30 divalent group may be the above-mentioned divalent alicyclic group, and may be a group consisting of the above-mentioned divalent alicyclic hydrocarbon group and one or two divalent hydrocarbon groups in which at least one —CH$_2$— may be substituted with —O— or —CO—. Examples of the divalent hydrocarbon group in which at least one —CH$_2$— may be substituted with —O— or —CO— include a C1-C6 hydrocarbon group in which at least one —CH$_2$— may be substituted with —O— or —CO—. Preferable examples thereof include —CH$_2$—, —CH$_2$CH$_2$—, —CH$_2$CH$_2$CH$_2$—, —CH$_2$CH$_2$CH$_2$CH$_2$—, —O—, —CO—, —O—CO—, —CH$_2$—O—CO— and —O—CO—CH$_2$—. More preferable examples thereof include —CH$_2$—, —CH$_2$CH$_2$—, —CH$_2$CH$_2$CH$_2$—, —O—CO— and —CH$_2$—O—CO—.

Specific examples of the C3-C30 divalent group include the followings.

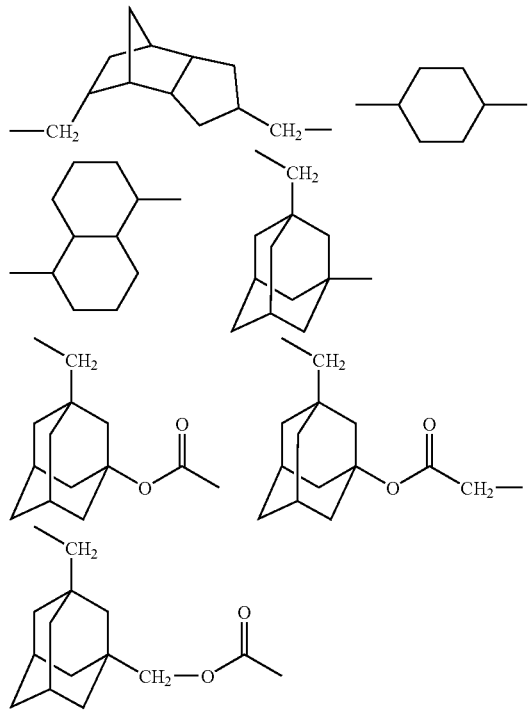

In the above formulae, the straight line with an open end shows a bond extended from an adjacent group.

Preferred examples thereof include the followings:

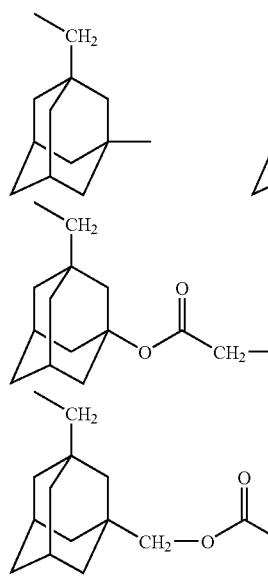

and more preferred examples thereof include the followings:

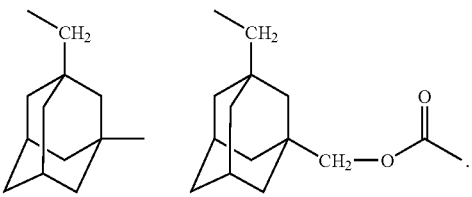

In the above formulae, the straight line with an open end shows a bond extended from an adjacent group.

Y represents a C3-C30 cyclic hydrocarbon group, and the C3-C30 cyclic hydrocarbon group may be substituted with at least one group selected from a C1-C6 alkoxy group, a C1-C4 perfluoroalkyl group, a C1-C6 hydroxyalkyl group, a hydroxyl group and a cyano group. At least one —CH$_2$— in the C3-C30 cyclic hydrocarbon group may be substituted with —O— or —CO—. The C3-C30 cyclic hydrocarbon group may have monocycle or bicycle or more. The C3-C30 cyclic hydrocarbon group may have at least one carbon-carbon double bond. The C3-C30 cyclic hydrocarbon group may be an alicyclic hydrocarbon group or an aromatic hydrocarbon group.

As the C1-C6 alkoxy group, the C1-C4 perfluoroalkyl group and the C1-C6 hydroxyalkyl group, the same groups as described above are exemplified.

It is preferred that Y represents the C5-C20 cyclic hydrocarbon group which may be substituted with at least one group selected from the C1-C6 alkoxy group and the C1-C6 hydroxyalkyl group, and it is more preferred that Y represents the C6-C16 cyclic hydrocarbon group which may be substituted with at least one group selected from the C1-C6 alkoxy group and the C1-C6 hydroxyalkyl group. At least one —CH$_2$— in the C5-C20 cyclic hydrocarbon group and the C6-C16 cyclic hydrocarbon group may be substituted with —O— or —CO—.

Examples of the C3-C30 cyclic hydrocarbon group include the followings.

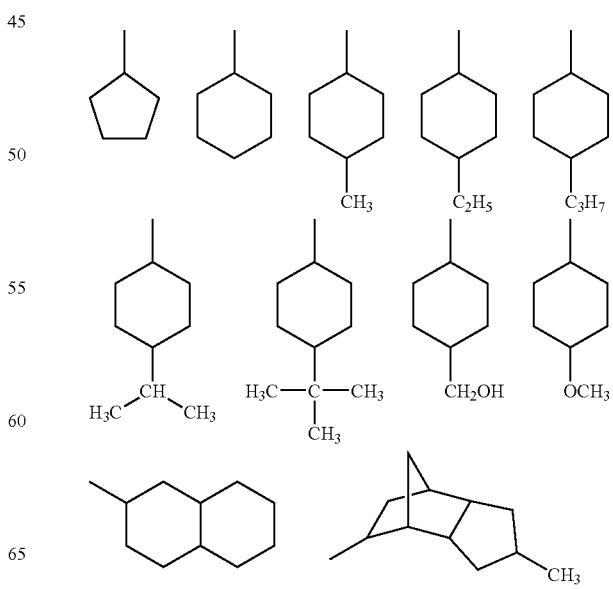

-continued

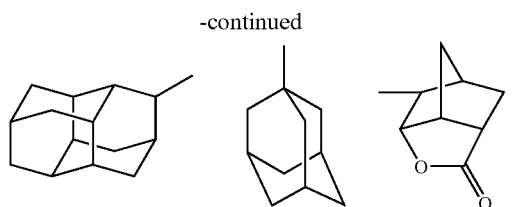
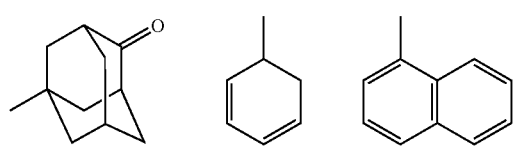
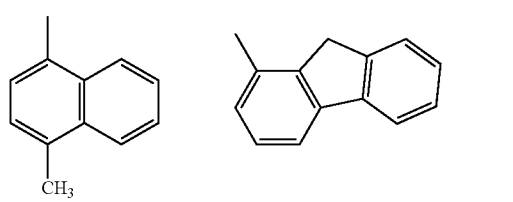
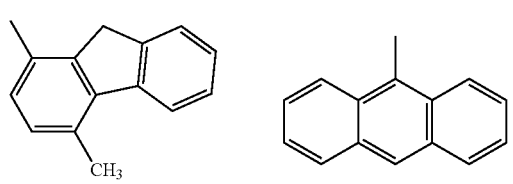
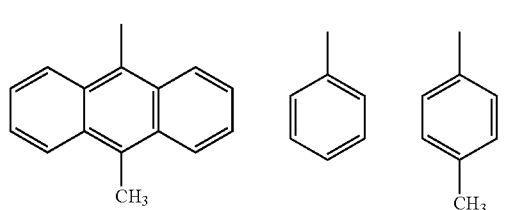
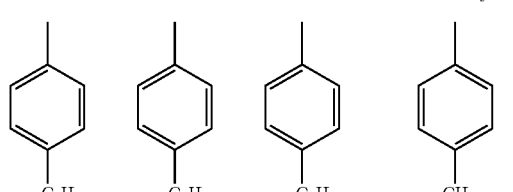
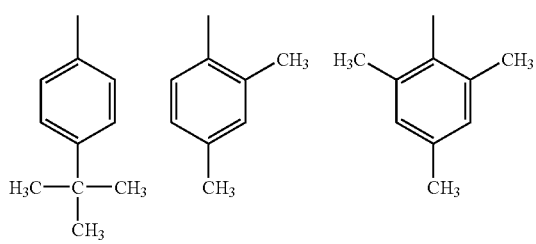
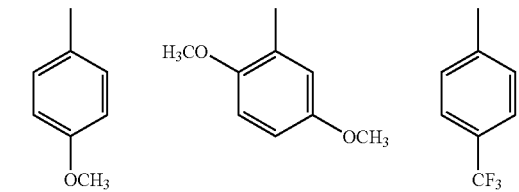

-continued

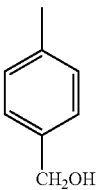

In the above formulae, the straight line with an open end shows a bond extended from an adjacent group.
Preferred examples thereof include the followings.

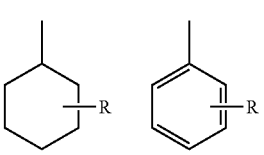

In the above formulae, R represents a hydrogen atom, a C1-C6 alkyl group, a C1-C6 alkoxy group, a C1-C6 perfluoroalkyl group or a C1-C6 hydroxyalkyl group, and the straight line with an open end shows a bond extended from an adjacent group. As R, the hydrogen atom, the C1-C6 alkyl group, the C1-C6 alkoxy group and the C1-C6 hydroxyalkyl group are preferable.

The followings:

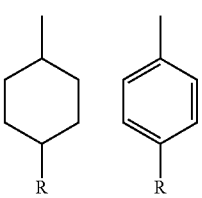

are more preferred.

In the above formulae, R represents the same meaning as defined above, and the straight line with an open end shows a bond extended from an adjacent group.

$Q^1$ and $Q^2$ each independently represent a fluorine atom or a C1-C6 perfluoroalkyl group.

Examples of the C1-C6 perfluoroalkyl group include a trifluoromethyl, pentafluoroethyl, heptafluoropropyl, nonafluorobutyl undecafluoropentyl and tridecafluorohexyl group, and the trifluoromethyl group is preferable.

It is preferable that $Q^1$ and $Q^2$ each independently represent the fluorine atom or the trifluoromethyl group, and it is more preferable that $Q^1$ and $Q^2$ represent the fluorine atoms.

Specific examples of the anion part of Salt (I) include the followings.

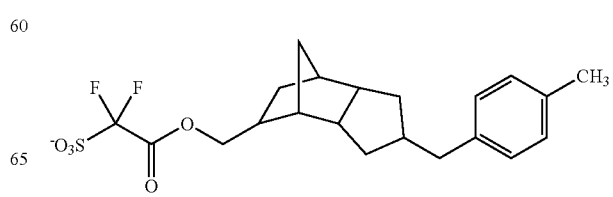

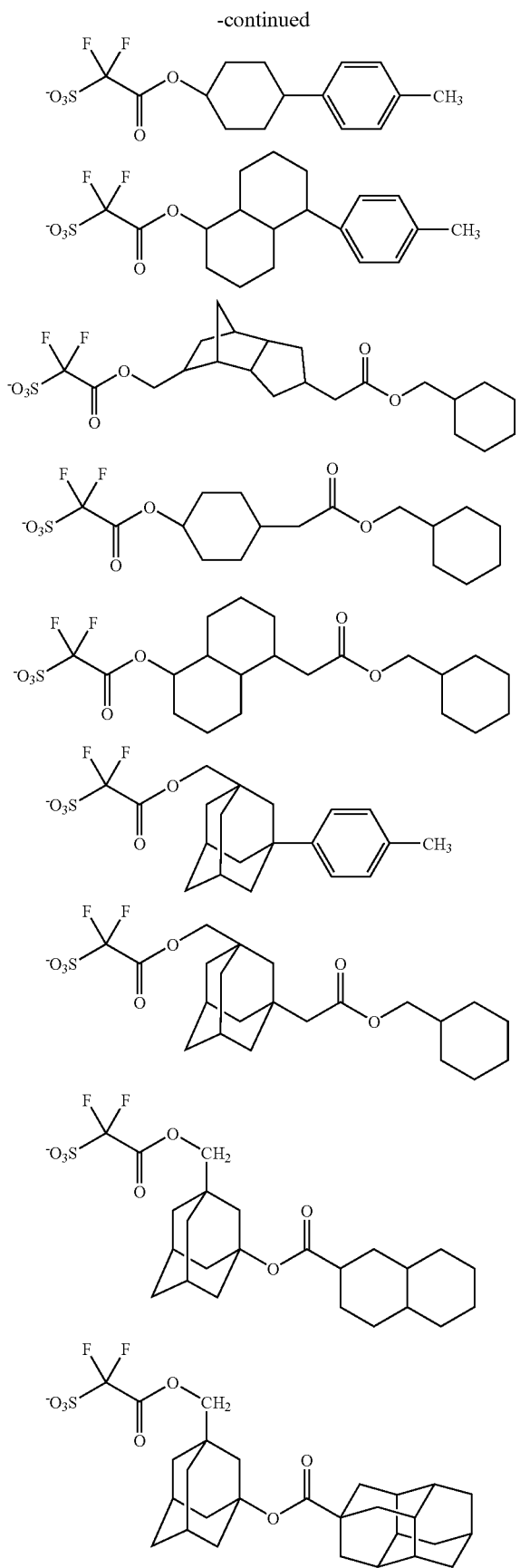
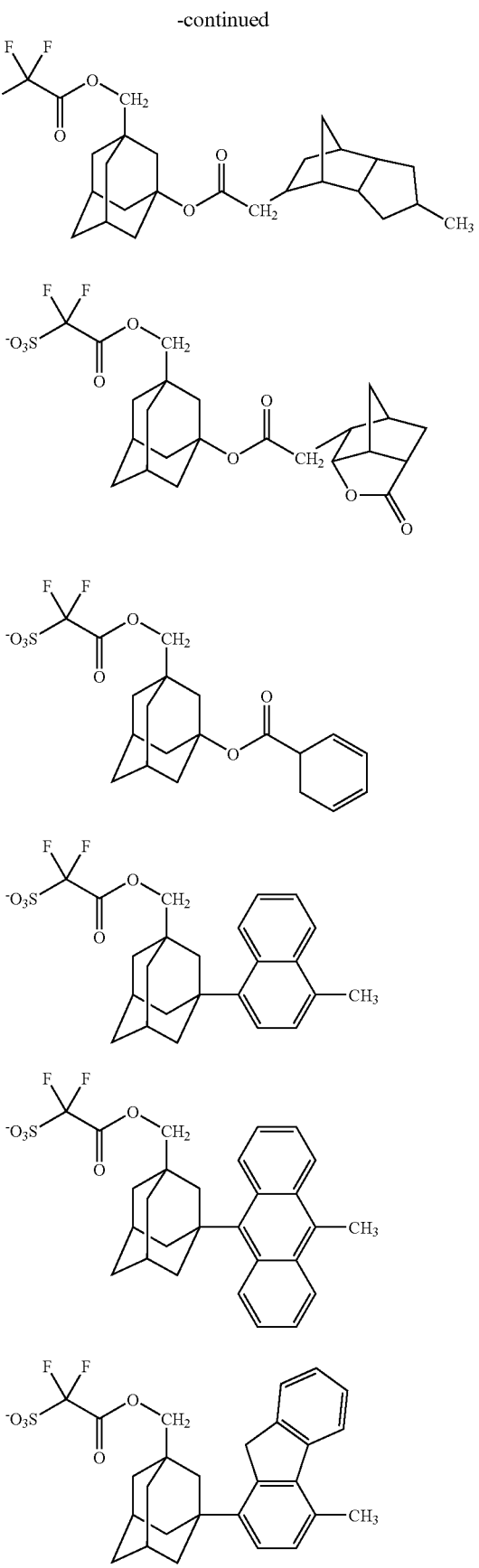

-continued
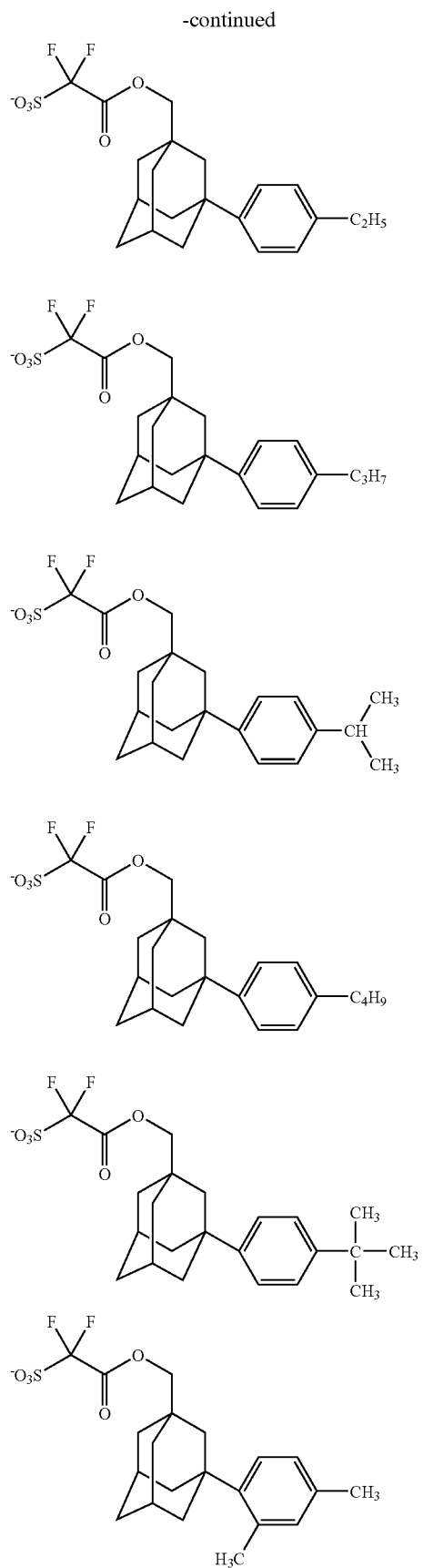
-continued
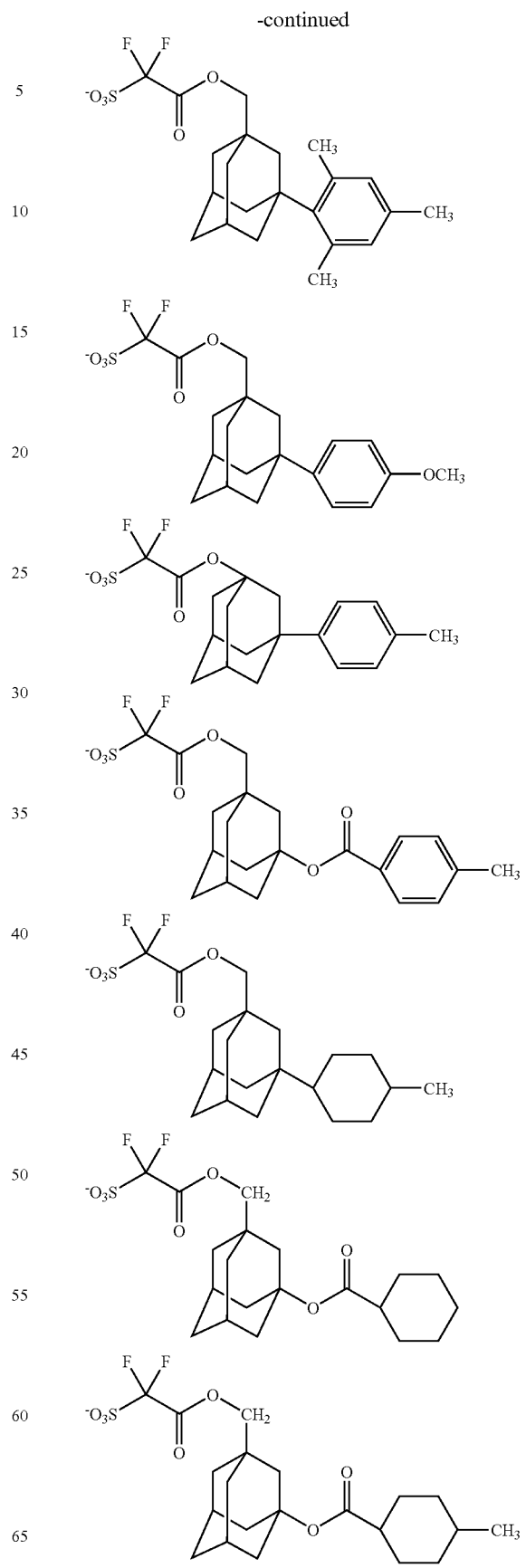

-continued
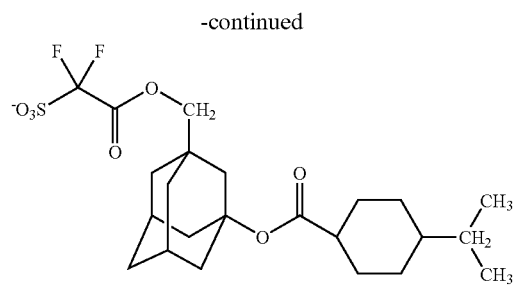
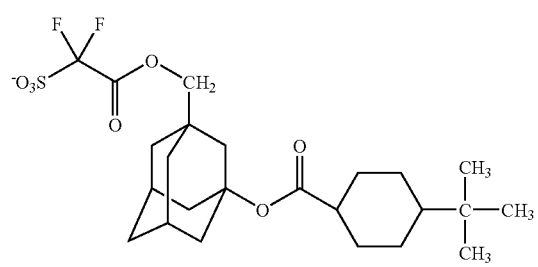
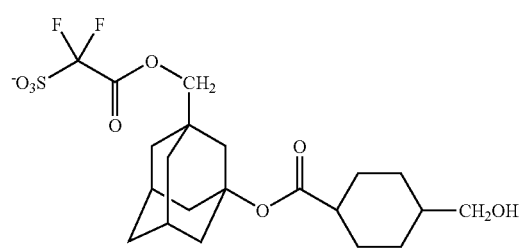
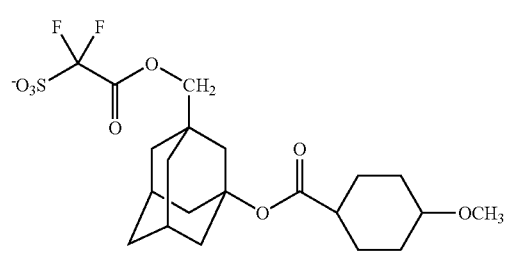
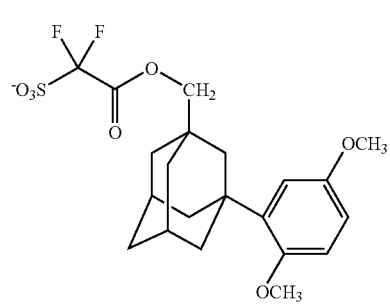
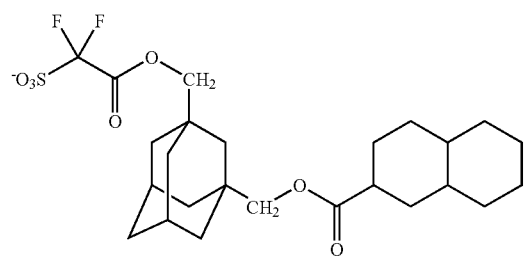
-continued
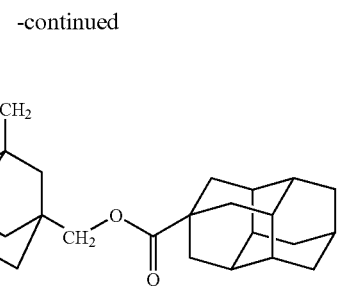
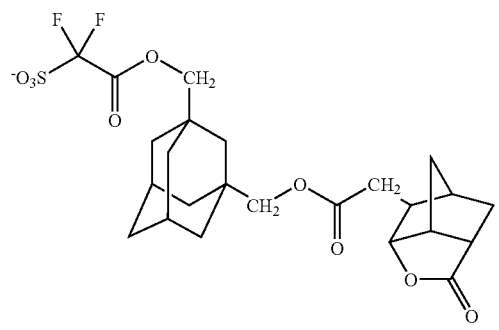
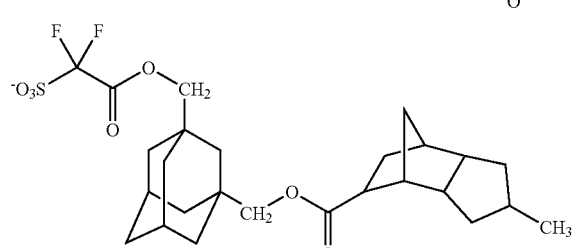
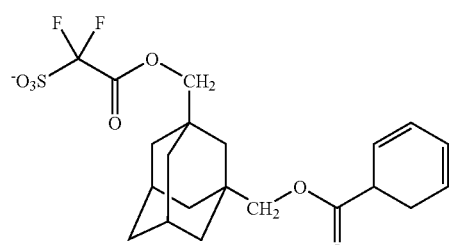
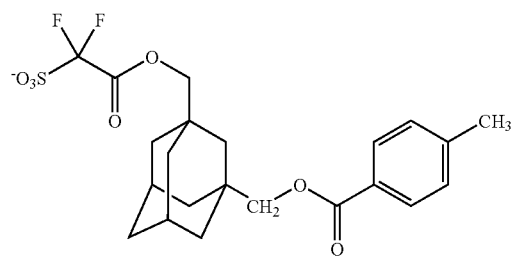
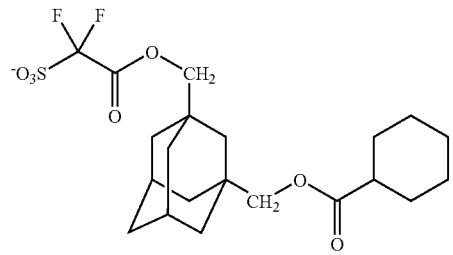

-continued

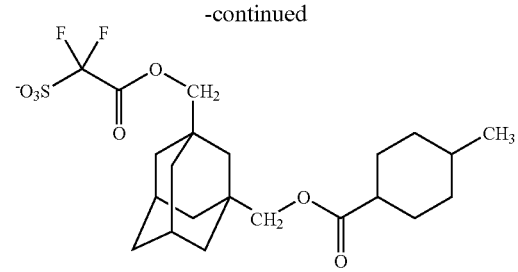

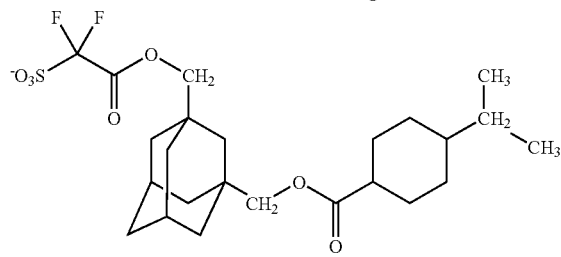

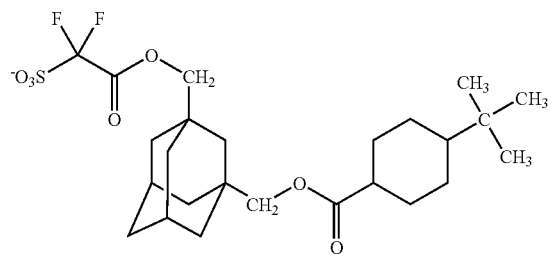

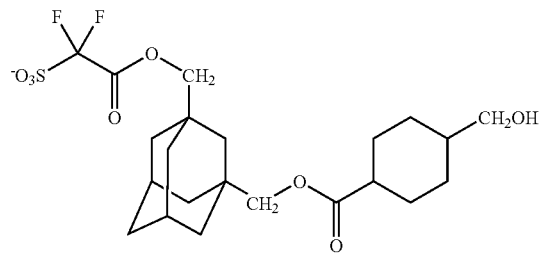

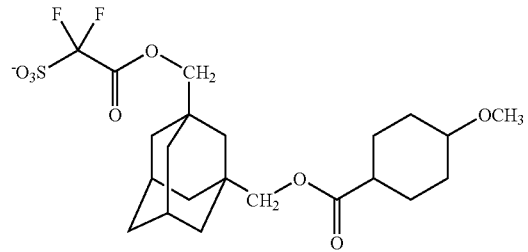

Among them, the following anion part of Salt (I) is preferable.

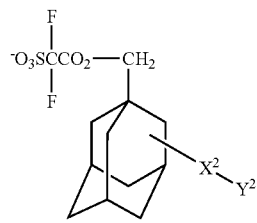

In the above formula, $Y^2$ represents a cyclopentyl, cyclohexyl, phenyl, naphthyl, anthryl, phenanthryl or fluorenyl group which may be substituted with at least one group selected from a C1-C6 alkyl group, a C1-C6 alkoxy group, a C1-C4 perfluoroalkyl group, a C1-C6 hydroxyalkyl group, a hydroxyl group and a cyano group, and $X^2$ represents a single bond or a C1-C6 divalent hydrocarbon group and at least one —$CH_2$— in the C1-C6 divalent hydrocarbon group may be replaced with —CO— or —O—.

It is more preferred that the anion parts of Salt (I) are the followings.

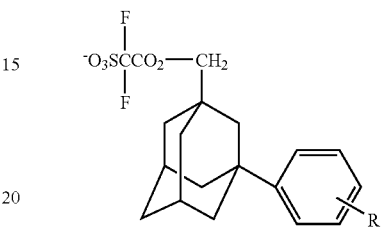

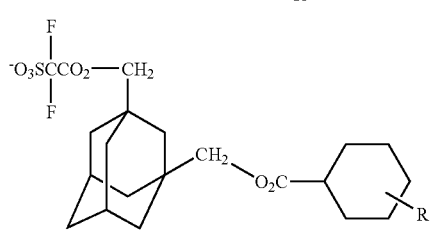

Specific examples of the preferable anion parts of Salt (I) include the followings.

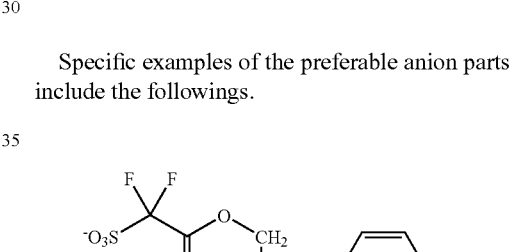

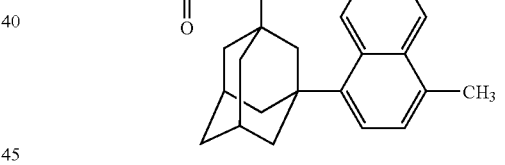

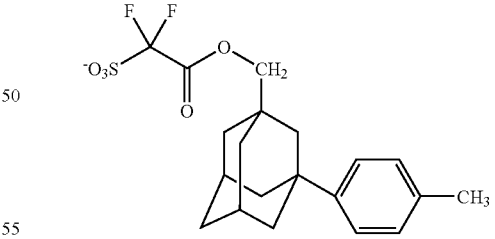

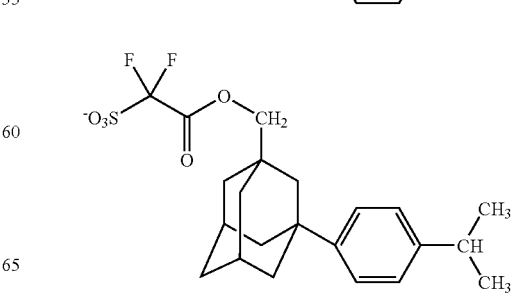

-continued
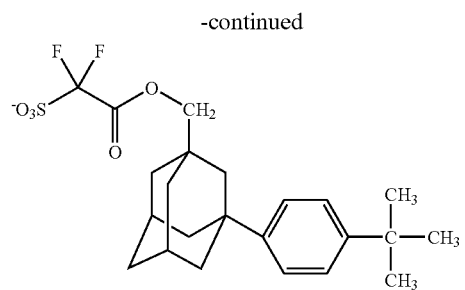
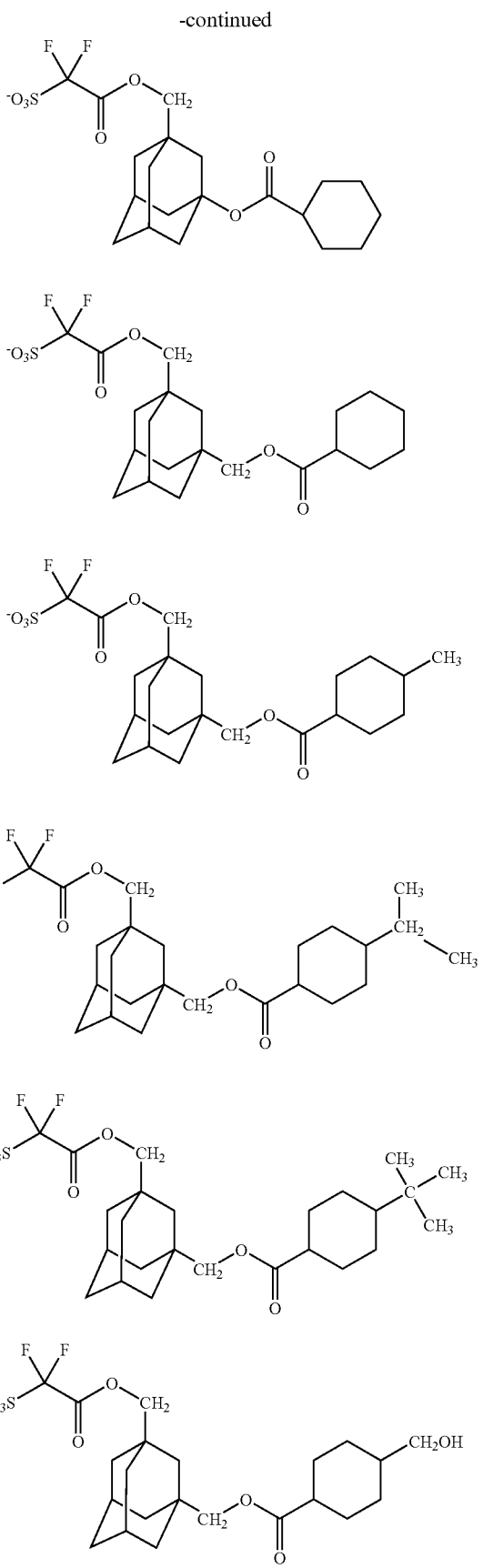

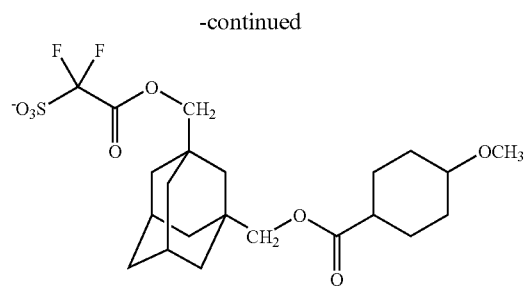
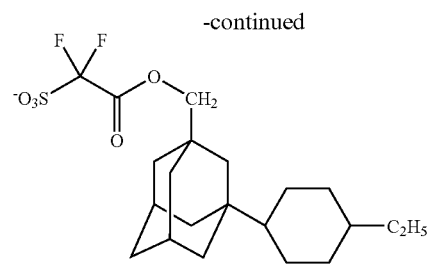
It is more preferred that the anion parts of Salt (I) are the followings.
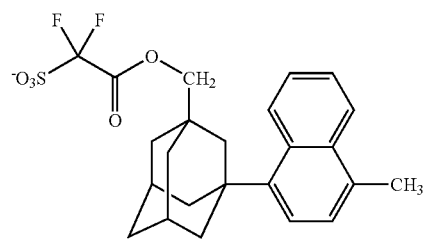
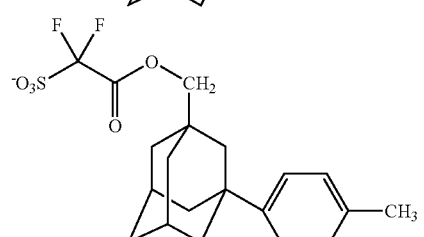
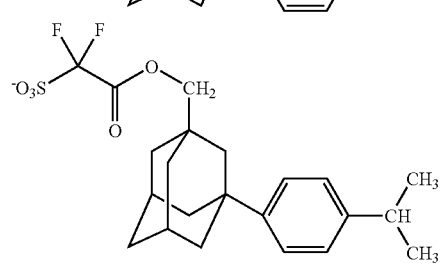
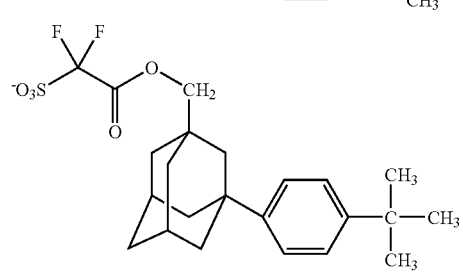
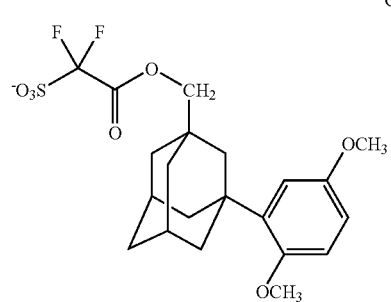
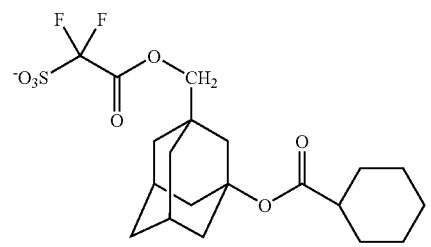
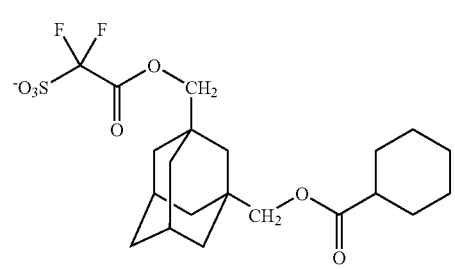
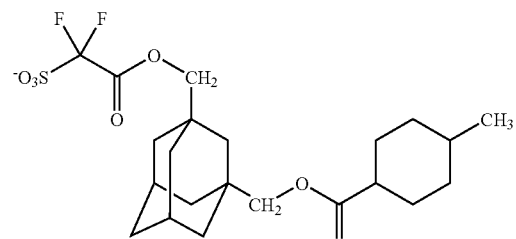
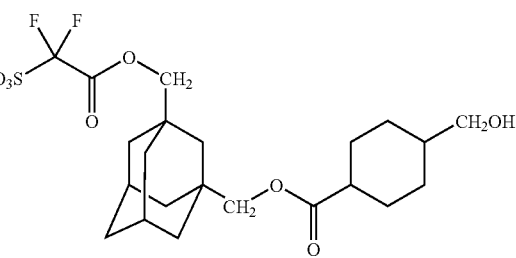
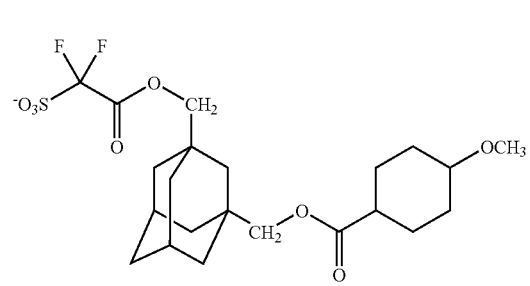

In the formula (I), $A^+$ represents an organic counter ion.

Examples of the organic counter ion include a cation represented by the formula (IIa):

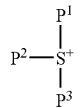

(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

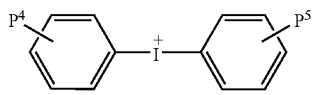

(IIb)

wherein $P^4$ and $P^5$ each independently represent a hydrogen atom, a hydroxyl group, a C1-C12 alkyl group or a C1-C12 alkoxy group, a cation represented by the formula (IIc):

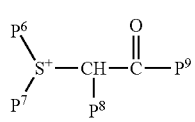

(IIc)

wherein $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and at least one —CH$_2$— in the divalent acyclic hydrocarbon group may be replaced with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ bond to form a divalent acyclic hydrocarbon group which forms a 2-oxo-cycloalkyl group together with the adjacent —CHCO—, and at least one —CH$_2$— in the divalent acyclic hydrocarbon group may be replaced with —CO—, —O— or —S—, and a cation represented by the formula (IId):

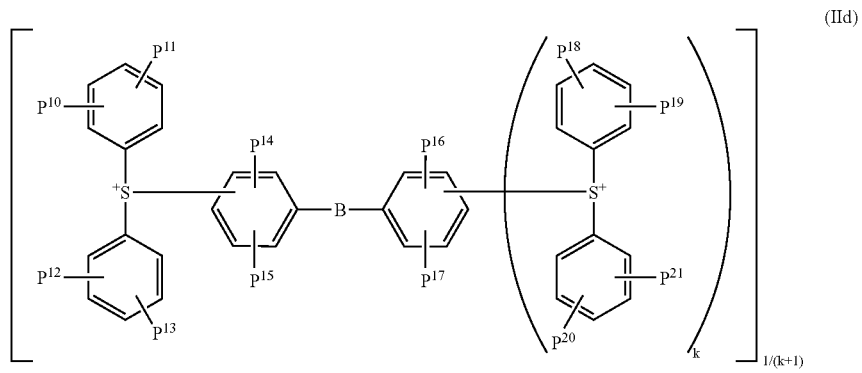

(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

Examples of the C1-C12 alkoxy group in the formulae (IIa), (IIb) and (IId) include a methoxy, ethoxy, n-propoxy, isopropoxy, n-butoxy, isobutoxy, sec-butoxy, tert-butoxy, n-pentyloxy, n-hexyloxy, n-octyloxy and 2-ethylhexyloxy group.

Examples of the C3-C12 cyclic hydrocarbon group in the formula (IIa) include a cyclopentyl, cyclohexyl, 1-adamantyl, 2-adamantyl, phenyl, 2-methylphenyl, 4-methylphenyl, 1-naphthyl and 2-naphthyl group. Examples of the C1-C30 alkyl group which may be substituted with at least one selected from the hydroxyl group, the C3-C12 cyclic hydrocarbon group and the C1-C12 alkoxy group in the formula (IIa) include a methyl, ethyl, n-propyl, isopropyl, n-butyl, isobutyl, sec-butyl, tert-butyl, n-pentyl, n-hexyl, n-octyl, 2-ethylhexyl and benzyl group.

Examples of the C3-C30 cyclic hydrocarbon group which may be substituted with at least one selected from the hydroxyl group and the C1-C12 alkoxy group in the formula (IIa) include a cyclopentyl, cyclohexyl, 1-adamantyl, 2-adamantyl, bicyclohexyl, phenyl, 2-methylphenyl, 4-methylphenyl, 4-ethylphenyl, 4-isopropylphenyl, 4-tert-butylphenyl, 2,4-dimethylphenyl, 2,4,6-trimethylphenyl, 4-n-hexylphenyl, 4-n-octylphenyl, 1-naphthyl, 2-naphthyl, fluorenyl, 4-phenylphenyl, 4-hydroxyphenyl, 4-methoxyphenyl, 4-tert-butoxyphenyl, 4-n-hexyloxyphenyl group.

Examples of the C1-C12 alkyl group in the formulae (IIb), (IIc) and (IId) include a methyl, ethyl, n-propyl, isopropyl, n-butyl, isobutyl, sec-butyl, tert-butyl, n-pentyl, n-hexyl, n-octyl and 2-ethylhexyl group.

Examples of the C3-C12 cycloalkyl group in the formula (IIc) include a cyclopropyl, cyclobutyl, cyclopentyl, cyclohexyl, cycloheptyl, cyclooctyl and cyclodecyl group. Examples of the C3-C12 divalent acyclic hydrocarbon group formed by bonding $P^6$ and $P^7$ include a trimethylene, tetramethylene, pentamethylene group. Examples of the ring group formed together with the adjacent $S^+$ and the divalent acyclic hydrocarbon group include a tetramethylenesulfonio, pentamethylenesulfonio and oxybisethylenesulfonio group.

Examples of the aromatic group in the formula (IIc) include a phenyl, tolyl, xylyl, 4-n-butylphenyl, 4-isobutylphenyl, 4-tert-butylphenyl, 4-cyclohexylphenyl, 4-phenylphenyl and naphthyl group. The aromatic group may be substituted, and the examples of the substituents include a C1-C6 alkoxy group such as a methoxy, ethoxy, n-propoxy, n-butoxy, tert-butoxy and n-hexyloxy group; a C2-C12 acyloxy group such as an acetyloxy and 1-adamantylcarbonyloxy group; and a nitro group.

Examples of the divalent acyclic hydrocarbon group formed by bonding $P^8$ and $P^9$ include a methylene, ethylene, trimethylene, tetramethylene and pentamethylene group and examples of the 2-oxocycloalkyl group formed together with the adjacent —CHCO— and the divalent acyclic hydrocarbon group include a 2-oxocyclopentyl and 2-oxocyclohexyl group.

Examples of the cation represented by the formula (IIa) include the followings:

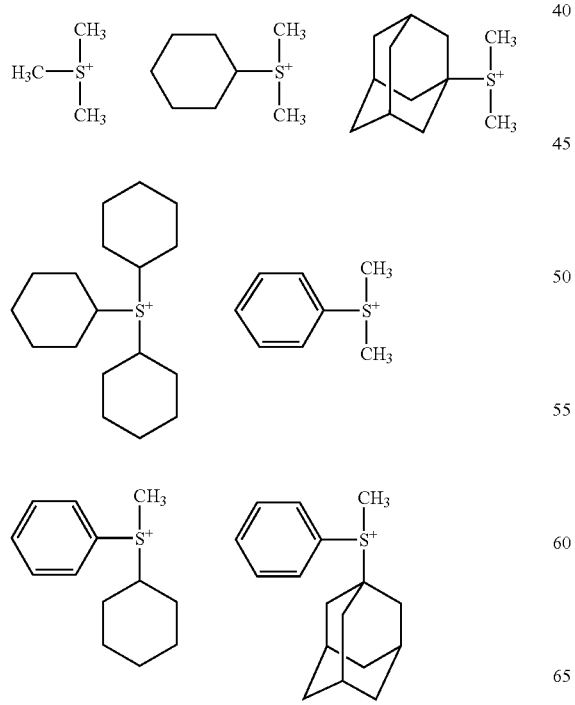

-continued

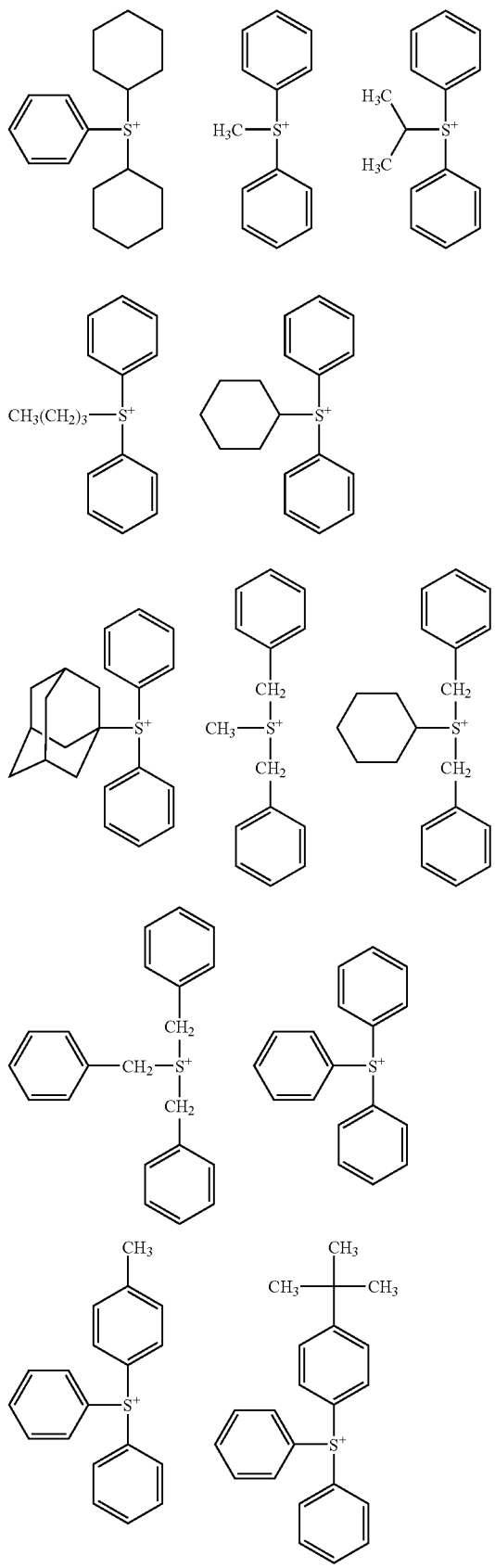

-continued
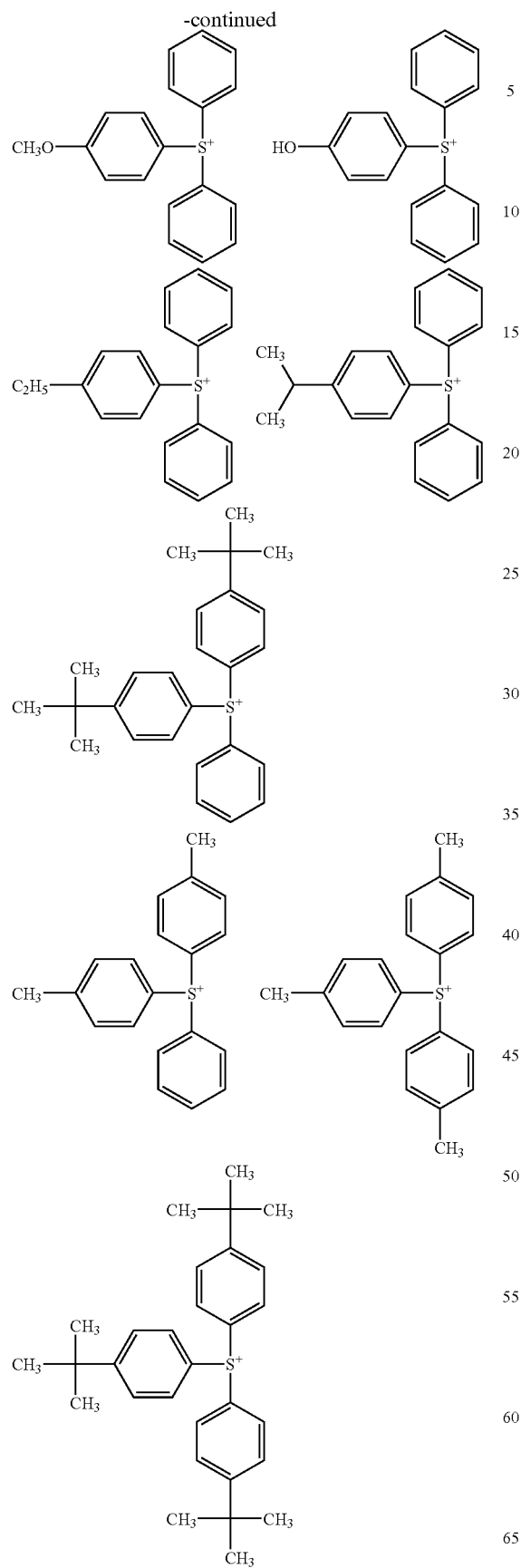
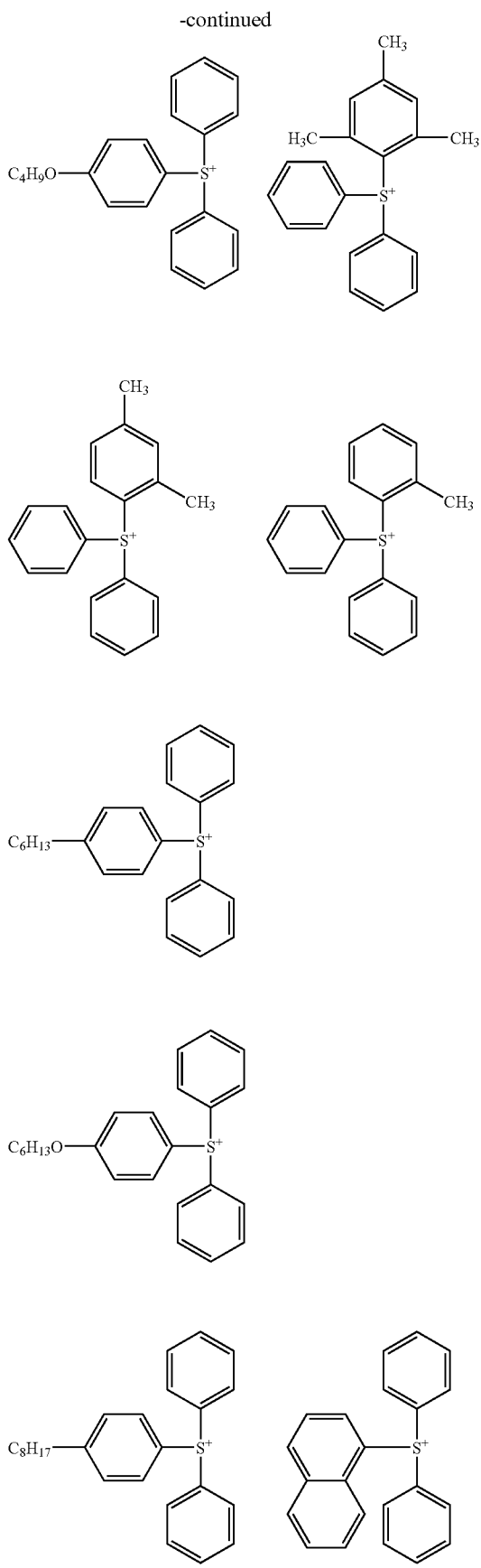

-continued
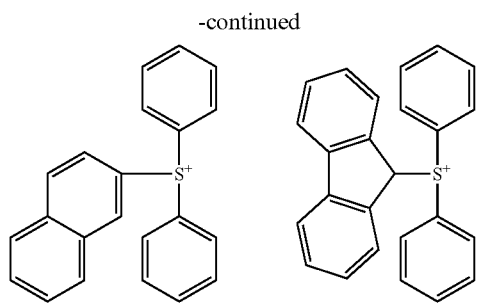
Examples of the cation represented by the formula (IIb) include the followings:
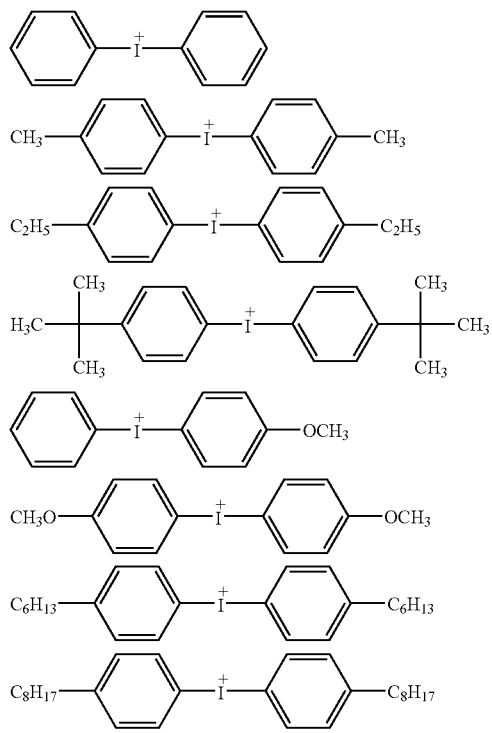
Examples of the cation represented by the formula (IIc) include the followings:
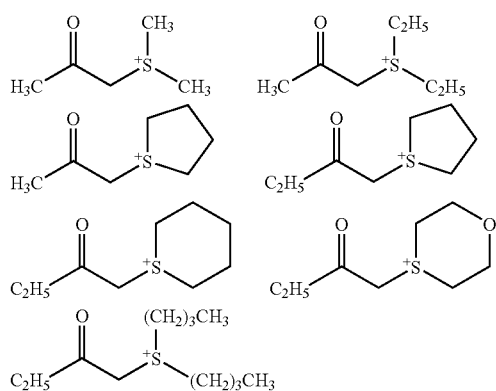
-continued
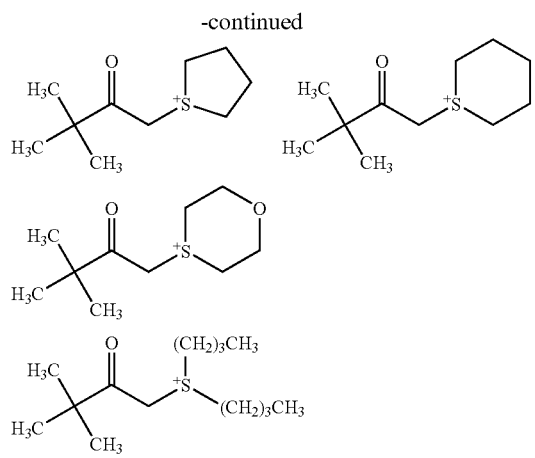

-continued
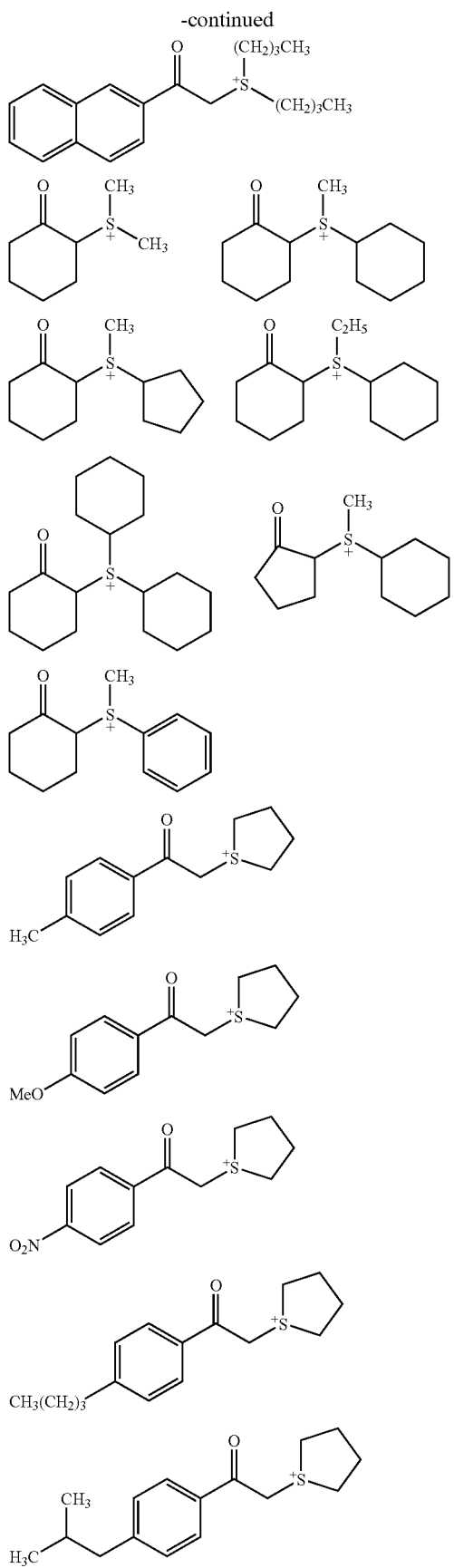
-continued
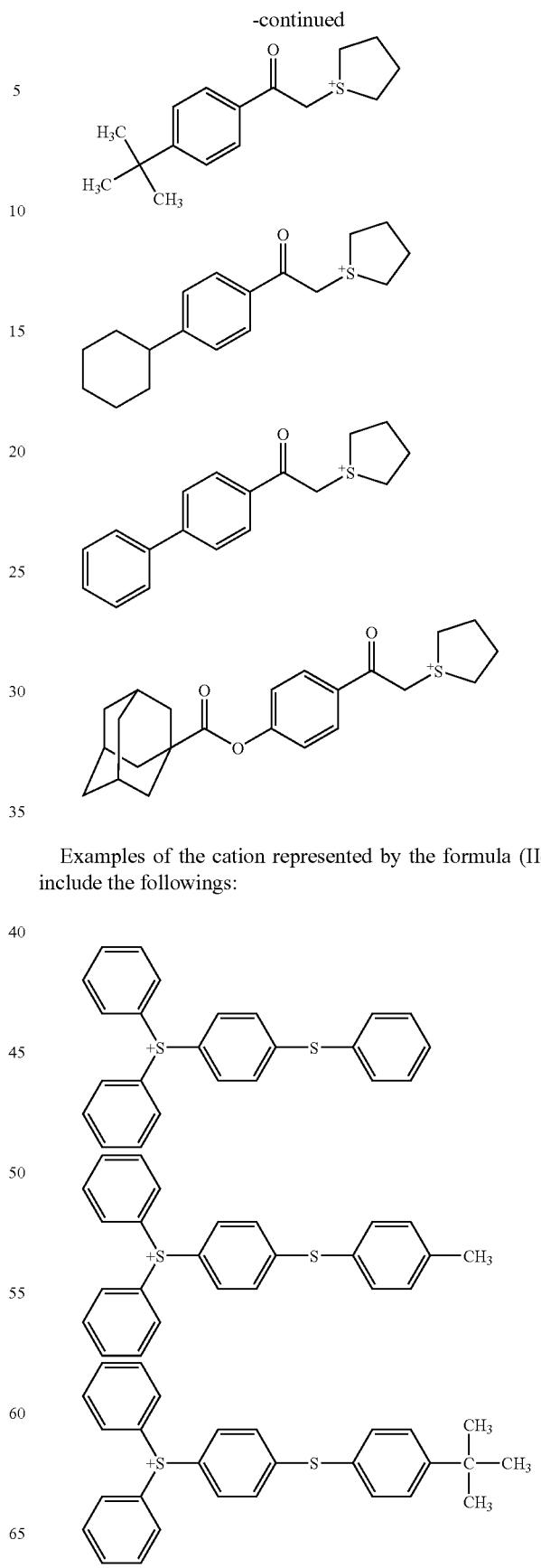
Examples of the cation represented by the formula (IId) include the followings:

-continued
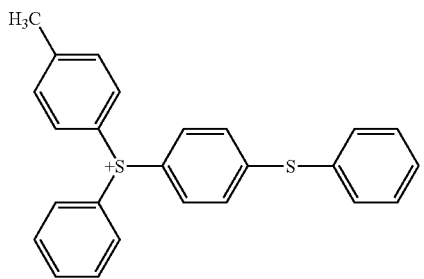
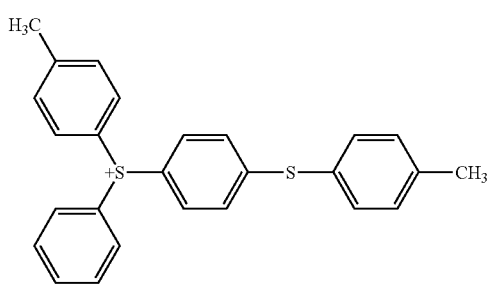
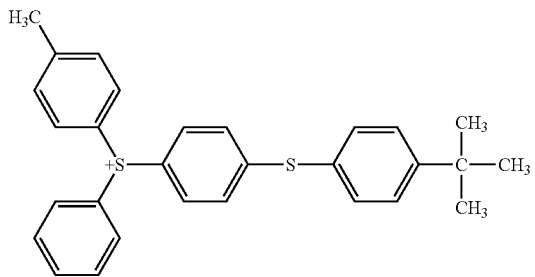
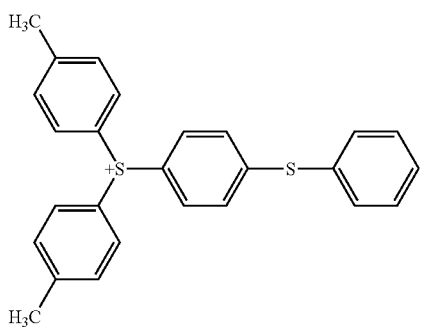
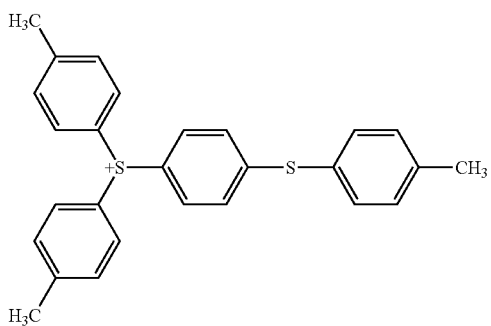
-continued
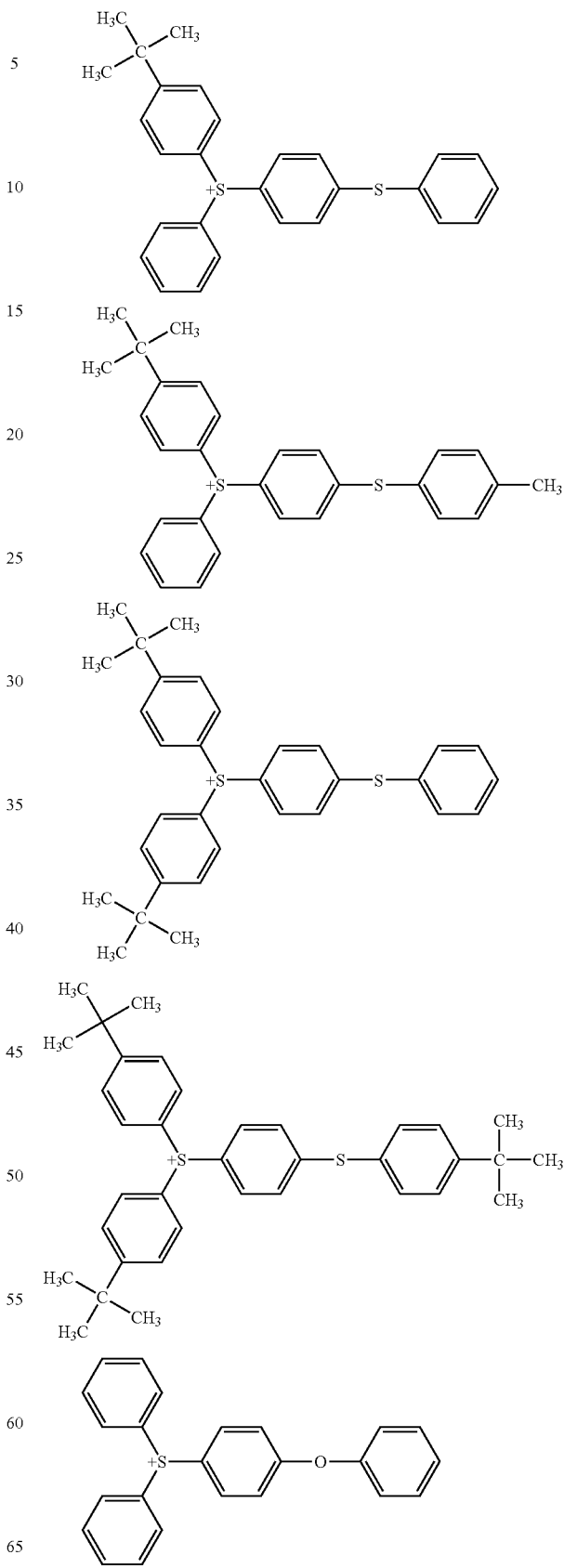

-continued
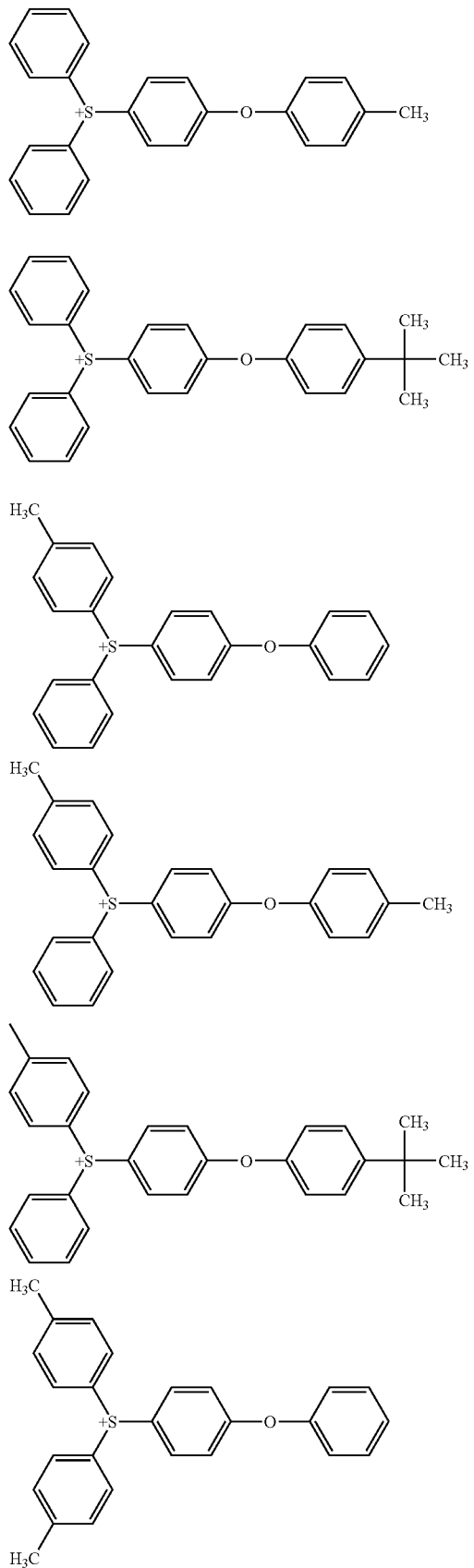
-continued
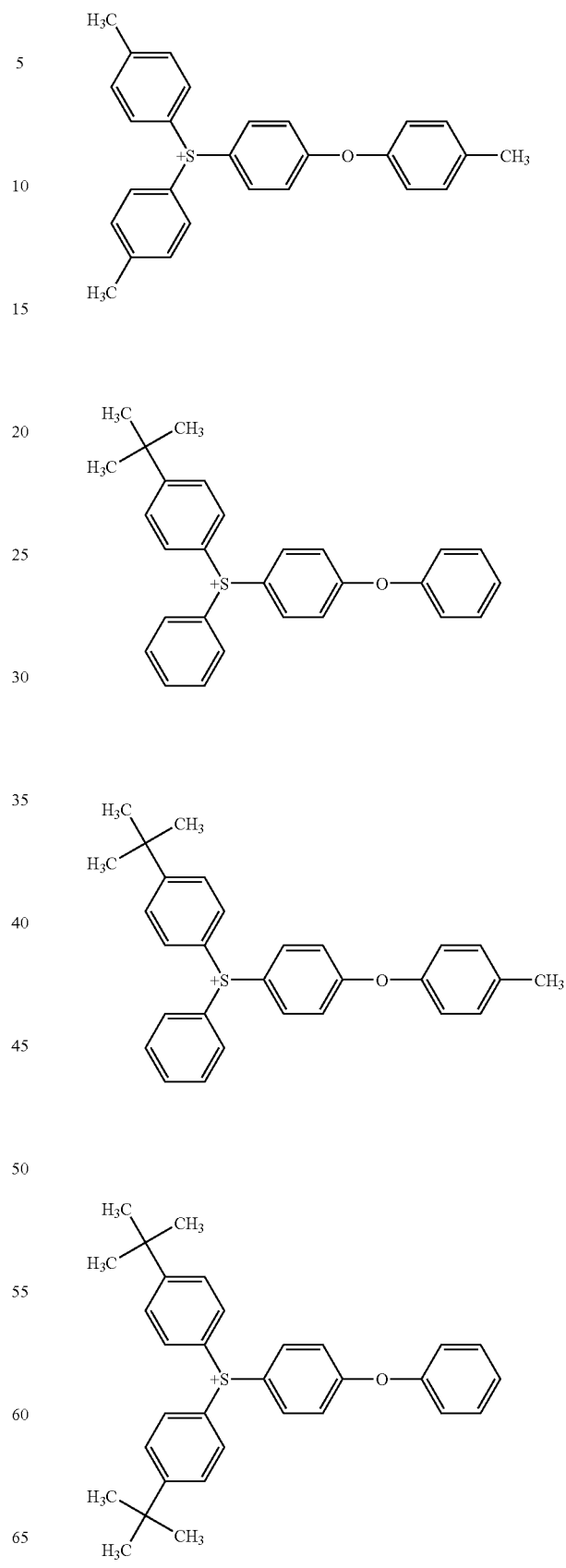

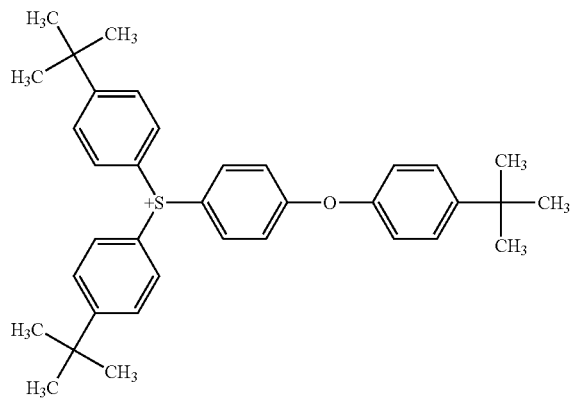
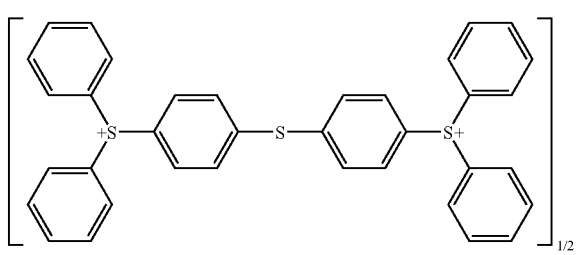
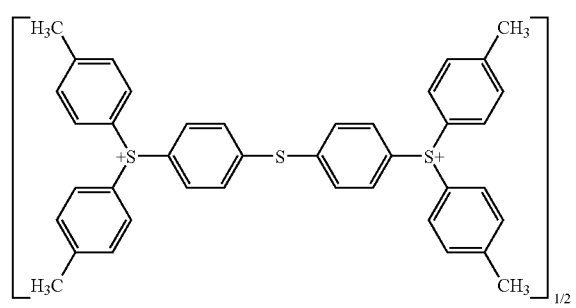
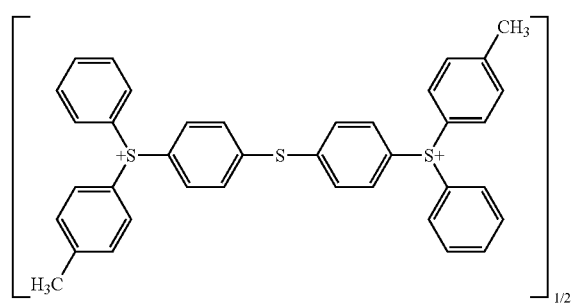
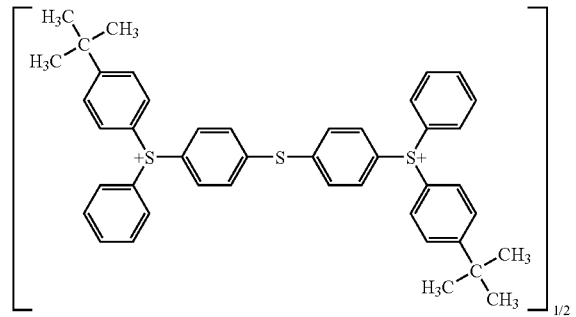
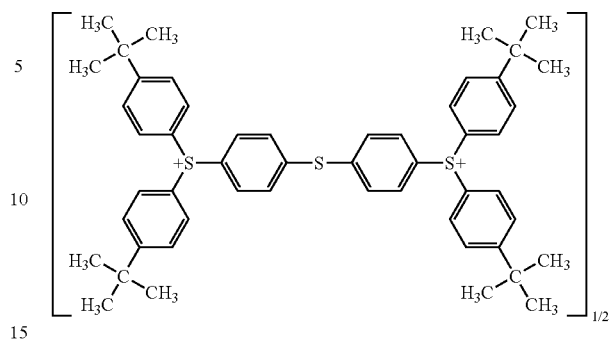
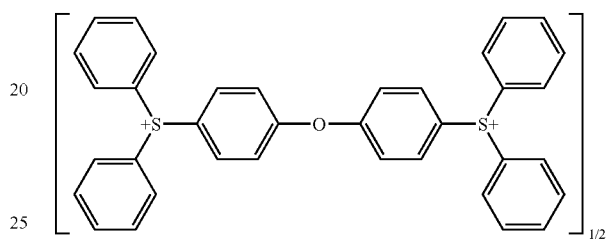
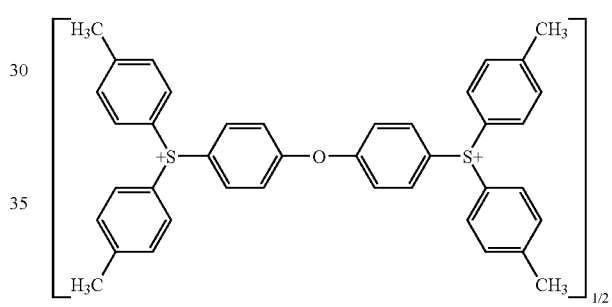
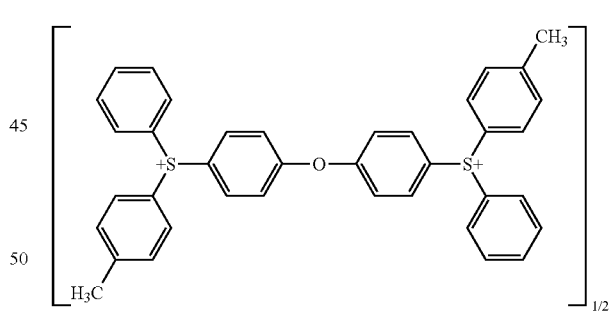
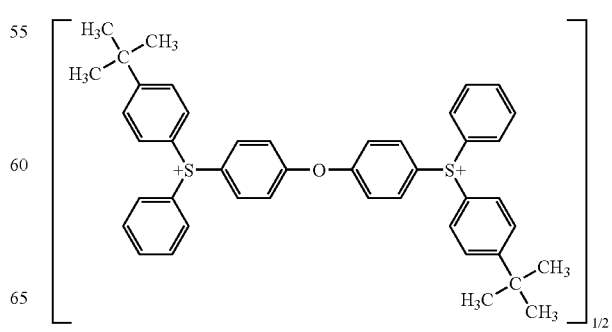

-continued

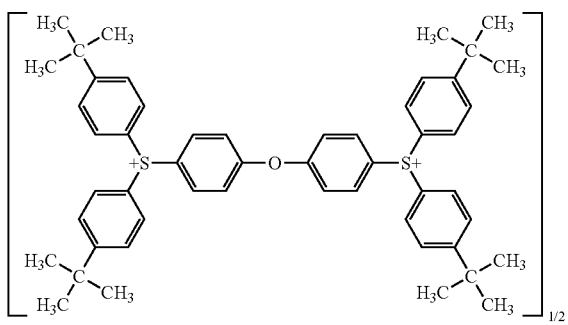

As the organic counter ion, a cation represented by the formula (IIIa), (IIIb) or (IIIc):

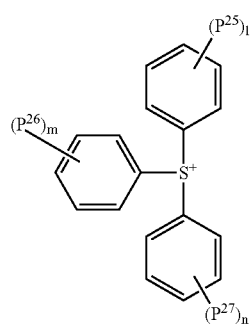

(IIIa)

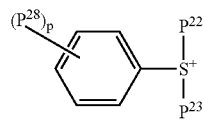

(IIIb)

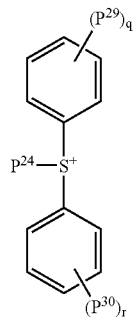

(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be substituted with a hydroxyl group, a C1-C12 alkoxy group or a C3-C12 cyclic hydrocarbon group and wherein at least one hydrogen atom in the C3-C30 cyclic hydrocarbon group may be substituted with a hydroxyl group, a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5, is preferred.

As the organic counter ion, a cation represented by the formula (IIId) or (IIIe):

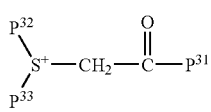

(IIId)

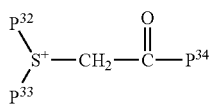

(IIIe)

wherein $P^{31}$ represents an aromatic group which may be substituted, $P^{32}$ and $P^{33}$ are bonded to form a C3-C12 divalent acyclic hydrocarbon group which forms a ring together with the adjacent $S^+$, and at least one —$CH_2$— in the divalent acyclic hydrocarbon group may be replaced with —CO—, —O— or —S—, and $P^{34}$ represents a C1-C12 alkyl group, is also preferred.

As the organic counter ion, a cation represented by the above-mentioned formula (IIIa), (IIIb), (IIIc) or (IIId) is more preferred.

As Salt (I), the salt represented by the formula (IVa), (IVb), (IVc), (IVd) or (IVe):

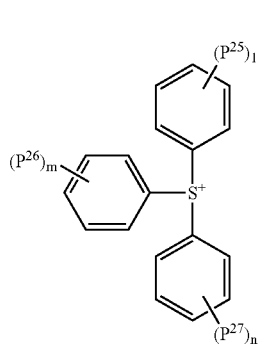 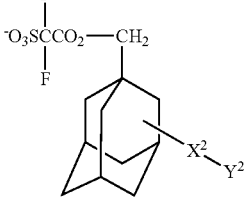

(IVa)

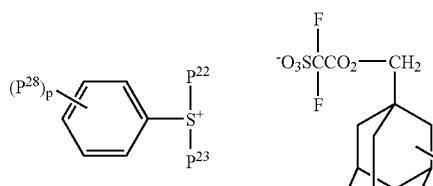

(IVb)

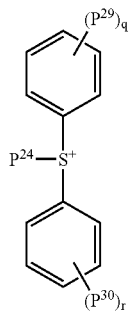 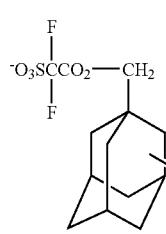

(IVc)

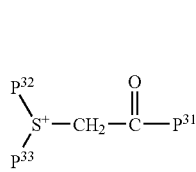
(IVd)
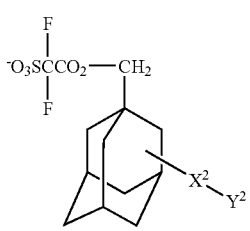
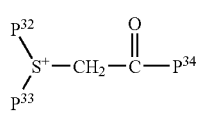
(IVe)
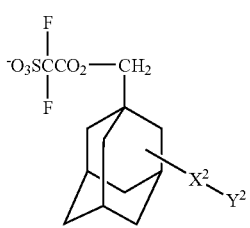
wherein $P^{22}$, $P^{23}$, $P^{24}$, $P^{25}$, $P^{26}$, $P^{27}$, $P^{28}$, $P^{29}$, $P^{30}$, $P^{31}$, $P^{32}$, $P^{33}$, $P^{34}$, l, m, n, p, q, r, $X^2$ and $Y^2$ are the same as defined above, is preferred.
The salt represented by the formula (Va), (Vb), (Vc), (Vd), (Ve), (Vf), (Vg), (Vh), (Vi), or (Vj):
(Va)
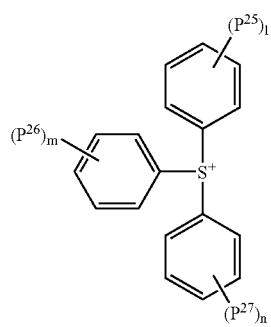
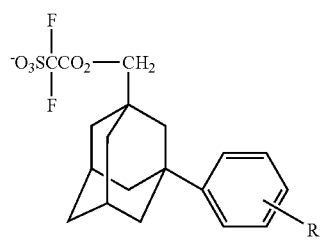
(Vd)
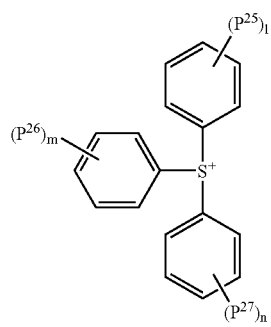
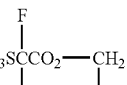
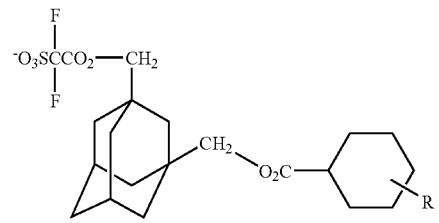
(Vb)
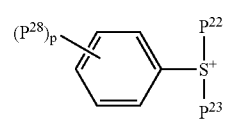
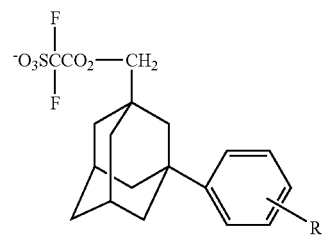
(Ve)
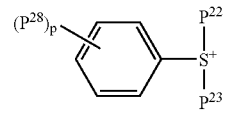
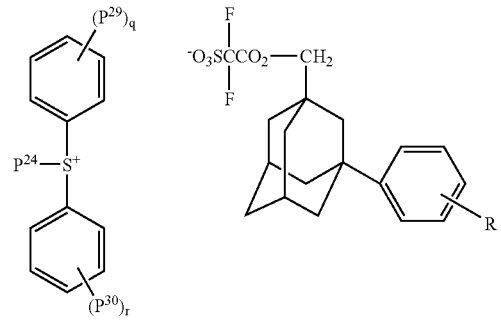
(Vc)
(Vf)
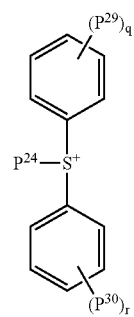

-continued

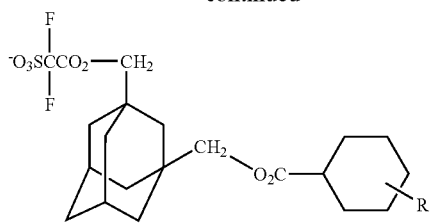

(Vg)

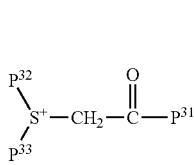 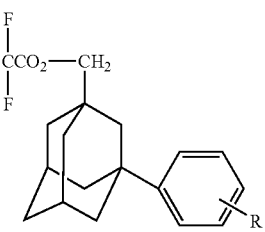

(Vi)

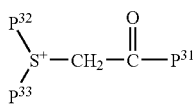

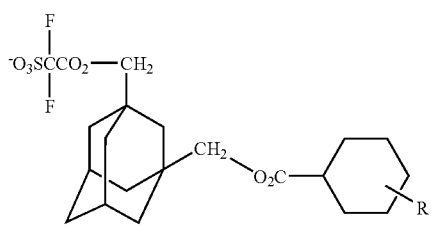

(Vh)

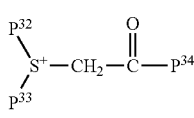 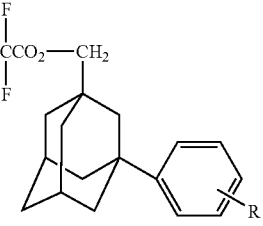

(Vj)

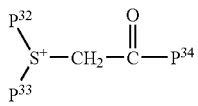

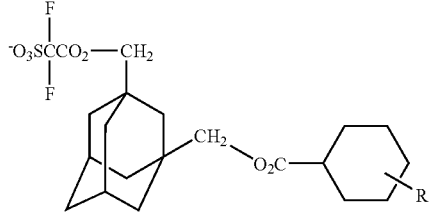

wherein $P^{22}$, $P^{23}$, $P^{24}$, $P^{25}$, $P^{26}$, $P^{27}$, $P^{28}$, $P^{29}$, $P^{30}$, $P^{31}$, $P^{32}$, $P^{33}$, $P^{34}$, l, m, n, p, q, r and R are the same as defined above, is more preferred for providing chemically amplified resist compositions giving patterns having higher resolution.

Examples of the process for production of Salt (I) include a process comprising reacting a salt represented by the formula (VI):

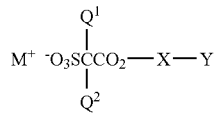

(VI)

wherein X and Y are the same as defined above and $M^+$ represents Li, Na, K or Ag (hereinafter, simply referred to as the salt (VI)), with a compound represented by the formula (XI):

$$A^+Z^-  \quad (XI)$$

wherein $A^+$ is the same as defined above and Z represents F, Cl, Br, I, $BF_4$, $AsF_6$, $SbF_6$, $PF_6$ or $ClO_4$ (hereinafter, simply referred to as the compound (XI)), in an inert solvent such as acetonitrile, water, methanol, chloroform and dichloromethane, at a temperature of 0 to 150° C., preferably of 0 to 100° C.

As the compound (XI), commercially available one is usually used.

The amount of the compound (XI) to be used is usually 0.5 to 2 moles relative to 1 mole of the salt (VI). Salt (I) obtained may be taken out by crystallization or washing with water.

Salt (I) can also be produced by a process which comprises reacting a salt represented by the formula (XII):

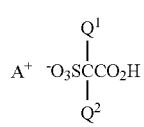

(XII)

wherein $Q^1$, $Q^2$ and $A^+$ are the same as defined above (hereinafter, simply referred to as the salt (XII)), with a compound represented by the formula (VII):

$$HO—X—OH \quad (VII)$$

wherein X is the same as the defined above (hereinafter, simply referred to as the compound (VII)), and a compound represented by the formula (VIII):

$$H—Y \quad (VIII)$$

wherein Y is the same as defined above (hereinafter, simply referred to as the compound (VIII)).

As the compounds (VII) and (VIII), commercially available ones are usually used.

The reaction of the salt (XII), the compound (VII) and the compound (VIII) is usually conducted by mixing them in an aprotic solvent such as dichloroethane, toluene, ethylbenzene, monochlorobenzene, acetonitrile and N,N-dimethylformamide, at 20 to 200° C., preferably 50 to 150° C. in the presence of an acid or a dehydrating agent. Examples of the acid include an organic acid such as p-toluenesulfonic acid and diphenylammonium trifluoromethansulfonate, and an inorganic acid such as sulfuric acid. Examples of the dehydrating agent include 1,1'-carbonyldiimidazole and N,N'-dicyclohexylcarbodiimide.

In the case of using the acid, the reaction is preferably conducted with dehydration, for example, by Dean Stark method as the reaction time tends to be shortened.

The amount of the salt (XII) to be used is usually 0.2 to 3 moles, preferably 0.5 to 2 moles relative to 1 mole of the compound (VII). The amount of the compound (VIII) to be used may be 0.5 to 2 moles relative to 1 mole of the compound (VII) or the amount equivalent to solvent. The amount of the acid to be used may be catalytic amount or the amount equivalent to solvent, and is usually 0.001 to 5 moles relative to 1 mole of the compound (VII). The amount of the dehydrating agent to be used is usually 0.2 to 5 moles, preferably 0.5 to 3 moles relative to 1 mole of the compound (VII).

Salt (I) can also be produced by a process which comprises reacting a salt represented by the formula (XIII):

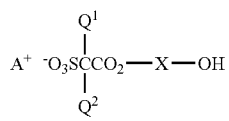
(XIII)

wherein $Q^1$, $Q^2$, $A^+$ and X are the same as defined above (hereinafter, simply referred to as the salt (XIII)), with the compound (VIII).

The salt (XIII) can be produced according to the method described in JP 2006-257078 A1.

The reaction of the salt (XIII) and the compound (VIII) is usually conducted by mixing them in an aprotic solvent such as dichloroethane, toluene, ethylbenzene, monochlorobenzene, acetonitrile and N,N-dimethylformamide, at 20 to 200° C., preferably 50 to 150° C. in the presence of an acid or a dehydrating agent. Examples of the acid include an organic acid such as p-toluenesulfonic acid and diphenylammonium trifluoromethansulfonate, and an inorganic acid such as sulfuric acid. Examples of the dehydrating agent include 1,1'-carbonyldiimidazole and N,N'-dicyclohexylcarbodiimide.

In the case of using the acid, the reaction is preferably conducted with dehydration, for example, by Dean Stark method as the reaction time tends to be shortened.

The amount of the salt (XIII) to be used is usually 0.2 to 3 moles, preferably 0.5 to 2 moles relative to 1 mole of the compound (VIII). The amount of the acid to be used may be catalytic amount or the amount equivalent to solvent, and is usually 0.001 to 5 moles relative to 1 mole of the salt (XIII). The amount of the dehydrating agent to be used is usually 0.2 to 5 moles, preferably 0.5 to 3 moles relative to 1 mole of the salt (XIII).

Examples of the process for production of the salt (VI) include a process comprising reacting a compound represented by the formula (IX):

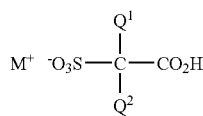
(IX)

wherein $Q^1$, $Q^2$ and M are the same as defined above (hereinafter, simply referred to as the compound (IX)), with the compound (VII) and the compound (VIII).

The reaction of the compound (IX), the compound (VII) and the compound (VIII) is usually conducted by mixing them in an aprotic solvent such as dichloroethane, toluene, ethylbenzene, monochlorobenzene, acetonitrile and N,N-dimethylformamide, at 20 to 200° C., preferably 50 to 150° C. in the presence of an acid or a dehydrating agent. Examples of the acid include an organic acid such as p-toluenesulfonic acid and diphenylammonium trifluoromethanesulfonate, and an inorganic acid such as sulfuric acid. Examples of the dehydrating agent include 1,1'-carbonyldiimidazole and N,N'-dicyclohexylcarbodiimide.

In the case of using the acid, the reaction is preferably conducted with dehydration, for example, by Dean Stark method as the reaction time tends to be shortened.

The amount of the compound (IX) to be used is usually 0.2 to 3 moles, preferably 0.5 to 2 moles relative to 1 mole of the compound (VII). The amount of the compound (VIII) to be used may be 0.5 to 2 moles relative to 1 mole of the compound (VII) or the amount equivalent to solvent. The amount of the acid to be used may be catalytic amount or the amount equivalent to solvent, and is usually 0.001 to 5 moles relative to 1 mole of the compound (VII). The amount of the dehydrating agent to be used is usually 0.2 to 5 moles, preferably 0.5 to 3 moles relative to 1 mole of the compound (VII).

The salt (VI) can also be produced by a reaction of the compound (IX) with a compound represented by the formula (X):

HO—X—Y (X)

wherein X and Y are the same as defined above (hereinafter, simply referred to as the compound (X)).

The reaction of the compound (IX) and the compound (X) is usually conducted by mixing both in the above-mentioned aprotic solvent, at 20 to 200° C., preferably 50 to 150° C.

The reaction is usually conducted in the presence of the above-mentioned acid or the above-mentioned dehydrating agent.

The reaction is preferably conducted while removing the alcohol compound generated, for example, by Dean Stark method as the reaction time tends to be shortened.

The amount of the salt (IX) is usually 0.2 to 3 moles, preferably 0.5 to 2 moles relative to 1 mole of the compound (X).

The amount of the acid to be used may be a catalytic amount or the amount equivalent to solvent, and is usually 0.001 to 5 moles relative to 1 mole of the compound (X). The amount of the dehydrating agent to be used is usually 0.2 to 5 moles, preferably 0.5 to 3 moles relative to 1 mole of the compound (X).

The salt (XII) can be produced by a process which comprises reacting the compound (IX) with the compound (XI). The process is usually conducted in an inert solvent such as water, acetonitrile, chloroform and dichloromethane, at a temperature of 0 to 100° C., preferably of 0 to 60° C. The amount of the compound (XI) is usually 0.5 to 2 moles relative to 1 mole of the compound (IX).

Next, the present chemically amplified positive resist composition will be illustrated.

The present chemically amplified positive resist composition comprises Salt (I) and a resin containing a structural unit which has an acid-labile group and which itself is insoluble or poorly soluble in an aqueous alkali solution but becomes soluble in an aqueous alkali solution by the action of an acid.

Salt (I) is usually used as an acid generator, and the acid generated by irradiation to Salt (I) catalytically acts against acid-labile groups in the resin, cleaves acid-labile groups, and the resin becomes soluble in an alkali aqueous solution. Such a composition is suitable for chemically amplified positive resist composition.

The resin used for the present composition contains a structural unit which has the acid-labile group and which itself is insoluble or poorly soluble in an alkali aqueous solution, but the acid-labile group cleave by an acid.

In the present specification, "—COOR" may be described as "a structure having ester of carboxylic acid", and may also be abbreviated as "ester group". Specifically, "—COOC(CH$_3$)$_3$" may be described as "a structure having tert-butyl ester of carboxylic acid", or be abbreviated as "tert-butyl ester group".

Examples of the acid-labile group include a structure having ester of carboxylic acid such as alkyl ester group in which a carbon atom adjacent to the oxygen atom is quaternary carbon atom, alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethyl ester, 1-isopropoxyethyl ester, 1-ethoxypropoxy ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom, such as an isobornyl ester, 1-alkylcycloalkyl ester, 2-alkyl-2-adamantyl ester and 1-(1-adamantyl)-1-alkylalkyl ester group. At least one hydrogen atom in the adamantyl group may be substituted with a hydroxyl group.

Examples of the structural unit include a structure unit derived from an ester of acrylic acid, a structural unit derived from an ester of methacrylic acid, a structural unit derived from an ester of norbornenecarboxylic acid, a structural unit derived from an ester of tricyclodecenecarboxylic acid and a structural unit derived from an ester of tetracyclodecenecarboxylic acid. The structure units derived from the ester of acrylic acid and from the ester of methacrylic acid are preferable.

The resin used for the present composition can be obtained by conducting polymerization reaction of a monomer or monomers having the acid-labile group and an olefinic double bond.

Among the monomers, those having a bulky and acid-labile group such as an alicyclic ester group (e.g. a 2-alkyl-2-adamantyl ester and 1-(1-adamantyl)-1-alkylalkyl ester group), since excellent resolution is obtained when the resin obtained is used in the present composition.

Examples of such monomer containing the bulky and acid-labile group include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate.

Particularly when the 2-alkyl-2-adamantyl acrylate, the 2-alkyl-2-adamantyl methacrylate or the 2-alkyl-2-adamantyl α-chloroacrylate is used as the monomer for the resin component in the present composition, a resist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the present composition, a resist composition having excellent sensitivity and heat resistance tends to be obtained. In the present invention, two or more kinds of monomers having a group or groups dissociated by the action of the acid may be used together, if necessary.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

The resin used for the present composition can also contain other structural unit or units derived from an acid-stable monomer in addition to the above-mentioned structural units having the acid-labile group. Herein, the "structural unit derived from an acid-stable monomer" means "a structural unit not dissociated by an acid generated from Salt (I)".

Examples of such other structural unit derived from the acid-stable monomer include a structural unit derived from a monomer having a free carboxyl group such as acrylic acid and methacrylic acid; a structural unit derived from an aliphatic unsaturated dicarboxylic anhydride such as maleic anhydride and itaconic anhydride; a structural unit derived from 2-norbornene; a structural unit derived from acrylonitrile or methacrylonitrile; a structural unit derived from an alkyl acrylate or an alkyl methacrylate in which a carbon atom adjacent to oxygen atom is secondary or tertiary carbon atom; a structural unit derived from 1-adamantyl acrylate or 1-adamantyl methacrylate; a structural unit derived from styrene monomer such as p-hydroxystyrene and m-hydroxystyrene; a structural unit derived from acryloyloxy-γ-butyrolactone or methacryloyloxy-γ-butyrolactone having a lactone ring which may be substituted with an alkyl group; and the like. Herein, the 1-adamantyloxycarbonyl group is the acid-stable group though the carbon atom adjacent to oxygen atom is the quaternary carbon atom, and the 1-adamantyloxycarbonyl group may be substituted with at least one hydroxyl group.

Specific examples of the structural unit derived from the acid-stable monomer include a structural unit derived from 3-hydroxy-1-adamantyl acrylate;

a structural unit derived from 3-hydroxy-1-adamantyl methacrylate;

a structural unit derived from 3,5-dihydroxy-1-adamantyl acrylate;

a structural unit derived from 3,5-dihydroxy-1-adamantyl methacrylate;

a structural unit derived from α-acryloyloxy-γ-butyrolactone;

a structural unit derived from α-methacryloyloxy-γ-butyrolactone;

a structural unit derived from β-acryloyloxy-γ-butyrolactone;

a structural unit derived from β-methacryloyloxy-γ-butyrolactone;

a structural unit represented by the formula (1):

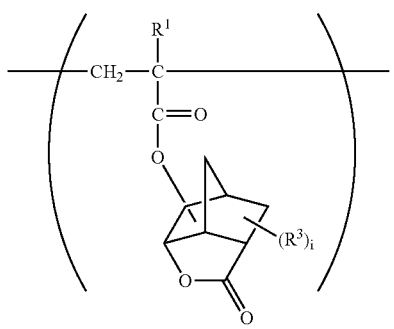

wherein $R^1$ represents a hydrogen atom or a methyl group, $R^3$ represents a methyl group, a trifluoromethyl group or a halogen atom, i represents an integer of 0 to 3, and when p represents 2 or 3, $R^3$s may be the same or different each other;

a structural unit represented by the formula (2):

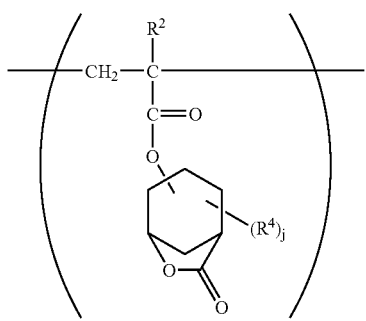

wherein $R^2$ represents a hydrogen atom or a methyl group, $R^4$ represents a methyl group, a trifluoromethyl group or a halogen atom, j represents an integer of 0 to 3, and when q represents 2 or 3, $R^4$s may be the same or different each other;

a structural unit derived from p-hydroxystyrene;

a structural unit derived from m-hydroxystyrene;

a structural unit derived from an alicyclic compound having an olefinic double bond such as a structural unit represented by the formula (3):

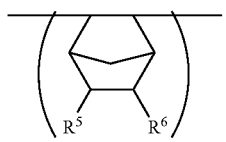

wherein $R^5$ and $R^6$ each independently represents a hydrogen atom, a C1-C3 alkyl group, a C1-C3 hydroxyalkyl group, a carboxyl group, a cyano group, a hydroxyl group or a —COOU group in which U represents an alcohol residue, or $R^5$ and $R^6$ can be bonded together to form a carboxylic anhydride residue represented by —C(═O)OC(═O)—;

a structural unit derived from an aliphatic unsaturated dicarboxylic anhydride such as a structural unit represented by the formula (4):

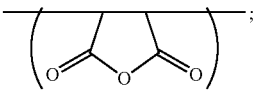

a structural unit represented by the formula (5):

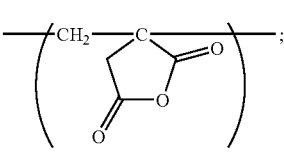

and the like.

Particularly, the resin having further at least one structural unit selected from the structural unit derived from p-hydroxystyrene, the structural unit derived from m-hydroxystyrene, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit represented by the formula (1) and the structural unit represented by the formula (2) in addition to the structural unit having the acid-labile group is preferable from the standpoint of the adhesiveness of resist to a substrate and resolution of resist.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

Further, the acryloyloxy-γ-butyrolactone and the methacryloyloxy-γ-butyrolactone having the lactone ring which may be substituted with the alkyl group can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

As monomers to give structural units represented by the formulae (1) and (2), specifically listed are, for example, an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446

A.

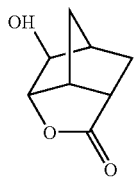 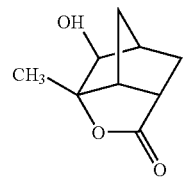 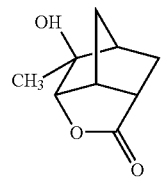

-continued

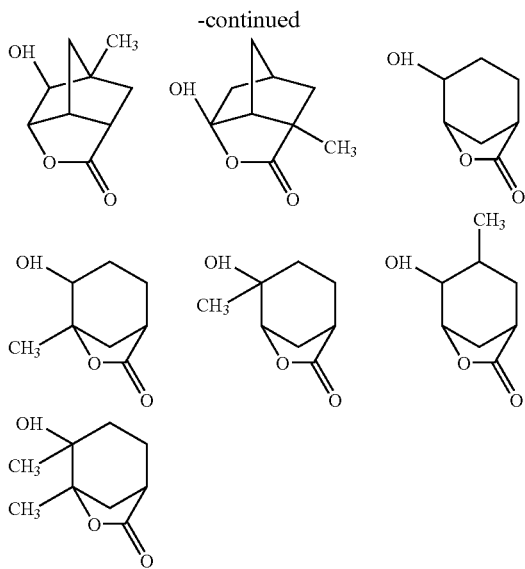

Examples of the acryloyloxy-γ-butyrolactone and the methacryloyloxy-γ-butyrolactone having the lactone ring which may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, α-acryloyloxy-γ-butyrolactone, β-methacryloyloxy-γ-butyrolactone and β-methacryloyloxy-α-methyl-γ-butyrolactone.

The resin containing a structural unit derived from 2-norbornene shows strong structure because the alicyclic group is directly present on its main chain and shows a property that dry etching resistance is excellent. The structural unit derived from 2-norbornene can be introduced into the main chain by radical polymerization using, for example, an aliphatic unsaturated dicarboxylic anhydride such as maleic anhydride and itaconic anhydride together in addition to corresponding 2-norbornene. The structural unit derived from 2-norbornene is formed by opening of its double bond, and can be represented by the above-mentioned formula (3). The structural unit derived from maleic anhydride and from itaconic anhydride which are the structural unit derived from aliphatic unsaturated dicarboxylic anhydrides are formed by opening of their double bonds, and can be represented by the above-mentioned formula (4) and the formula (5), respectively.

In $R^5$ and $R^6$, examples of the C1-C3 alkyl group include a methyl, ethyl, and n-propyl group, and examples of the C1-C3 hydroxyalkyl group include a hydroxymethyl and 2-hydroxyethyl group.

In $R^5$ and $R^6$, the —COOU group is an ester formed from the carboxyl group, and as the alcohol residue corresponding to U, for example, an optionally substituted C1-C8 alkyl group, 2-oxooxolan-3-yl group, 2-oxooxolan-4-yl and the like are listed, and as the substituent on the C1-C8 alkyl group, a hydroxyl group, an alicyclic hydrocarbon residue and the like are listed.

Specific examples of the monomer used to give the structural unit represented by the above-mentioned formula (3) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (3) is a structural unit having the acid-labile group even if it has the norbornane structure. Examples of monomers giving structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, and the like.

The resin used in the present composition preferably contains the structural unit or units having the acid-labile group generally in a ratio of 10 to 80% by mole in all structural units of the resin though the ratio varies depending on the kind of radiation for patterning exposure, the kind of the acid-labile group, and the like.

When the structural units particularly derived from the 2-alkyl-2-adamantyl acrylate, the 2-alkyl-2-adamantyl methacrylate, the 1-(1-adamantyl)-1-alkylalkyl acrylate or the 1-(1-adamantyl)-1-alkylalkyl methacrylate are used as the structural unit having the acid-labile group, it is advantageous in dry-etching resistance of the resist that the ratio of the structural units is 15% by mole or more in all structural units of the resin.

When, in addition to structural units having the acid-labile group, other structural units having the acid-stable group are contained in the resin, it is preferable that the sum of these structural units is in the range of 20 to 90% by mole based on all structural units of the resin.

In the case of KrF lithography, even in the case of using a structure unit derived from hydroxystyrene such as p-hydroxystyrene and m-hydroxystyrene, as one of components of the resin, a resist composition having sufficient transparency can be obtained. For obtaining such copolymerization resins, the corresponding acrylic or methacrylic ester monomer can be radical-polymerized with acetoxystyrene and styrene, and then the acetoxy group in the structure unit derived from acetoxystyrene can be de-acetylated with an acid.

Specific examples of the structural unit derived from hydroxystyrene include the following structural units represented by the formulae (5) and (6).

(6)

(7)

In the case of KrF lithography, it is preferable that the resin contains at least one structural unit selected from the above-mentioned structural unit represented by the formula (4) and the following structural units represented by the formulae (8) to (20) in addition to at least one structural unit selected from the above-mentioned structural unit represented by the formulae (6) and (7).

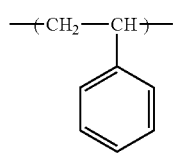
(8)

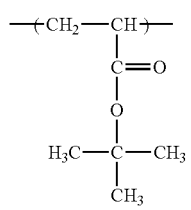
(9)

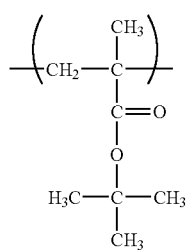
(10)

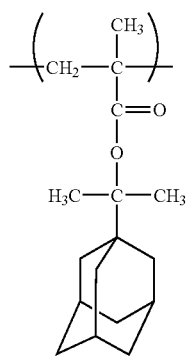
(11)

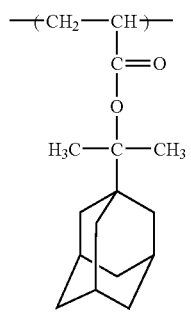
(12)

-continued

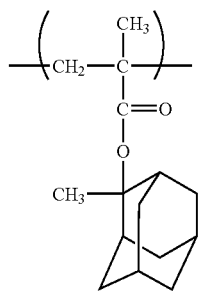
(13)

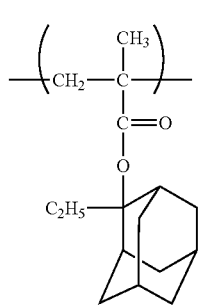
(14)

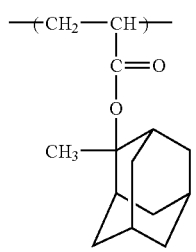
(15)

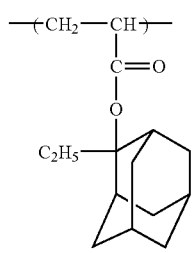
(16)

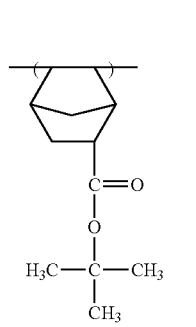
(17)

-continued

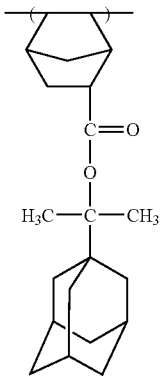

(18)

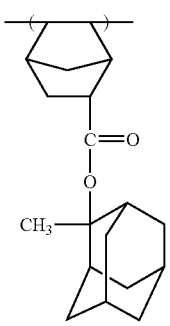

(19)

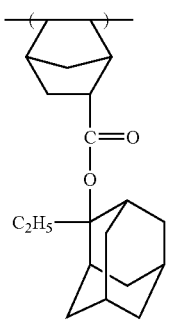

(20)

Specific examples of the resin suitable for the KrF lithography include a resin containing the structural units represented by the formulae (6), (8) and (9), a resin containing the structural units represented by the formulae (6), (7) and (9), a resin containing the structural units represented by the formulae (6), (8) and (10), a resin containing the structural units represented by the formulae (6), (7) and (10), a resin containing the structural units represented by the formulae (6) and (11), a resin containing the structural units represented by the formulae (6) and (12), a resin containing the structural units represented by the formulae (6) and (13), a resin containing the structural units represented by the formulae (6) and (14), a resin containing the structural units represented by the formulae (6) and (15), a resin containing the structural units represented by the formulae (6) and (16), a resin containing the structural units represented by the formulae (6), (8) and (13), a resin containing the structural units represented by the formulae (6), (7) and (13), a resin containing the structural units represented by the formulae (4), (6) and (17), a resin containing the structural units represented by the formulae (4), (6) and (18), a resin containing the structural units represented by the formulae (4), (6) and (19) and a resin containing the structural units represented by the formulae (4), (6) and (20).

In the KrF lithography, the resin having the structural unit having the 2-alkyl-2-adamantyl or 1-(1-adamantyl)-1-alkylalkyl group is preferable as the resin of the resist component in the viewpoint of dry etching resistance.

In the KrF lithography, a resin containing a structural unit which is derived from hydroxystyrene and in which a part of hydroxyl groups are protected with acid-labile groups in addition to the structural unit derived from hydroxystyrene can be also used. Examples of the acid-labile group include the same as described above.

As the resin containing the structural unit which is derived from hydroxystyrene and in which a part of hydroxyl groups in addition to the structural unit derived from hydroxystyrene are protected with acid-labile groups, a resin containing a structural unit represented by the formula (21):

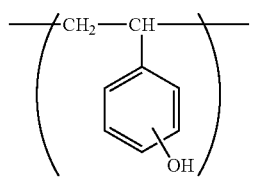

(21)

and a structural unit represented by the formula (22):

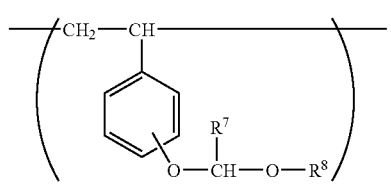

(22)

wherein $R^7$ represents a C1-C4 alkyl group and $R^8$ represents a C1-C6 alkyl group or a C5-C7 cycloalkyl group, or $R^7$ and $R^8$ are bonded with each other to form a trimethylene or tetramethylene group, is preferable and a resin containing a structural unit represented by the formula (23):

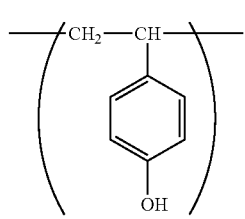

(23)

and a structural unit represented by the formula (24):

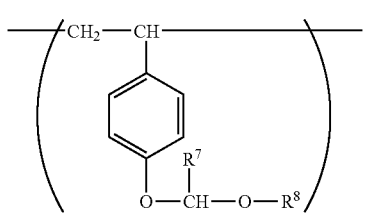
(24)

wherein $R^7$ and $R^8$ are the same as defined above, is more preferable.

Examples of the C1-C4 alkyl group include a methyl, ethyl, n-propyl, isopropyl and n-butyl group, and the ethyl and propyl groups are preferable. Examples of the C1-C6 alkyl group include a methyl, ethyl, n-propyl, isopropyl, n-butyl, n-pentyl and n-hexyl group, and the ethyl and n-propyl groups are preferable. Examples of the C5-C7 cycloalkyl group include a cyclopentyl, cyclohexyl and cycloheptyl group, and the cyclohexyl group is preferable.

The resin used for the present composition can be produced by conducting polymerization reaction of the corresponding monomer or monomers. The resin can be also produced by conducting oligomerization of the corresponding monomer or monomers followed by polymerizing the oligomer obtained.

The polymerization reaction is usually carried out in the presence of a radical initiator.

The radical initiator is not limited and examples thereof include an azo compound such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); an organic hydroperoxide such as lauroyl peroxide, tert-butyl hydroperoxide, benzoyl peroxide, tert-butyl peroxybenzoate, cumene hydroperoxide, diisopropyl peroxydicarbonate, di-n-propyl peroxydicarbonate, tert-butyl peroxyneodecanoate, tert-butyl peroxypivalate and 3,5,5-trimethylhexanoyl peroxide; and an inorganic peroxide such as potassium peroxodisulfate, ammonium peroxodisulfate and hydrogen peroxide. Among them, the azo compound is preferable and 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile) and dimethyl-2,2'-azobis(2-methylpropionate) are more preferable, and 2,2'-azobisisobutyronitrile and 2,2'-azobis(2,4-dimethylvaleronitrile) are especially preferable.

These radical initiators may be used alone or in a form of a mixture of two or more kinds thereof. When the mixture of two or more kinds thereof is used, the mixed ratio is not particularly limited.

The amount of the radical initiator is preferably 1 to 20% by mole based on all monomer or oligomer molar amount.

The polymerization temperature is usually 0 to 150° C., and preferably 40 to 100° C.

The polymerization reaction is usually carried out in the presence of a solvent and it is preferred to use a solvent which is sufficient to dissolve the monomer, the radical initiator and the resin obtained.

Examples thereof include a hydrocarbon solvent such as toluene; an ether solvent such as 1,4-dioxane and tetrahydrofuran; a ketone solvent such as methyl isobutyl ketone; an alcohol solvent such as isopropyl alcohol; a cyclic ester solvent such as γ-butyrolactone; a glycol ether ester solvent such as propylene glycol monomethyl ether acetate; and an acyclic ester solvent such as ethyl lactate. These solvents may be used alone and a mixture thereof may be used.

The amount of the solvent is not limited, and practically, it is preferably 1 to 5 parts by weight relative to 1 part of all monomers or oligomers.

When an alicyclic compound having an olefinic double bond and an aliphatic unsaturated dicarboxylic anhydride are used as monomers, it is preferable to use them in excess amount in view of a tendency that these are not easily polymerized.

After competition of the polymerization reaction, the resin produced can be isolated, for example, by adding a solvent in which the present resin is insoluble or poorly soluble to the reaction mixture obtained and filtering the precipitated resin. If necessary, the isolated resin may be purified, for example, by washing with a suitable solvent.

The present resist composition preferably includes 80 to 99.9% by weight of the resin component and 0.1 to 20% by weight of Salt (I) based on the total amount of the resin component and Salt (I).

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

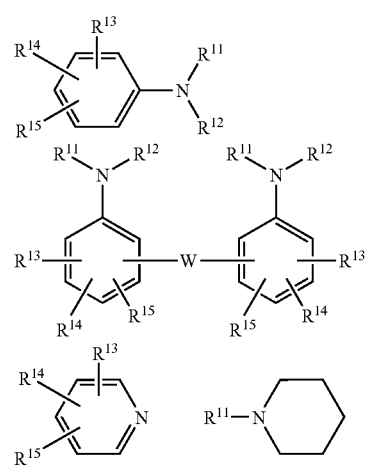

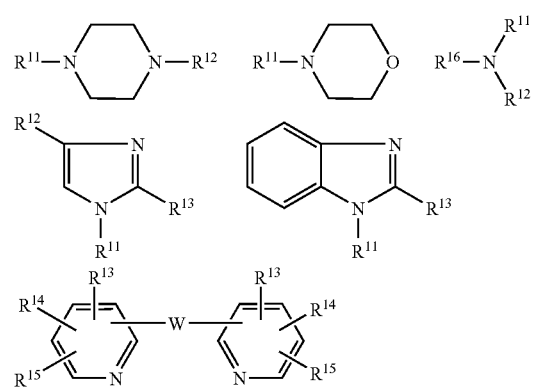

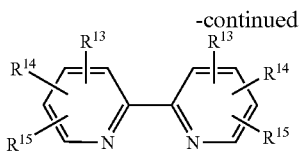

wherein $R^{11}$ and $R^{12}$ independently represent a hydrogen atom, an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, an alkyl group, a cycloalkyl group, an aryl group or an alkoxy group, and the alkyl, cycloalkyl, aryl and alkoxy group may be substituted with at least one group selected from a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, an alkyl group, a cycloalkyl group, an aryl group, an alkoxy group or a nitro group, and the alkyl, cycloalkyl, aryl and alkoxy group which may be substituted with at least one group selected from a hydroxyl group, an amino group which may be substituted with a C1-C4 alkyl group and a C1-C6 alkoxy group, $R^{16}$ represents an alkyl or cycloalkyl group, and the alkyl and cycloalkyl group may be substituted with at least one group selected from a hydroxyl group, an amino group which may be substituted with a C1-C4 alkyl group and a C1-C6 alkoxy group, and W represents —CO—, —NH—, —S—, —S—S—, an alkylene group of which at least one methylene group may be replaced with —O—, or an alkenylene group of which at least one methylene group may be replaced with —O—, and a quaternary ammonium hydroxide represented by the following formula:

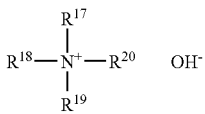

wherein $R^{17}$, $R^{18}$, $R^{19}$ and $R^{20}$ independently represent an alkyl group, a cycloalkyl group or an aryl group, and the alkyl, cycloalkyl and aryl group may be substituted with at least one group selected from a hydroxyl group, an amino group which may be substituted with a C1-C4 alkyl group and a C1-C6 alkoxy group.

The alkyl group in $R^{11}$, $R^{12}$, $R^{13}$, $R^{14}$ $R^{15}$, $R^{16}$, $R^{17}$, $R^{18}$, $R^{19}$ and $R^{20}$ preferably has about 1 to 10 carbon atoms, and more preferably has about 1 to 6 carbon atoms.

Examples of the amino group which may be substituted with the C1-C4 alkyl group include an amino, methylamino, ethylamino, n-butylamino, dimethylamino and diethylamino group. Examples of the C1-C6 alkoxy group which may be substituted with the C1-C6 alkoxy group include a methoxy, ethoxy, n-propoxy, isopropoxy, n-butoxy, tert-butoxy, n-pentyloxy, n-hexyloxy and 2-methoxyethoxy group.

Specific examples of the alkyl group which may be substituted with at least one group selected from a hydroxyl group, an amino group which may be substituted with a C1-C4 alkyl group, and a C1-C6 alkoxy group which may be substituted with a C1-C6 alkoxy group include a methyl, ethyl, n-propyl, isopropyl, n-butyl, tert-butyl, n-pentyl, n-hexyl, n-octyl, n-nonyl, n-decyl, 2-(2-methoxyethoxy)ethyl, 2-hydroxyethyl, 2-hydroxypropyl, 2-aminoethyl, 4-aminobutyl and 6-aminohexyl group.

The cycloalkyl group in $R^{11}$, $R^{12}$, $R^{13}$, $R^{14}$, $R^{15}$, $R^{16}$, $R^{17}$, $R^{18}$, $R^{19}$ and $R^{20}$ preferably has about 5 to 10 carbon atoms. Specific examples of the cycloalkyl group which may be substituted with at least one group selected from a hydroxyl group, an amino group which may be substituted with a C1-C4 alkyl group and a C1-C6 alkoxy group include a cyclopentyl, cyclohexyl, cycloheptyl and cyclooctyl group.

The aryl group in $R^{11}$, $R^{12}$, $R^{13}$, $R^{14}$, $R^{15}$, $R^{16}$, $R^{17}$, $R^{18}$ and $R^{19}$ and $R^{20}$ preferably has about 6 to 10 carbon atoms. Specific examples of the aryl group which may be substituted with at least one group selected from a hydroxyl group, an amino group which may be substituted with a C1-C4 alkyl group and a C1-C6 alkoxy group include a phenyl and naphthyl group.

The alkoxy group in $R^{13}$, $R^{14}$ and $R^{15}$ preferably has about 1 to 6 carbon atoms and specific examples thereof include a methoxy, ethoxy, n-propoxy, isopropoxy, n-butoxy, tert-butoxy, n-pentyloxy and n-hexyloxy group.

The alkylene and alkenylene groups in W preferably have 2 to 6 carbon atoms. Specific examples of the alkylene group include an ethylene, trimethylene, tetramethylene, methylenedioxy and ethylene-1,2-dioxy group, and specific examples of the alkenylene group include an ethane-1,2-diyl, 1-propene-1,3-diyl and 2-butene-1,4-diyl group.

Specific examples of the amine compound include n-hexylamine, n-heptylamine, n-octylamine, n-nonylamine, n-decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecyamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skelton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and Salt (I).

The present resist composition can contain, if necessary, a small amount of various additives such as a sensitizer, a solution suppressing agent, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended claims, and includes all variations of the equivalent meanings and ranges to the claims.

The present invention will be described more specifically by Examples, which are not construed to limit the scope of the present invention. The "%" and "part(s)" used to represent the content of any component and the amount of any material to be used in the following Examples are on a weight basis unless otherwise specifically noted. The weight-average molecular weight of any material in the following Examples is a value found by gel permeation chromatography [HLC-8120GPC Type, Column (Total 3 Columns): TSKgel Multipore HXL-M manufactured by TOSOH CORPORATION, Solvent: tetrahydrofuran] using polystyrene as a standard reference material.

Structures of salts obtained were determined by NMR (GX-270 Type or EX-270 Type, manufactured by JEOL LTD.) and mass spectrometry (Liquid Chromatography: 1100 Type manufactured by AGILENT TECHNOLOGIES LTD., Mass Spectrometry: LC/MSD Type or LC/MSD TOF Type manufactured by AGILENT TECHNOLOGIES LTD.).

Salt Synthesis Example 1

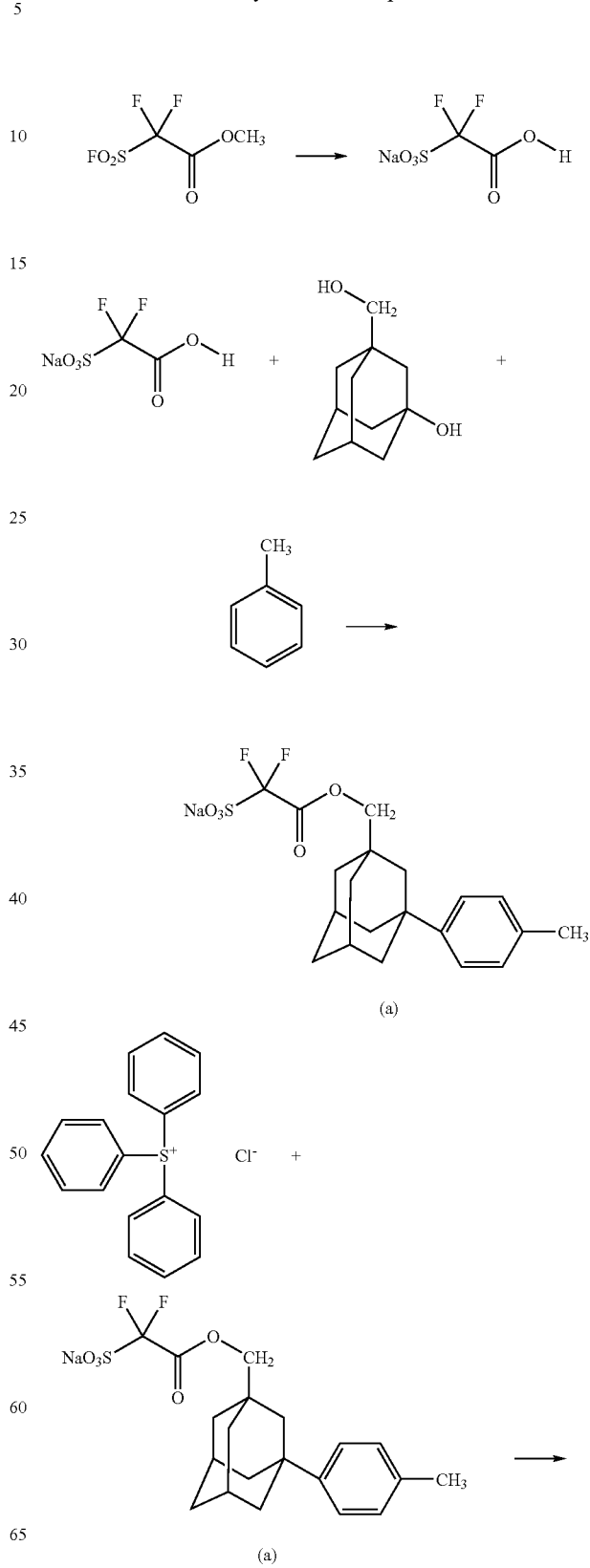

-continued

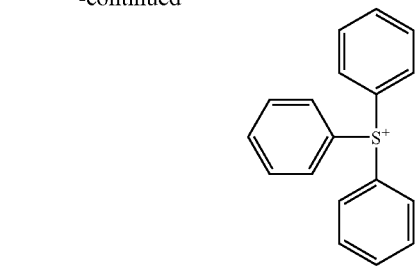

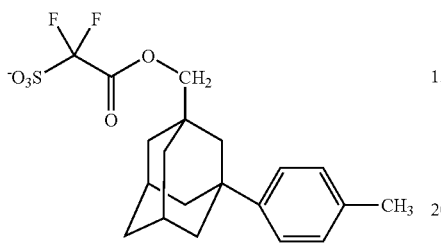

(b)

(1) 25000 Parts of 30% aqueous sodium hydroxide solution was added dropwise into a mixture of 10000 parts of methyl difluoro(fluorosulfonyl)acetate and 15000 parts of ion-exchanged water in an ice bath. The resultant mixture was refluxed at 100° C. for 3 hours and cooled. The mixture was neutralized with 7754 parts of conc. hydrochloric acid. The resultant mixture was concentrated and the residue obtained was mixed with 6000 parts of acetonitrile. The resultant mixture was stirred and filtrated. The filtrate obtained was concentrated and the residue obtained was filtrated. The filtrate obtained was concentrated and the residue obtained was mixed with 200 parts of acetonitrile. The mixture obtained was stirred and filtrated, and the solid obtained was dried to obtain 605 parts of sodium salt of difluorosulfoacetic acid (purity: 97.6%).

(2) 100 Parts of toluene, 10.0 parts of sodium salt of difluorosulfoacetic acid (purity: 97.6%), 8.98 parts of (3-hydroxy-1-adamantyl)methanol and 0.3 part of diphenylammonium trifluoromethanesulfonate were mixed. The mixture obtained was heated and refluxed for 36 hours. The mixture was cooled, and then, concentrated. To the residue obtained, 287 parts of acetonitrile was added, and the mixture obtained was stirred and filtrated. The filtrate obtained was concentrated. To the concentrated liquid obtained, 141 parts of tert-butyl methyl ether was added and the resultant mixture was stirred and filtrated to obtain the solid. The solid obtained was dried to obtain 16.7 parts of the salt represented by the above-mentioned formula (a) in the form of white green solid.

(3) 6.0 Parts of the salt represented by the formula (a) obtained in the above-mentioned (2) was mixed with 90 parts of chloroform. To the mixture obtained, 34.72 parts of aqueous triphenylsulfonium chloride solution (concentration: 14.2%) was added and the resultant mixture was stirred over night. The mixture was separated to obtain the aqueous layer and the organic layer. The organic later obtained was repeated to wash with an ion-exchanged water until the aqueous layer obtained was neutralized. To the organic layer, 1.6 parts of activated carbon was added and the resultant mixture was mixed and filtrated. The filtrate obtained was concentrated. The concentrated liquid obtained and 35 parts of ethyl acetate were mixed and the mixture was filtrated to obtain the solid. The solid obtained was dried to obtain 5.4 parts of the salt represented by the above-mentioned formula (b) in the form of white solid, which is called as B1.

$^1$H-NMR (dimethylsulfoxide-$d_6$, Internal standard: tetramethylsilane): δ (ppm) 1.53-1.80 (m, 12H), 2.10 (s, 2H), 2.24 (s, 3H), 3.90 (s, 2H), 7.08 (d, 2H, J=8.10 Hz), 7.21 (d, 2H, J=8.37 Hz), 7.74-7.89 (m, 15H) MS (ESI(+) Spectrum): $M^+$ 263.0 ($C_{18}H_{15}S^+$=263.09) MS (ESI(−) Spectrum): $M^-$ 413.2 ($C_{20}H_{23}F_2O_5S^{2-}$=413.12)

Salt Synthesis Example 2

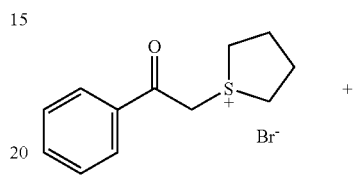

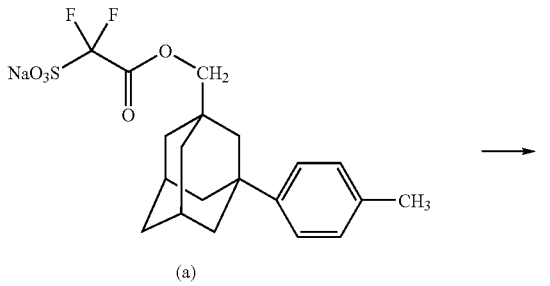

(a)

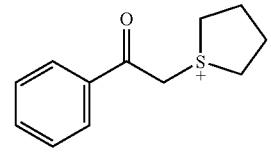

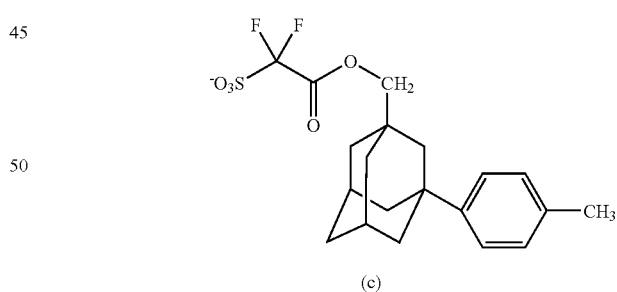

(c)

2.2 Parts of 1-(2-oxo-2-phenylethyl)tetrahydrothiophenium bromide was added to the mixture of 3.0 Parts of the salt represented by the formula (a), 9 parts of chloroform and 8 parts of ion-exchanged water. The resultant mixture was stirred at room temperature over night. 6 Parts of chloroform was added to the reaction mixture and repeated to wash with an ion-exchanged water until the aqueous layer obtained was neutralized. 0.5 Part of activated carbon was added to the organic layer obtained and then stirred. The mixture was filtrated and the filtrate obtained was concentrated. To the residue obtained, 18 parts of tert-butyl methyl ether was added and the resultant mixture was stirred and allowed to stand. The supernatant liquid was removed from the mixture by decantation to obtain the residue. To the residue, 18 parts of n-heptane was added and the resultant mixture was stirred and allowed to stand. The supernatant liquid was removed from the mixture by decantation to obtain 2.5 parts of the salt represented by the above-mentioned formula (c) in the form of orange oil, which is called as B2.

$^1$H-NMR (dimethylsulfoxide-$d_6$, Internal standard: tetramethylsilane): δ (ppm) 1.54-1.80 (m, 12H), 2.10-2.28 (m, 9H), 3.47-3.61 (m, 4H), 3.98 (s, 2H), 5.30 (s, 2H), 7.08 (d, 2H, J=8.10 Hz), 7.21 (d, 2H, J=8.37 Hz), 7.62 (t, 2H, J=7.3 Hz), 7.76 (t, 1H, J=7.3 Hz), 8.00 (dd, 2H, J=1.4 Hz, 7.3 Hz) MS (ESI(+) Spectrum): M$^+$ 207.1 ($C_{12}H_{15}OS^+$=207.08) MS (ESI(−) Spectrum): M$^-$ 413.1 ($C_{20}H_{23}F_2O_5S^-$=413.12)

Salt Synthesis Example 3

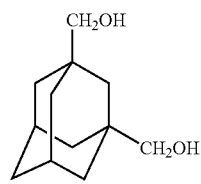
+
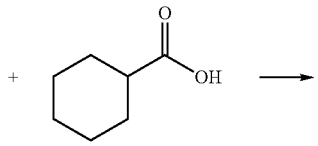
→
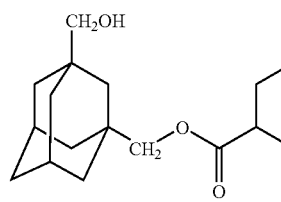

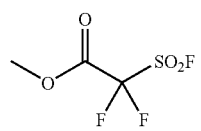  →

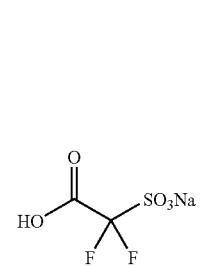 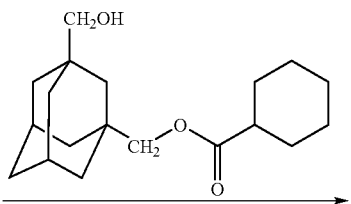 →

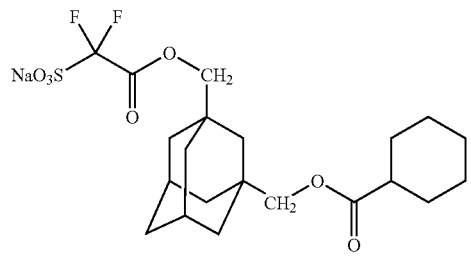

(d)

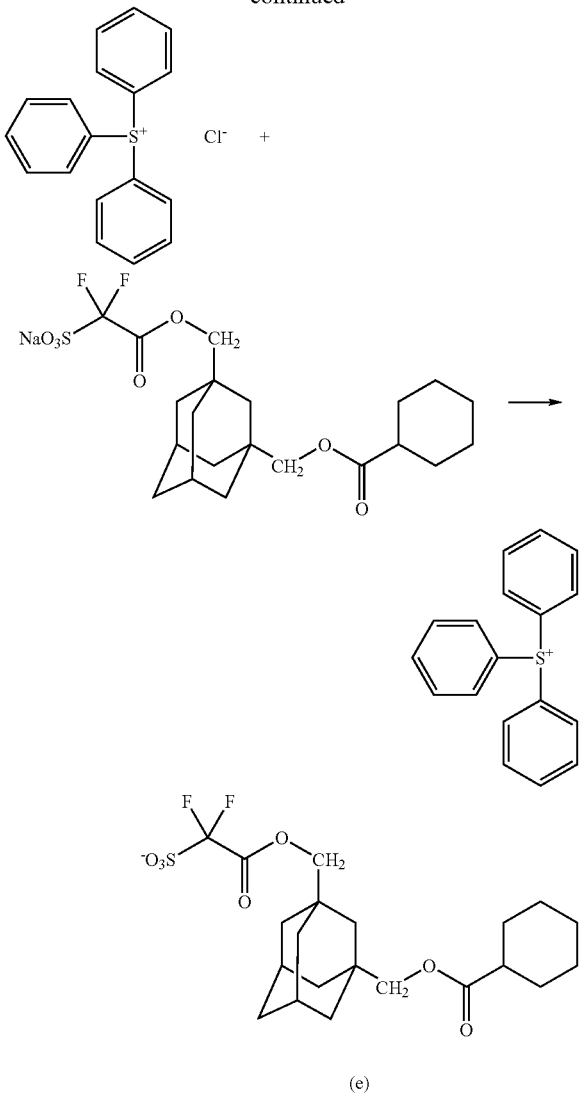

(e)

(1) Two drops of sulfuric acid was added using the pipette to the mixture of 1.9 parts of cyclohexanecarboxylic acid, 5.8 parts of 1,3-adamantanedimethanol and 116 parts of toluene. The resultant mixture was heated and refluxed for 8 hours. The reaction mixture was mixed with 100 parts of 1N aqueous sodium hydroxide solution and then the resultant mixture was repeated to wash with an ion-exchanged water until the aqueous layer obtained was neutralized. The organic layer obtained was mixed with 50 parts of 1N aqueous sodium hydroxide solution and then the resultant mixture was repeated to wash with an ion-exchanged water until the aqueous layer obtained was neutralized. The organic layer obtained was concentrated. The concentrated liquid obtained was purified with column chromatography to obtain 3.7 parts of [3-(hydroxymethyl)-1-adamantyl] methyl cyclohexanecarboxylate.

(2) 230 Parts of 30% aqueous sodium hydroxide solution was added dropwise into a mixture of 100 parts of methyl difluoro(fluorosulfonyl)acetate and 250 parts of ion-exchanged water in an ice bath. The resultant mixture was heated and refluxed at 100° C. for 2.5 hours. After cooling, the reaction mixture was neutralized with 88 parts of conc. hydrochloric acid. The resultant solution obtained was concentrated to obtain 158.4 parts of sodium salt of difluorosulfoacetic acid (in which the inorganic salt was contained, purity: 65.1%).

(3) 2.3 Parts of p-toluenesulfonic acid was added to the mixture of 63 parts of dichloroethane, 3.6 parts of sodium salt of difluorosulfoacetic acid (purity: 65.1%) and 3.7 parts of [3-(hydroxymethyl)-1-adamantyl]methyl cyclohexanecarboxylate, and the resultant mixture was heated and refluxed for 6 hours. The reaction mixture was concentrated to remove dichloroethane and 100 parts of acetonitrile was added to the residue obtained. The resultant mixture was stirred and filtrated. The filtrate obtained was concentrated to obtain 4.9 parts of the salt represented by the above-mentioned formula (d).

(4) 4.9 Parts of the salt represented by the above-mentioned formula (d) obtained in the above-mentioned (3) was dissolved in 49 parts of acetonitrile. The solution obtained by mixing 3.0 parts of triphenylsulfonium chloride and 30 parts of ion-exchanged water was added to the solution obtained. The resultant mixture was stirred for 15 hours. The mixture was concentrated and the residue was extracted twice with 50 parts of chloroform. The organic layers obtained were mixed to wash with an ion-exchanged water until the aqueous layer obtained was neutralized. The organic layer obtained was concentrated. The residue obtained was mixed with 50 parts of tert-butyl methyl ether. The resultant mixture was stirred, and then, decantation was conducted to obtain 3.2 parts of the salt represented by the above-mentioned formula (e) in the form of pale yellow oil, which is called as B3.

$^1$H-NMR (dimethylsulfoxide-$d_6$, Internal standard: tetramethylsilane): δ (ppm) 1.21-1.67 (m, 20H), 1.81-1.85 (m, 2H), 2.02 (br, 2H), 2.27-2.37 (m, 1H), 3.64 (s, 2H), 3.86 (s, 2H), 7.75-7.90 (m, 15H) MS (ESI(+) Spectrum): M$^+$ 263.0 ($C_{18}H_{15}S^+$=263.09) MS (ESI(-) Spectrum): M$^-$ 463.2 ($C_{21}H_{29}F_2O_7S^-$=463.16)

Salt Synthesis Example 4

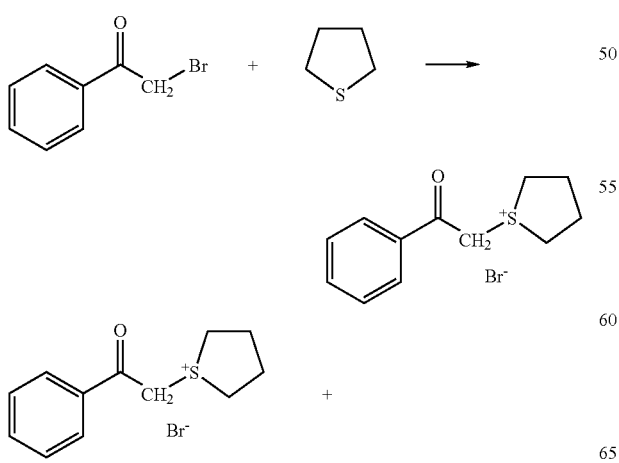

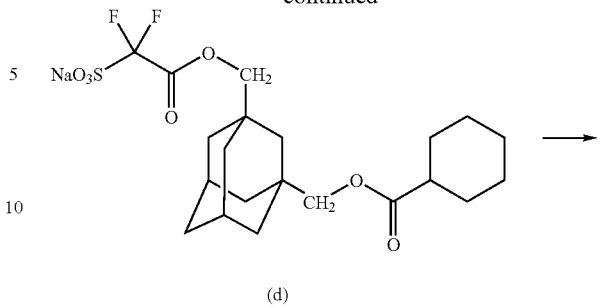

(d)

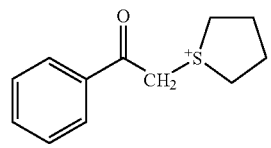

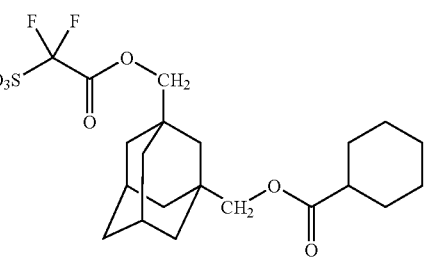

(f)

(1) 150 Parts of 2-bromoacetophenone was dissolved in 375 parts of acetone and 66.5 parts of tetrahydrothiophene was added dropwise to the solution obtained. The resultant mixture was stirred at room temperature for 24 hours and the white precipitates were filtrated, washed, and dried to obtain 207.9 parts of 1-(2-oxo-2-phenylethyl)tetrahydrothiophenium bromide in the form of white crystals.

$^1$H-NMR (dimethylsulfoxide-$d_6$, Internal standard: tetramethylsilane): δ (ppm) 2.13-2.36 (m, 4H), 3.50-3.67 (m, 4H), 5.41 (s, 2H), 7.63 (t, 2H), 7.78 (t, 1H), 8.02 (d, 2H)

(2) 3.6 Parts of the salt represented by the formula (d), which was synthesized in a similar manner to the method described in the above-mentioned Salt Synthesis Example 3 (3), was dissolved in 18 parts of acetonitrile. To the solution obtained, the solution obtained by mixing 2.1 parts of 1-(2-oxo-2-phenylethyl)tetrahydrothiophenium bromide obtained in the above-mentioned (1) with 11 parts of an ion-exchanged water was added. The resultant mixture was stirred for 15 hours and concentrated. The residue obtained was extracted twice with 50 parts of chloroform. The organic layers obtained were mixed and repeated to wash with an ion-exchanged water until the aqueous layer obtained was neutralized. The organic layer obtained was concentrated and the concentrated liquid was mixed with 50 parts of tert-butylmethylether. The resultant mixture was stirred and filtrated to obtain the solid and the solid obtained was dried under reduced pressure condition to obtain 4.0 part of the salt represented by the above-mentioned formula (f) in the form of white solid, which is called as B4.

$^1$H-NMR (dimethylsulfoxide-d$_6$, Internal standard: tetramethylsilane): δ (ppm) 1.22-1.67 (m, 20H), 1.81-1.85 (m, 2H), 2.02 (br, 2H), 2.16-2.37 (m, 5H), 3.46-3.62 (m, 4H), 3.64 (s, 2H), 5.31 (s, 2H), 7.63 (t, 2H), 7.78 (t, 1H), 8.01 (d, 2H) MS (ESI(+) Spectrum): M$^+$ 207.2 (C$_{12}$H$_{15}$OS$^+$=207.08) MS (ESI(−) Spectrum): M$^−$ 463.2 (C$_{21}$H$_{29}$F$_2$O$_7$S$^−$=463.16)

Salt Synthesis Example 5

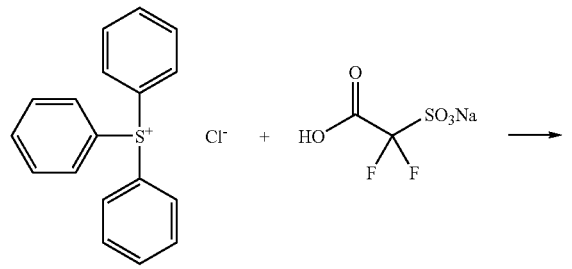

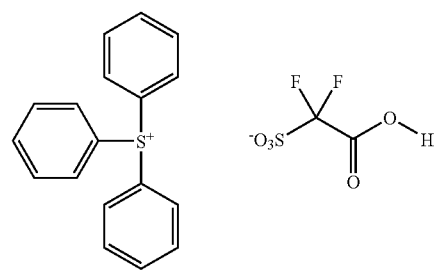

(g)

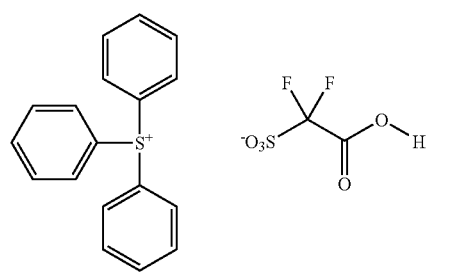

(g)

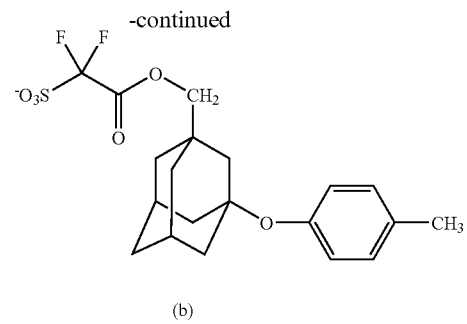

(b)

(1) 300.0 Parts of 18% aqueous sodium salt of difluorosulfoacetic acid solution was added to 573.7 parts of 14.2% aqueous triphenylsulfonium chloride solution and the resultant mixture was stirred at 25° C. for about 20 hours. The white precipitates were filtrated, washed with 100 parts of ion-exchanged water and dried to obtain 88.4 parts of the salt represented by the above-mentioned formula (g).

$^1$H-NMR (dimethylsulfoxide-d$_6$, Internal standard: tetramethylsilane): δ (ppm) 7.77-7.88 (m, 15H), 13.90 (br, 1H) MS (ESI(+) Spectrum): M$^{30}$ 263.2 (C$_{18}$H$_{15}$S$^+$=263.09) MS (ESI(−) Spectrum): M$^−$ 175.0 (C$_2$HF$_2$O$_5$S$^−$=174.95)

(2) 5.0 Parts of the salt represented by the formula (g), 2.1 parts of (3-hydroxy-1-adamantyl)methanol, 50 parts of toluene and 0.3 part of concentrated sulfuric acid were mixed. The mixture obtained was heated and refluxed for 22 hours. The mixture was cooled, and then, concentrated. To the residue obtained, 90 parts of chloroform was added, and the solution obtained was repeated to wash with an ion-exchanged water until the aqueous layer obtained was neutralized. The organic layer obtained was concentrated and the residue obtained was mixed with 49 parts of ethyl acetate. The resultant mixture was stirred and filtrated to obtain the solid. The solid obtained was dried to obtain 5.4 parts of the salt represented by the above-mentioned formula (b). The $^1$H-NMR spectrum of the salt obtained was the same as that of the salt obtained in above-mentioned Salt Synthesis Example 1.

Salt Synthesis Example 6

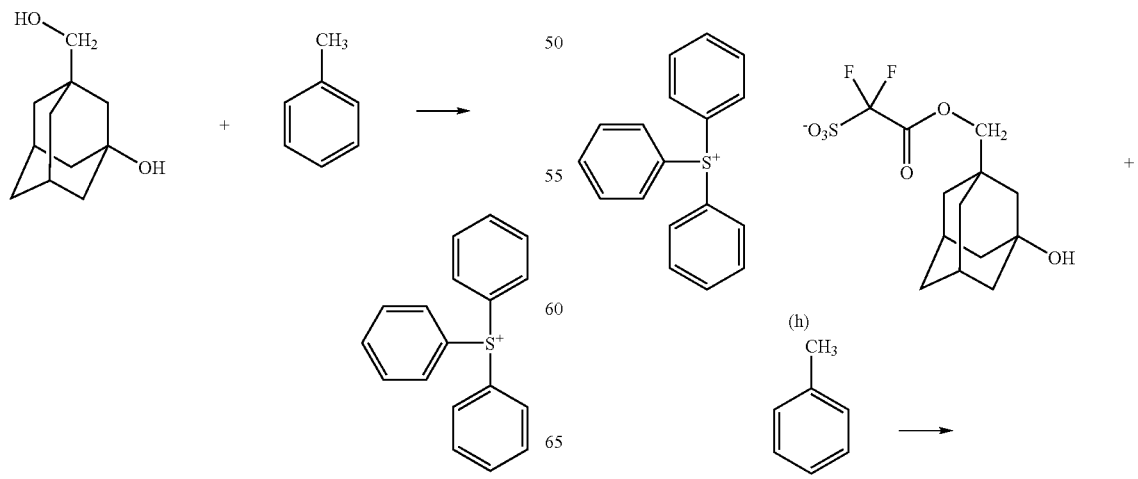

(h)

-continued

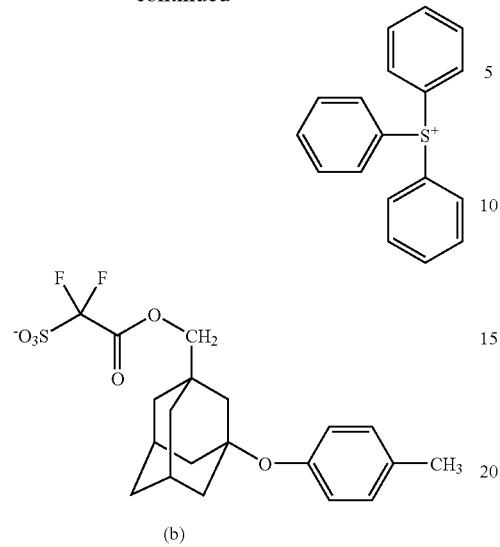

(b)

(1) 50 Parts of the salt represented by the above-mentioned formula (h), which was synthesized in a similar manner to the method described in JP 2006-257078 A1, 250 parts of toluene and 2.4 parts of concentrated sulfuric acid were mixed. The mixture obtained was heated and refluxed for 7 hours. The mixture was cooled, and then, concentrated. To the residue obtained, 326 parts of chloroform was added, and the solution obtained was repeated to wash with an ion-exchanged water until the aqueous layer obtained was neutralized. The organic layer obtained was mixed with 4.5 parts of activated carbon. The mixture obtained was stirred and filtrated. The filtrate obtained was concentrated and the residue obtained was mixed with 260 parts of ethyl acetate. The resultant mixture was stirred and filtrated to obtain the solid. The solid obtained was dried to obtain 39.3 parts of the salt represented by the above-mentioned formula (b).

The $^1$H-NMR spectrum of the salt obtained was the same as that of the salt obtained in above-mentioned Salt Synthesis Example 1.

Comparative Salt Synthesis Example 1

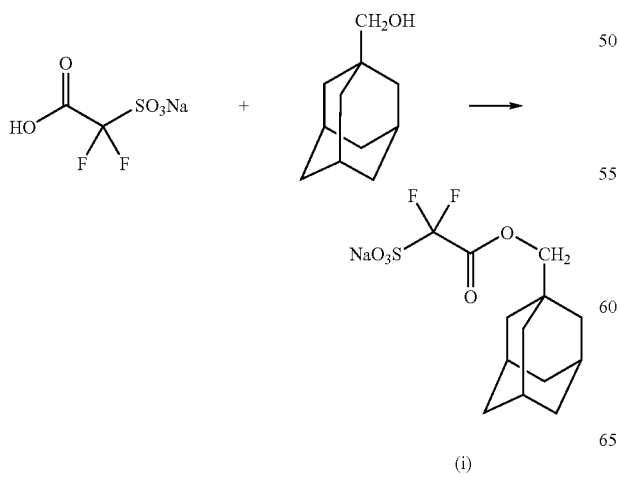

(i)

-continued

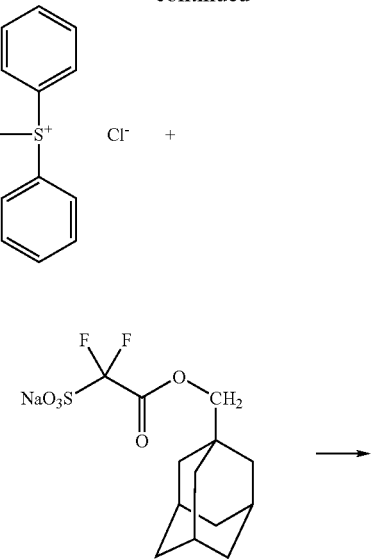

(i)

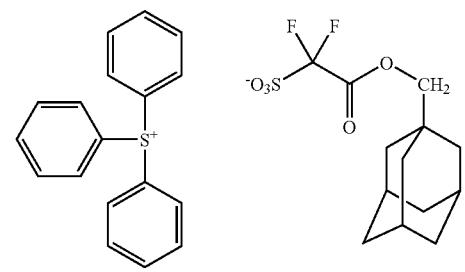

(j)

(1) 24.0 Parts of p-toluenesulfonic acid was added to a mixture of 39.4 Parts of sodium salt of difluorosulfoacetic acid (purity: 63.5%), 21.0 parts of 1-adamantanemethanol and 200 parts of dichloroethane, and the resultant mixture was heated and refluxed for 7 hours. The mixture was concentrated to remove dichloroethane and 250 parts of tert-butyl methyl ether was added to the residue obtained. The mixture obtained was stirred and filtrated to obtain the solid. To the solid, 250 parts of acetonitrile was added and the resultant mixture was stirred and filtrated. The filtrate obtained was concentrated to obtain 32.8 parts of the salt represented by the above-mentioned formula (i).

(2) 32.8 Parts of the salt obtained in the above-mentioned (1) was dissolved in 100 parts of an ion-exchanged water. To the solution obtained, a mixture of 28.3 parts of triphenylsulfonium chloride and 140 parts of methanol was added to stir for 15 hours. The resultant mixture was concentrated. The concentrated liquid obtained was extracted twice with 200 parts of chloroform. The organic layers obtained were mixed and repeated to wash with an ion-exchanged water until the aqueous layer obtained was neutralized. The organic layer obtained was concentrated. To the concentrated liquid, 300 parts of tert-butyl methyl ether was added and stirred. The resultant mixture was filtrated and the solid obtained was dried to obtain 39.7 parts of the salt represented by the above-mentioned formula (j) in the form of white solid, which is called as Cl.

$^{1}$H-NMR (dimethylsulfoxide-d$_{6}$, Internal standard: tetramethylsilane): δ (ppm) 1.52 (d, 6H), 1.63 (dd, 6H), 1.93 (s, 3H), 3.81 (s, 2H), 7.76-7.90 (m, 15H) MS (ESI(+) Spectrum): M$^{+}$ 263.2 (C$_{18}$H$_{15}$S$^{+}$=263.09) MS (ESI(-) Spectrum): M$^{-}$ 323.0 (C$_{13}$H$_{17}$F$_{2}$O$_{5}$S$^{-}$=323.08)

Comparative Salt Synthesis Example 2

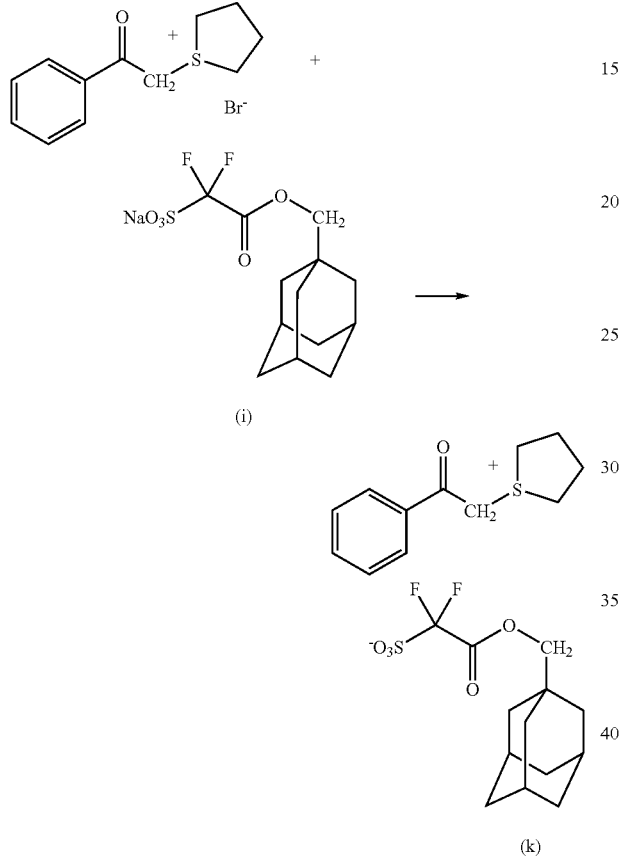

(1) 99.5 Parts of the salt represented by the above-mentioned formula (i) was dissolved in 298 parts of acetonitrile. To the solution obtained, 79.4 parts of 1-(2-oxo-2-phenylethyl) tetrahydrothiophenium bromide and 159 parts of an ion-exchanged water were added and the resultant mixture was stirred for 15 hours. The mixture was concentrated and the residue was extracted twice with 500 parts of chloroform. The organic layers obtained were mixed and repeated to wash with an ion-exchanged water until the aqueous layer obtained was neutralized. The organic layer obtained was concentrated and the residue obtained was mixed with 250 parts of tert-butyl methyl ether. The resultant mixture was stirred and filtrated to obtain the salt represented by the above-mentioned formula (κ) in the form of white solid, which is called as C3.

$^{1}$H-NMR (dimethylsulfoxide-d$_{6}$, Internal standard: tetramethylsilane): δ (ppm) 1.50 (d, 6H), 1.62 (dd, 6H), 1.92 (s, 3H), 2.13-2.32 (m, 4H), 3.45-3.63 (m, 4H), 3.80 (s, 2H), 5.30 (s, 2H), 7.62 (t, 2H), 7.76 (t, 1H), 8.00 (d, 2H) MS (ESI(+) Spectrum): M$^{+}$ 207.0 (C$_{12}$H$_{15}$OS$^{+}$=207.08) MS (ESI(-) Spectrum): M$^{-}$ 323.0 (C$_{13}$H$_{17}$F$_{2}$O$_{5}$S$^{-}$=323.08)

Resin Synthesis Example 1

Monomers used in this Resin Synthesis Example are following monomers M1, M2 and M3.

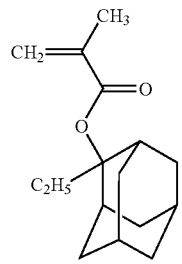

M1

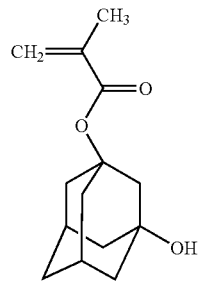

M2

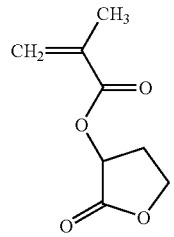

M3

The monomer M1, monomer M2 and monomer M3 were dissolved in 2 times amount of methyl isobutyl ketone as much as the amount of all monomers to be used (monomer molar ratio; monomer M1: monomer M2: monomer M3=5: 2.5:2.5). To the solution, 2,2'-azobisisobutyronitrile was added as an initiator in a ratio of 2 mol % based on all monomer molar amount, and the resultant mixture was heated at 80° C. for about 8 hours. The reaction solution was poured into large amount of heptane to cause precipitation. The precipitate was isolated and washed twice with large amount of heptane for purification. As a result, copolymer having a weight-average molecular weight of about 9,200 was obtained. This copolymer had the following structural units. This is called as resin R1.

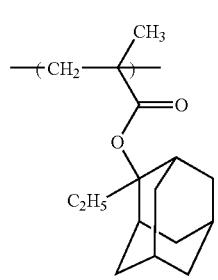 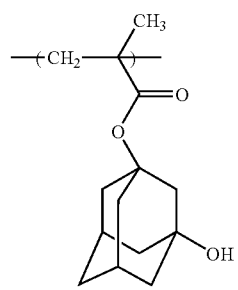

-continued

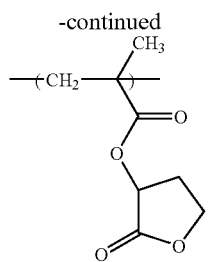

Resin Synthesis Example 2

Monomers used in this Resin Synthesis Example are following monomers M1 and M4.

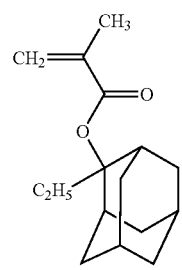

M1

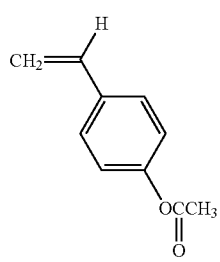

M4

96.9 Parts of the monomer M1, 147.6 parts of the monomer M4 and 331 parts of methyl isobutyl ketone were mixed and the resultant mixture was heated to 80° C. To the mixture, a solution obtained by mixing 13.5 parts of dimethyl-2,2'-azo-bis(2-methylpropionate) with 36.0 parts of methyl isobutyl ketone was added dropwise over 10 minutes. The resultant mixture was heated at 80° C. for 15 hours. The reaction mixture was poured into a mixed solution of 5000 parts of methanol and 625 parts of water, and the precipitate was obtained by filtration. The precipitate was mixed with 489 parts of methanol and 25.4 parts of 4-dimethylaminopyridine was added thereto. The resultant mixture was heated at 62° C. for 15 hours. 37.5 parts of glacial acetic acid was added to the mixture to stir for 30 minutes. The mixture obtained was poured into large amount of water to cause precipitation. The precipitate was isolated by filtration, washed with water and dried under reduced pressure condition. As a result, copolymer having a weight-average molecular weight of about 8,200 and Mw (weight-average molecular weight)/Mn (number-average molecular weight) of 1.68 was obtained. This copolymer had the following structural units represented by the formulae (1) and (m). It was confirmed that the content of the structural unit represented by the formula (1) was 30% and the content of the structural unit represented by the formula (m) was 70% by $^{13}$C-NMR analysis. This is called as resin R2.

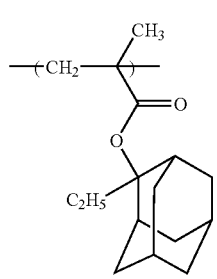

(l)

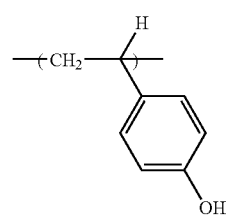

(m)

Resin Synthesis Example 3

According to the same manner as that described in Resin Synthesis Example 2, the copolymer having the structural units represented by the above-mentioned formulae (l) and (m) was obtained except that 64.6 parts of the monomer M1 was used in place of 96.9 parts of the monomer M1 and 168.7 parts of the monomer M4 was used in place of 147.6 parts of the monomer M4. The copolymer obtained had a weight-average molecular weight of about 8,600 and Mw (weight-average molecular weight)/Mn (number-average molecular weight) of 1.65. It was confirmed that the content of the structural unit represented by the above-mentioned formula (l) was 20% and the content of the structural unit represented by the above-mentioned formula (m) was 80% by $^{13}$C-NMR analysis. This is called as resin R3.

Example 1 and Comparative Example 1

<Resin>

Resin R1

<Acid generator>

Acid generator B1:

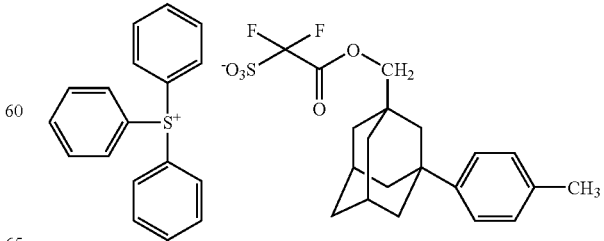

Acid generator C1:

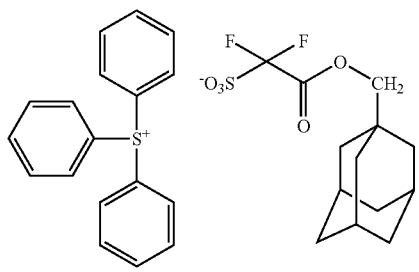

<Quencher>

Quencher Q1: 2,6-diisopropylaniline

<Solvent>

| Solvent Y1: | propylene glycol monomethyl ether acetate | 51.5 parts |
| | 2-heptanone | 35.0 parts |
| | γ-butyrolactone | 3.5 parts |

The following components were mixed to give a solution, and the solution was further filtrated through a fluorine resin filter having a pore diameter of 0.2 μm, to prepare resist liquid.

Resin (kind and amount are described in Table 1)
Acid generator (kind and amount are described in Table 1)
Quencher (kind and amount are described in Table 1)
Solvent (kind and amount are described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 1 | R1/10 | B1/0.30 | Q1/0.0325 | Y1 |
| Comp. Ex. 1 | R1/10 | C1/0.26 | Q1/0.0325 | Y1 |

Silicon wafers were each coated with "ARC-29A-8", which is an organic anti-reflective coating composition available from Nissan Chemical Industries, Ltd., and then baked under the conditions of 205° C. and 60 seconds, to form a 780 Å-thick organic anti-reflective coating. Each of the resist liquids prepared as above was spin-coated over the anti-reflective coating so that the thickness of the resulting film became 0.25 μm after drying. After application of each of the resist liquids, the silicon wafers thus coated with the respective resist liquids were each prebaked on a direct hotplate at a temperature of 125° C. for 60 seconds. Using an ArF excimer stepper ("NSR ArF" manufactured by Nikon Corporation, NA=0.55, 2/3 Annular), each wafer on which the respective resist film had been thus formed was exposed to a line and space pattern, while changing stepwise the exposure quantity.

After the exposure, each wafer was subjected to post-exposure baking on a hotplate at a temperature of 125° C. for 60 seconds and then to paddle development for 60 seconds with an aqueous solution of 2.38% tetramethylammonium hydroxide.

Each of a dark field pattern developed on the organic anti-reflective coating substrate after the development was observed with a scanning electron microscope, and the results of which are shown in Table 2. The term "dark field pattern", as used herein, means a pattern obtained by exposure and development through a reticle comprising an outer frame made of a chromium layer (light-shielding layer) and linear glass surfaces (light-transmitting portions) formed on chromium layers (light-shielding layers) extending inside the outer frame. Thus, the dark field pattern is such that, after exposure and development, resist layer surrounding the line and space pattern is left.

Resolution: It is expressed as the minimum size of space pattern which gave the space pattern split by the line pattern at the exposure amount of the effective sensitivity. The smaller the value is, the higher the Resolution is. Herein, effective sensitivity is expressed as the amount of exposure that the line pattern (light-shielding layer) and the space pattern (light-transmitting portion) become 1:1 after exposure through 0.13 μm line and space pattern mask and development.

TABLE 2

| Ex. No. | Resolution (μm) |
|---|---|
| Ex. 1 | 0.12 |
| Comp. Ex. 1 | 0.13 |

Examples 2 to 3 and Comparative Examples 2 to 3

<Resin>

Resin R1

<Acid generator>

Acid generator B2:

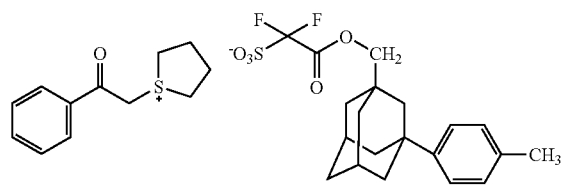

Acid generator B3:

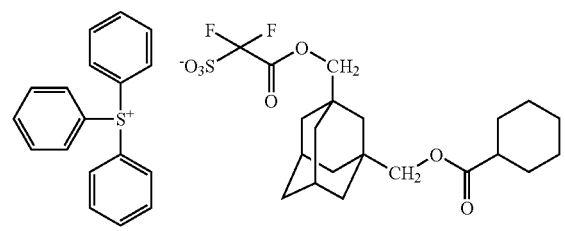

Acid generator C1:

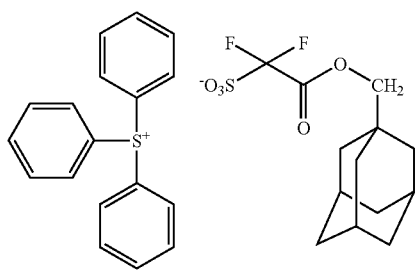

Acid generator C3:

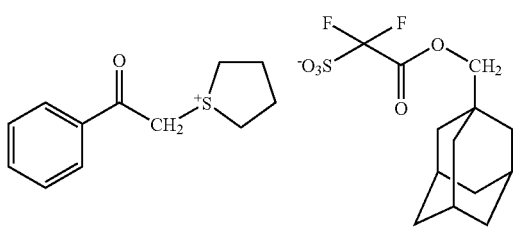

<Quencher>

Quencher Q1: 2,6-diisopropylaniline

<Solvent>

| Solvent Y1: | propylene glycol monomethyl ether acetate | 51.5 parts |
|---|---|---|
| | 2-heptanone | 35.0 parts |
| | γ-butyrolactone | 3.5 parts |

The following components were mixed to give a solution, and the solution was further filtrated through a fluorine resin filter having a pore diameter of 0.2 μm, to prepare resist liquid.

Resin (kind and amount are described in Table 3)
Acid generator (kind and amount are described in Table 3)
Quencher (kind and amount are described in Table 3)
Solvent (kind and amount are described in Table 3)

TABLE 3

| Ex. No. | Resin (kind/ amount (part)) | Acid generator (kind/ amount (part)) | Quencher (kind/ amount (part)) | Solvent | PB (° C.) | PEB (° C.) |
|---|---|---|---|---|---|---|
| Ex. 2 | R1/10 | B2/0.46 | Q1/0.007 | Y1 | 100 | 110 |
| Comp. Ex. 2 | R1/10 | C3/0.39 | Q1/0.007 | Y1 | 100 | 115 |
| Ex. 3 | R1/10 | B3/0.32 | Q1/0.0325 | Y1 | 120 | 120 |
| Comp. Ex. 3 | R1/10 | C1/0.26 | Q1/0.0325 | Y1 | 120 | 120 |

Silicon wafers were each coated with "ARC-29A-8", which is an organic anti-reflective coating composition available from Nissan Chemical Industries, Ltd., and then baked under the conditions of 205° C. and 60 seconds, to form a 780 Å-thick organic anti-reflective coating. Each of the resist liquids prepared as above was spin-coated over the anti-reflective coating so that the thickness of the resulting film became 0.15 μm after drying. After application of each of the resist liquids, the silicon wafers thus coated with the respective resist liquids were each prebaked on a proximity hotplate at a temperature shown in column of "PB" of Table 3 for 60 seconds. Using an ArF excimer stepper ("FPA-5000AS3" manufactured by CANON INC., NA=0.75, 2/3 Annular), each wafer on which the respective resist film had been thus formed was exposed to a line and space pattern, while changing stepwise the exposure quantity.

After the exposure, each wafer was subjected to post-exposure baking on a hotplate at a temperature shown in column of "PEB" of Table 3 for 60 seconds and then to paddle development for 15 seconds with an aqueous solution of 2.38% tetramethylammonium hydroxide.

Each of a line and space pattern developed on the organic anti-reflective coating substrate after the development was observed with a scanning electron microscope, and the results of which are shown in Table 4.

Effective Sensitivity (ES): It is expressed as the amount of exposure that the width of line of 100 nm line and space pattern became just 100 nm.

Resolution: It is expressed as the minimum size of space pattern which gave the space pattern split by the line pattern at the exposure amount of the effective sensitivity. The smaller the value is, the higher the Resolution is.

TABLE 4

| Ex. No. | Resolution (μm) |
|---|---|
| Ex. 2 | 0.090 |
| Comp. Ex. 2 | 0.095 |
| Ex. 3 | 0.090 |
| Comp. Ex. 3 | 0.105 |

Example 4 and Comparative Example 4

<Resin>

Resin R2

Resin R3

<Acid generator>

Acid generator B1:

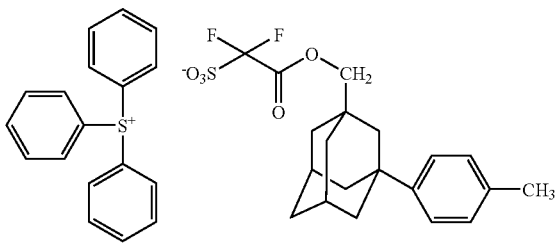

Acid generator C1:

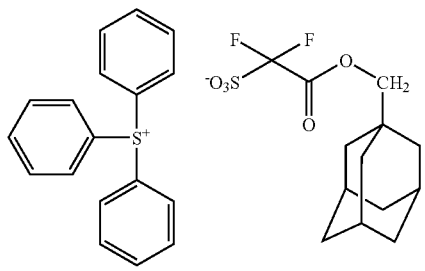

<Quencher>

Quencher Q1: 2,6-diisopropylaniline

<Solvent>

Solvent Y2: propylene glycol monomethyl ether acetate 74.1 parts

The following components were mixed to give a solution, and the solution was further filtrated through a fluorine resin filter having a pore diameter of 0.2 μm, to prepare resist liquid.

Resin (kind and amount are described in Table 5)
Acid generator (kind and amount are described in Table 5)
Quencher (kind and amount are described in Table 5)
Solvent (kind and amount are described in Table 5)

TABLE 5

| Ex. No. | Resin (kind/amount (part)) | Acid generator (kind/amount (part)) | Quencher (kind/amount (part)) | Solvent |
|---|---|---|---|---|
| Ex. 4 | R2/6 R3/4 | B1/0.33 | Q1/0.0222 | Y2 |
| Comp. Ex. 4 | R2/6 R3/4 | C1/0.33 | Q1/0.0222 | Y2 |

Silicon wafers were each coated with "DUV-42P", which is an organic anti-reflective coating composition available from Nissan Chemical Industries, Ltd., and then baked under the conditions of 205° C. and 60 seconds, to form a 600 Å-thick organic anti-reflective coating. Each of the resist liquids prepared as above was spin-coated over the anti-reflective coating so that the thickness of the resulting film became 0.42 μm after drying. After application of each of the resist liquids, the silicon wafers thus coated with the respective resist liquids were each prebaked on a direct hotplate at a temperature of 110° C. for 60 seconds. Using an KrF excimer stepper ("NSR-2205EX12B" manufactured by Nikon Corporation, NA=0.55, 2/3 Annular), each wafer on which the respective resist film had been thus formed was exposed to a line and space pattern, while changing stepwise the exposure quantity.

After the exposure, each wafer was subjected to post-exposure baking on a hotplate at a temperature of 110° C. for 60 seconds and then to paddle development for 60 seconds with an aqueous solution of 2.38% tetramethylammonium hydroxide.

Each of a dark field pattern developed on the organic anti-reflective coating substrate after the development was observed with a scanning electron microscope, and the results of which are shown in Table 6. The term "dark field pattern", as used herein, means a pattern obtained by exposure and development through a reticle comprising an outer frame made of a chromium layer (light-shielding layer) and linear glass surfaces (light-transmitting portions) formed on chromium layers (light-shielding layers) extending inside the outer frame. Thus, the dark field pattern is such that, after exposure and development, resist layer surrounding the line and space pattern is left.

Resolution: It is expressed as the minimum size of space pattern which gave the space pattern split by the line pattern at the exposure amount of the effective sensitivity. The smaller the value is, the higher the Resolution is. Herein, effective sensitivity is expressed as the amount of exposure that the line pattern (light-shielding layer) and the space pattern (light-transmitting portion) become 1:1 after exposure through 0.20 μm line and space pattern mask and development.

TABLE 6

| Ex. No. | Resolution (μm) |
|---|---|
| Ex. 4 | 0.15 |
| Comp. Ex. 4 | 0.16 |

The salt represented by the formula (1) is suitably used for an acid generator capable of providing chemically amplified positive resist compositions giving patterns having higher resolution, and the present resist composition is especially suitable for ArF excimer laser lithography, KrF excimer laser lithography and ArF immersion lithography.

What is claimed is:

1. A salt represented by the formula (I):

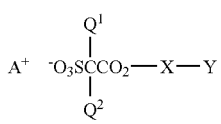

(I)

wherein

X represents a C3-C30 divalent group containing at least one divalent alicyclic hydrocarbon group, and at least one —CH$_2$— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be replaced with —O— or —CO—, Q$^1$ and Q$^2$ each independently represent a fluorine atom or a C1-C6 perfluoroalkyl group, and A$^+$ represents an organic counter ion.

2. The salt according to claim 1, wherein Q$^1$ and Q$^2$ each independently represent a fluorine atom or a trifluoromethyl group.

3. The salt according to claim 1, wherein the organic counter ion is at least one cation selected from a cation represented by the formula (IIa):

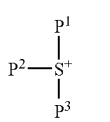

(IIa)

wherein P$^1$, P$^2$ and P$^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

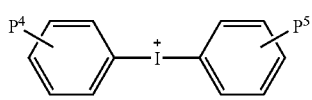
(IIb)

wherein $P^4$ and $P^5$ each independently represent a hydrogen atom, a hydroxyl group, a C1-C12 alkyl group or a C1-C12 alkoxy group, a cation represented by the formula (IIc):

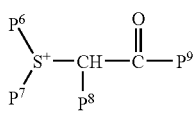
(IIc)

wherein $P^6$ and $P^7$ each independently represent a C1-C12 alkyl group or a C3-C12 cycloalkyl group, or $P^6$ and $P^7$ are bonded together to form a C3-C12 divalent acyclic hydrocarbon group which forms a ring with the adjacent $S^+$, and at least one —$CH_2$— in the divalent acyclic hydrocarbon group may be replaced with —CO—, —O— or —S—, $P^8$ represents a hydrogen atom, $P^9$ represents a C1-C12 alkyl group, a C3-C12 cycloalkyl group or an aromatic group which may be substituted, or $P^8$ and $P^9$ are bonded together to form a divalent acyclic hydrocarbon group which forms a 2-oxocycloalkyl group with the adjacent —CHCO—, and at least one —$CH_2$— in the divalent acyclic hydrocarbon group may be replaced with —CO—, —O— or —S—, and a cation represented by the formula (IId):

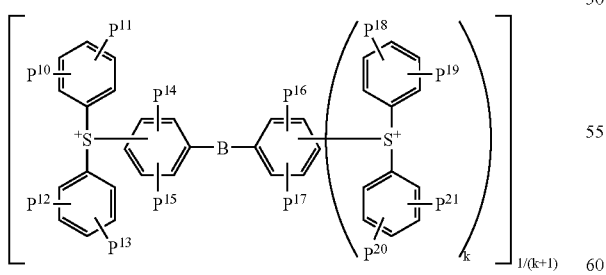
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, B represents a sulfur or oxygen atom and k represents 0 or 1.

4. The salt according to claim 1, wherein the organic counter ion is a cation represented by the formula (IIIa), (IIIb) or (IIIc):

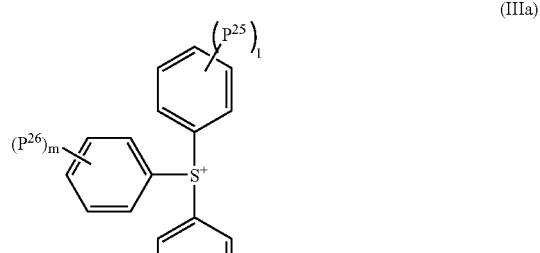
(IIIa)

(IIIb)

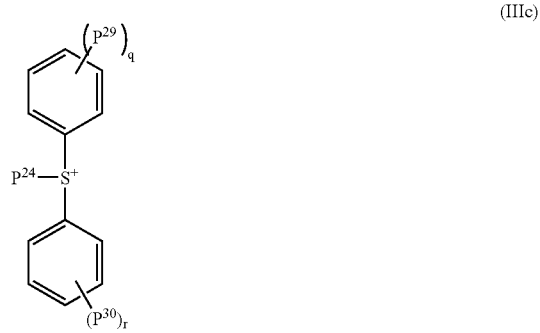
(IIIc)

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be replaced with a hydroxyl group, a C1-C12 alkoxy group or a C3-C12 cyclic hydrocarbon group and wherein at least one hydrogen atom in the C3-C30 cyclic hydrocarbon group may be replaced with a hydroxyl group a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1-C12 alkoxy group or a C3-C12 cyclic hydrocarbon group, and l, m, n, p, q and r each independently represent an integer of 0 to 5.

5. The salt according to claim 1, wherein the organic counter ion is a cation represented by the formula (IIId) or (IIIe):

(IIId)

(IIIe)

wherein P³¹ represents an aromatic group which may be substituted, P³² and P³³ are bonded together to form a C3-C12 divalent acyclic hydrocarbon group which forms a ring with the adjacent S⁺, and at least one —CH₂— in the divalent acyclic hydrocarbon group may be replaced with —CO—, —O— or —S—, and P³⁴ represents a C1-C12 alkyl group.

6. The salt according to claim 1, wherein the C3-C30 divalent alicyclic hydrocarbon group contains a cyclopentane, cyclohexane, adamantane or norbornane ring which may be substituted with at least one selected from a C1-C6 alkyl group, a C1-C6 alkoxy group, a C1-C4 perfluoroalkyl group, a C1-C6 hydroxyalkyl group, a hydroxyl group and a cyano group and at least one —CH₂— in the divalent alicyclic hydrocarbon group may be replaced with —CO— or —O—.

7. The salt according to claim 1, wherein the C3-C30 cyclic hydrocarbon group contains at least one selected from a cyclopentane, cyclohexane, benzene, naphthalene, anthrathene, phenanthrene and fluorene rings which may be substituted with at least one selected from a C1-C6 alkyl group, a C1-C6 alkoxy group, a C1-C4 perfluoroalkyl group, a C1-C6 hydroxyalkyl group, a hydroxyl group and a cyano group and at least one —CH₂— in the cyclic hydrocarbon group may be replaced with —CO— or —O—.

8. The salt according to claim 1, wherein the salt represented by the formula (I) is one represented by the formula (IVa), (IVb) or (IVc);

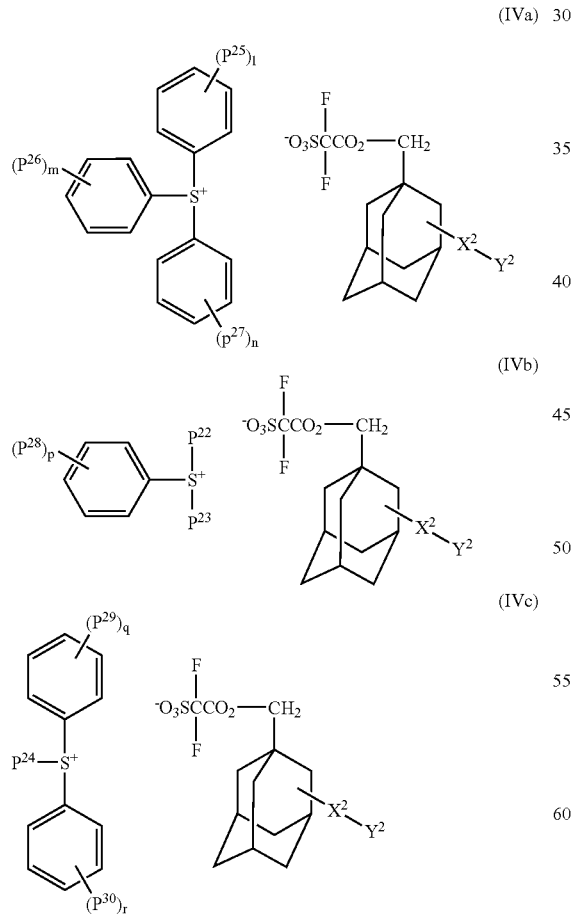

wherein P²², P²³, P²⁴, P²⁵, P²⁶, P²⁷, P²⁸, P²⁹, P³⁰, l, m, n, p, q and r are the same as defined in claim 4, and Y² represents a cyclopentyl, cyclohexyl, phenyl, naphthyl, anthryl, phenanthryl or fluorenyl group which may be substituted with at least one group selected from a C1-C6 alkyl group, a C1-C6 alkoxy group, a C1-C4 perfluoroalkyl group, a C1-C6 hydroxyalkyl group, a hydroxyl group and a cyano group, and X² represents a single bond or a C1-C6 divalent hydrocarbon group and at least one —CH₂— in the C1-C6 divalent hydrocarbon group may be replaced with —CO— or —O—.

9. The salt according to claim 4, wherein the salt is one represented by the formula (Va), (Vb), (Vc), (Vd), (Ve) or (Vf):

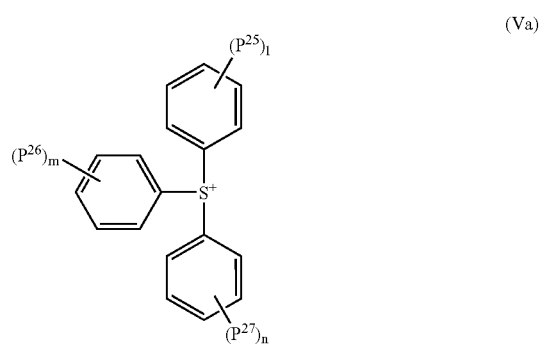

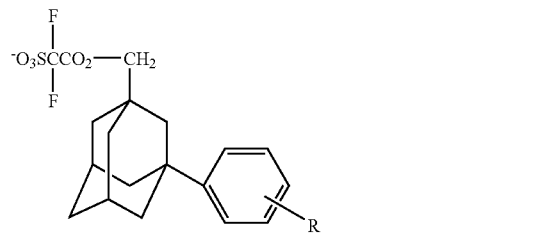

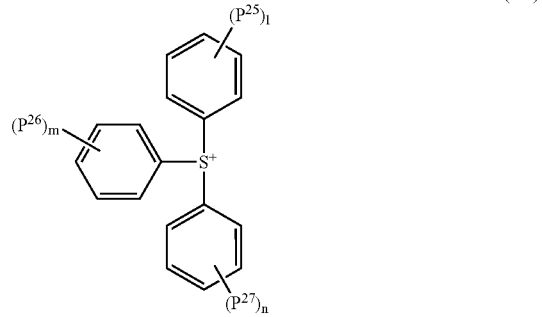

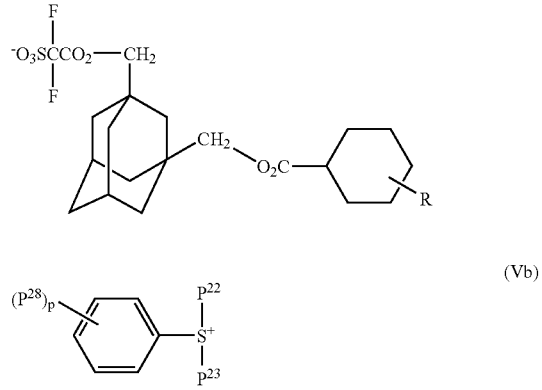

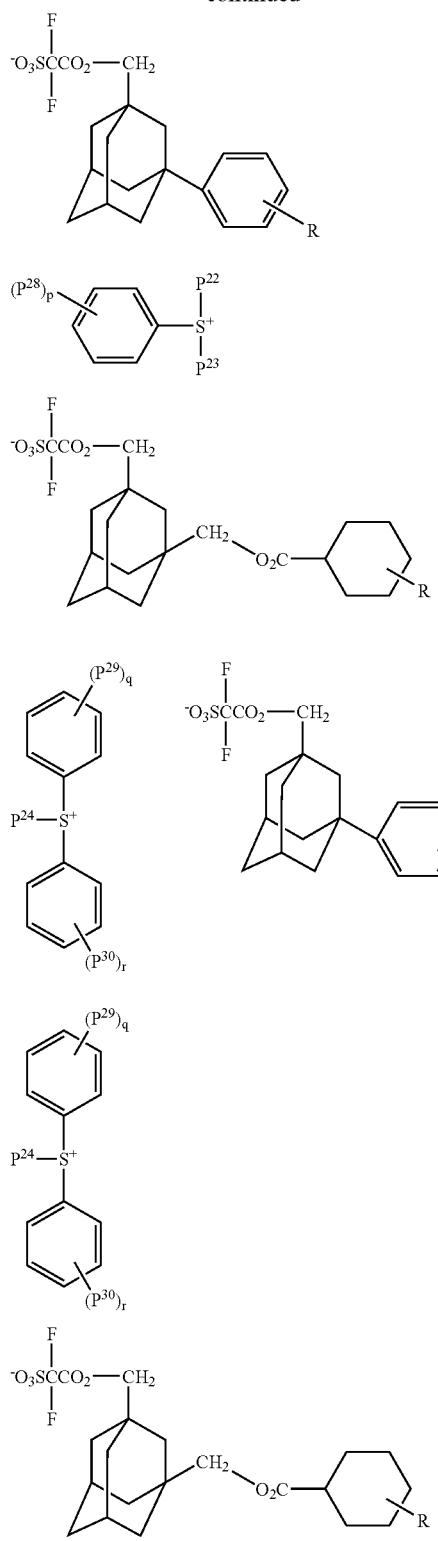

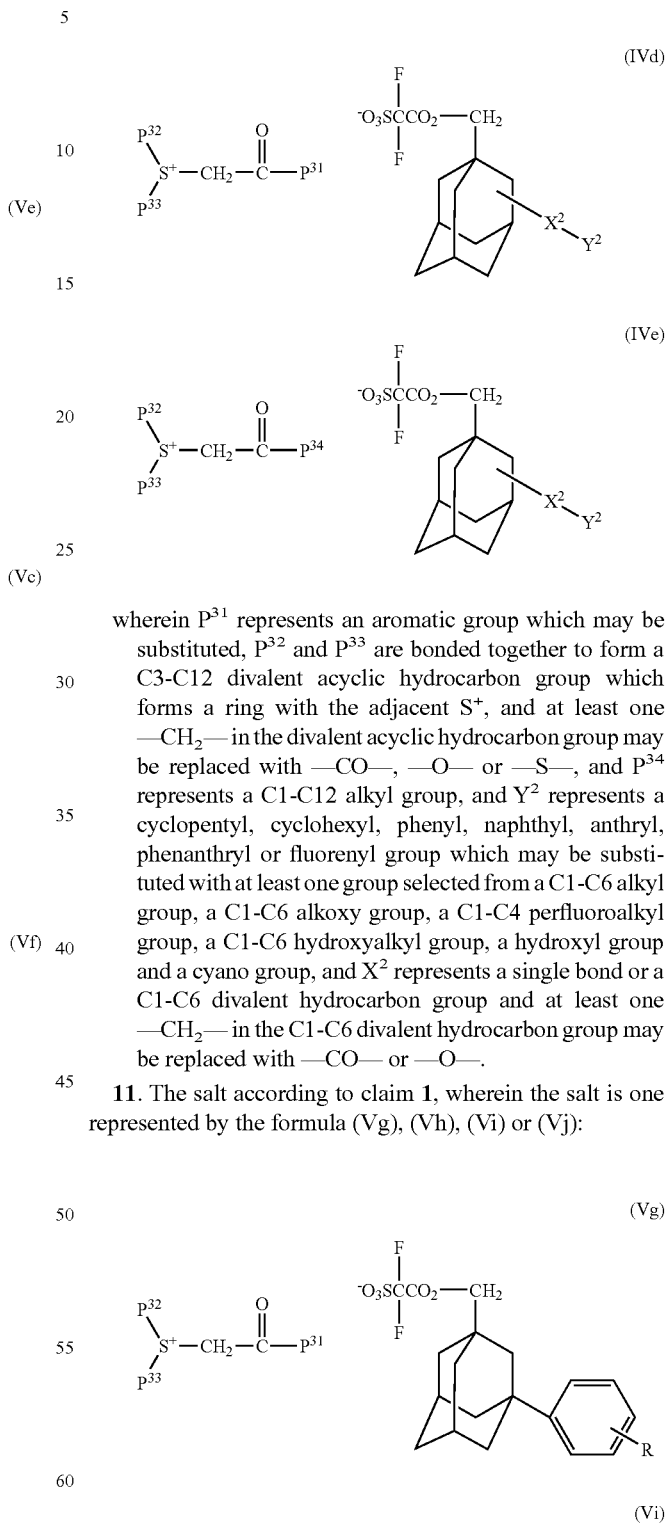

wherein $P^{22}$, $P^{23}$, $P^{24}$, $P^{25}$, $P^{26}$, $P^{27}$, $P^{28}$, $P^{29}$, $P^{30}$, l, m, n, p, q and r are the same as defined in claim 4, and R represents a hydrogen atom, a C1-C6 alkyl group, a C1-C6 alkoxy group, a C1-C4 perfluoroalkyl group, a C1-C6 hydroxyalkyl group, a hydroxyl group or a cyano group.

10. The salt according to claim 1, wherein the salt represented by the formula (I) is one represented by the formula (IVd) or (IVe);

wherein $P^{31}$ represents an aromatic group which may be substituted, $P^{32}$ and $P^{33}$ are bonded together to form a C3-C12 divalent acyclic hydrocarbon group which forms a ring with the adjacent $S^+$, and at least one —CH$_2$— in the divalent acyclic hydrocarbon group may be replaced with —CO—, —O— or —S—, and $P^{34}$ represents a C1-C12 alkyl group, and $Y^2$ represents a cyclopentyl, cyclohexyl, phenyl, naphthyl, anthryl, phenanthryl or fluorenyl group which may be substituted with at least one group selected from a C1-C6 alkyl group, a C1-C6 alkoxy group, a C1-C4 perfluoroalkyl group, a C1-C6 hydroxyalkyl group, a hydroxyl group and a cyano group, and $X^2$ represents a single bond or a C1-C6 divalent hydrocarbon group and at least one —CH$_2$— in the C1-C6 divalent hydrocarbon group may be replaced with —CO— or —O—.

11. The salt according to claim 1, wherein the salt is one represented by the formula (Vg), (Vh), (Vi) or (Vj):

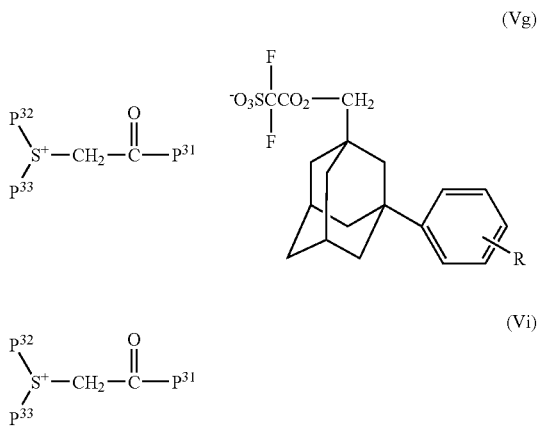

-continued

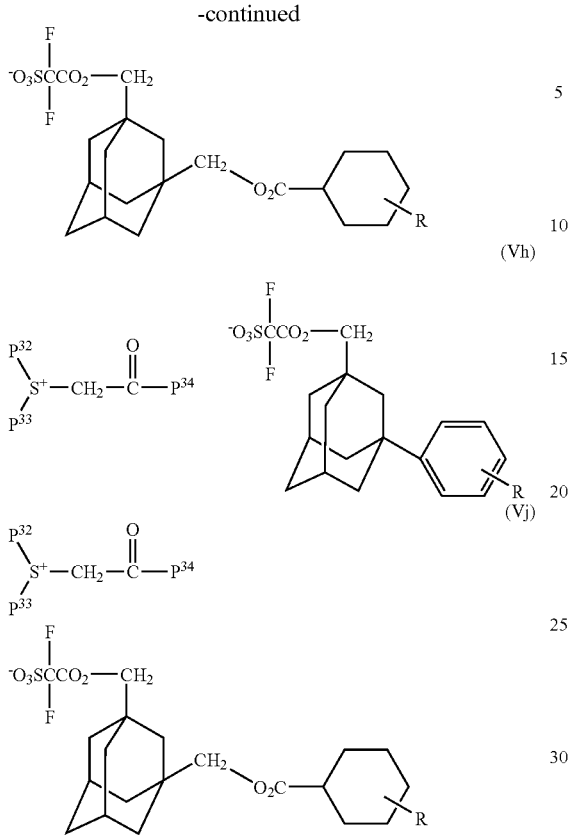

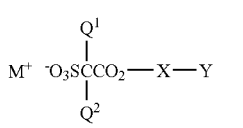

wherein P³¹ represents an aromatic group which may be substituted, P³² and P³³ are bonded together to form a C3-C12 divalent acyclic hydrocarbon group which forms a ring with the adjacent S⁺, and at least one —CH₂— in the divalent acyclic hydrocarbon group may be replaced with —CO—, —O— or —S—, and P³⁴ represents a C1-C12 alkyl group, and R represents a hydrogen atom, a C1-C6 alkyl group, a C1-C6 alkoxy group, a C1-C4 perfluoroalkyl group, a C1-C6 hydroxyalkyl group, a hydroxyl group or a cyano group.

12. A salt represented by the formula (VI):

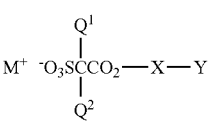

wherein

X represents a C3-C30 divalent group containing at least one divalent alicyclic hydrocarbon group, and at least one —CH₂— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH₂— in the C3-C30 cyclic hydrocarbon group may be replaced with —O— or —CO—, Q¹ and Q² each independently represent a fluorine atom or a C1-C6 perfluoroalkyl group, and M⁺ represents Li, Na, K or Ag.

13. A process for production of a salt represented by the formula (VI):

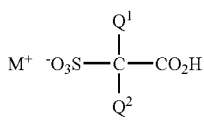

wherein

X represents a C3-C30 divalent group containing at least one divalent alicyclic hydrocarbon group, and at least one —CH₂— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH₂— in the C3-C30 cyclic hydrocarbon group may be replaced with —O— or —CO—, Q¹ and Q² each independently represent a fluorine atom or a C1-C6 perfluoroalkyl group, and M⁺ represents Li, Na, K or Ag, which comprises reacting a compound represented by the formula (IX):

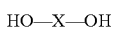

wherein Q¹, Q² and M⁺ are the same as defined above, with a compound represented by the formula (VII):

wherein X is the same as defined above, and a compound represented by the formula (VIII):

H—Y                    (VIII)

wherein Y is the same as defined above.

14. A process for production of a salt represented by the formula (VI):

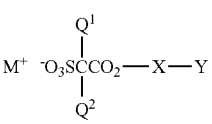

wherein

X represents a C3-C30 divalent group containing at least one divalent alicyclic hydrocarbon group, and at least one —CH₂— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be replaced with —O— or —CO—, Q$^1$ and Q$^2$ each independently represent a fluorine atom or a C1-C6 perfluoroalkyl group, and M$^+$ represents Li, Na, K or Ag, which comprises reacting a compound represented by the formula (IX):

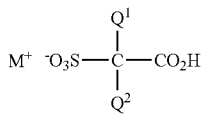

(IX)

wherein Q$^1$, Q$^2$ and M$^+$ are the same as defined above, with a compound represented by the formula (X):

HO—X—Y  (X)

wherein X and Y are the same as defined above.

15. A process for production of a salt represented by the formula (I):

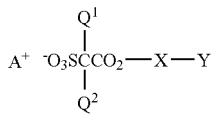

(I)

wherein

X represents a C3-C30 divalent group containing at least one divalent alicyclic hydrocarbon group, and at least one —CH$_2$— in the C3C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be replaced with —O— or —CO—, Q$^1$ and Q$^2$ each independently represent a fluorine atom or a C1-C6 perfluoroalkyl group, and A$^+$ represents an organic counter ion, which comprises reacting a salt represented by the formula (VI):

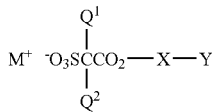

(VI)

wherein X and Y are the same as defined above and M$^+$ represents Li, Na, K or Ag, with a compound represented by the formula (XI):

A$^+$Z$^-$  (XI)

wherein A$^+$ is the same as defined above and Z represents F, Cl, Br, I, BF$_4$, AsF$_6$, SbF$_6$, PF$_6$ or ClO$_4$.

16. A process for production of a salt represented by the formula (I):

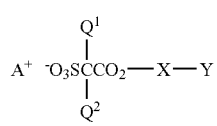

(I)

wherein

X represents a C3-C30 divalent group containing at least one divalent alicyclic hydrocarbon group, and at least one —CH$_2$— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be replaced with —O— or —CO—, Q$^1$ and Q$^2$ each independently represent a fluorine atom or a C1-C6 perfluoroalkyl group, and A$^+$ represents an organic counter ion, which comprises reacting a salt represented by the formula (XII):

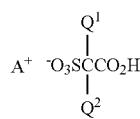

(XII)

wherein Q$^1$, Q$^2$ and A$^+$ are the same as defined above, with a compound represented by the formula (VII):

HO—X—OH  (VII)

wherein X is the same as the defined above, and a compound represented by the formula (VIII):

H—Y  (VIII)

wherein Y is the same as defined above.

17. A process for production of a salt represented by the formula (I):

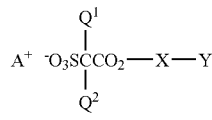

(I)

wherein

X represents a C3-C30 divalent group containing at least one divalent alicyclic hydrocarbon group, and at least one —CH$_2$— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —CH$_2$— in the C3-C30 cyclic hydrocarbon group may be replaced with —O— or —CO—, Q$^1$ and Q$^2$ each independently represent a fluorine atom or a C1-C6 perfluoroalkyl group, and A$^+$ represents an organic counter ion, which comprises reacting a salt represented by the formula (XIII):

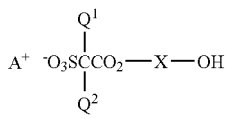
(XIII)

wherein $Q^1$, $Q^2$, $A^+$ and X are the same as defined above, with a compound represented by the formula (VIII):

H—Y (VIII)

wherein Y is the same as defined above.

18. A chemically amplified positive resist composition comprising a salt represented by the formula (I):

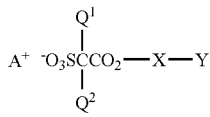
(I)

wherein

X represents a C3-C30 divalent group containing at least one divalent alicyclic hydrocarbon group, and at least one —$CH_2$— in the C3-C30 divalent group may be replaced with —O— or —CO—, Y represents a C3-C30 cyclic hydrocarbon group which may be substituted with at least one group selected from a C1-C6 alkoxy group, a C1-C4 perfluoroalkyl group, a C1-C6 hydroxyalkyl group, a hydroxyl group and a cyano group, and at least one —$CH_2$— in the C3-C30 cyclic hydrocarbon group may be replaced with —O— or —CO—, $Q^1$ and $Q^2$ each independently represent a fluorine atom or a C1-C6 perfluoroalkyl group, and $A^+$ represents an organic counter ion, and a resin which contains a structural unit which has an acid-labile group and which itself is insoluble or poorly soluble in an aqueous alkali solution but becomes soluble in an aqueous alkali solution by the action of an acid.

19. The chemically amplified positive resist composition according to claim 18, wherein $Q^1$ and $Q^2$ each independently represent a fluorine atom or a trifluoromethyl group.

20. The chemically amplified positive resist composition according to claim 18, wherein the organic counter ion is at least one cation selected from a cation represented by the formula (IIa):

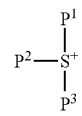
(IIa)

wherein $P^1$, $P^2$ and $P^3$ each independently represent a C1-C30 alkyl group which may be substituted with at least one selected from a hydroxyl group, a C3-C12 cyclic hydrocarbon group and a C1-C12 alkoxy group, or a C3-C30 cyclic hydrocarbon group which may be substituted with at least one selected from a hydroxyl group and a C1-C12 alkoxy group, a cation represented by the formula (IIb):

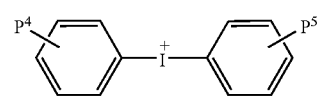
(IIb)

wherein $P^4$ and $P^5$ each independently represent a hydrogen atom, a hydroxyl group, a C1-C12 alkyl group or a C1-C12 alkoxy group, a cation represented by the formula (IIc):

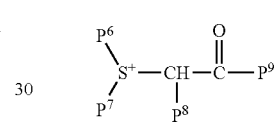
(IIc)

wherein $P^6$ and $P^7$ each independently represent a C1-C12 alkyl group or a C3-C12 cycloalkyl group, or $P^6$ and $P^7$ are bonded together to form a C3-C12 divalent acyclic hydrocarbon group which forms a ring with the adjacent $S^+$, and at least one —$CH_2$— in the divalent acyclic hydrocarbon group may be replaced with —CO—, —O— or —S—, $P^8$ represents a hydrogen atom, $P^9$ represents a C1-C12 alkyl group, a C3-C12 cycloalkyl group or an aromatic group which may substituted, or $P^8$ and $P^9$ are bonded together to form a divalent acyclic hydrocarbon group which forms a 2-oxocycloalkyl group with the adjacent —CHCO—, and at least one —$CH_2$— in the divalent acyclic hydrocarbon group may be replaced with —CO—, —O— or —S—, and a cation represented by the formula (IId):

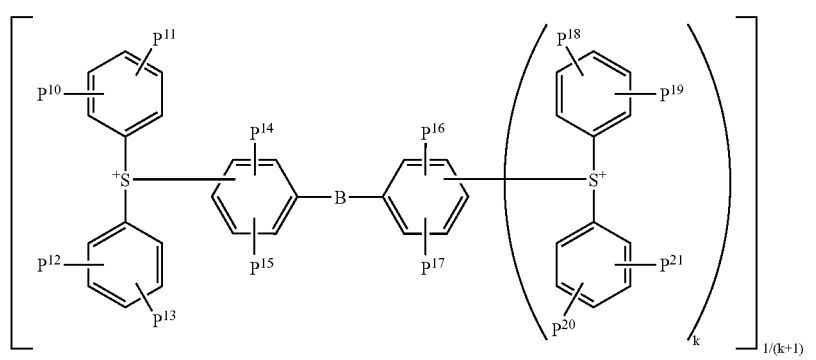
(IId)

wherein $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1C12 alkoxy group, B represents a sulfur or oxygen atom and k represents 0 or 1.

21. The chemically amplified positive resist composition according to claim 18, wherein the organic counter ion is a cation represented by the formula (IIIa), (IIIb) or (IIIc):

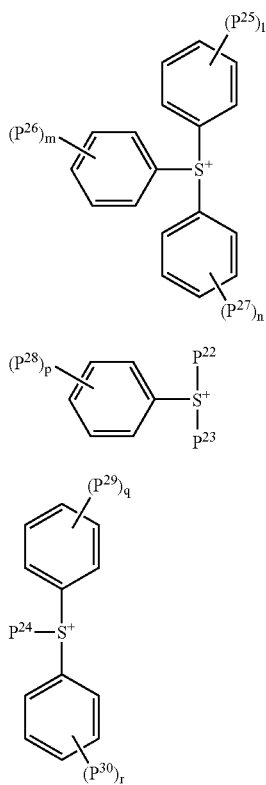

wherein $P^{22}$, $P^{23}$ and $P^{24}$ each independently represent a C1-C20 alkyl group or a C3-C30 cyclic hydrocarbon group except a phenyl group, wherein at least one hydrogen atom in the C1-C20 alkyl group may be replaced with a hydroxyl group, a C1-12 alkoxy group or a C3-C12 cyclic hydrocarbon group and wherein at least one hydrogen atom in the C3-C30 cyclic hydrocarbon group may be replaced with a hydroxyl group, a C1-C12 alkyl group or a C1-C12 alkoxy group; and $P^{25}$, $P^{26}$, $P^{27}$, $P^{28}$, $P^{29}$ and $P^{30}$ each independently represent a hydroxyl group, a C1-C12 alkyl group, a C1C12 alkoxy group or a C3-C12 cyclic hydrocarbon group, and l, m, n, p, q and r each independently represent an integer of 0 to 5.

22. The chemically amplified positive resist composition according to claim 18, wherein the organic counter ion is a cation represented by the formula (IIId) or (IIIe):

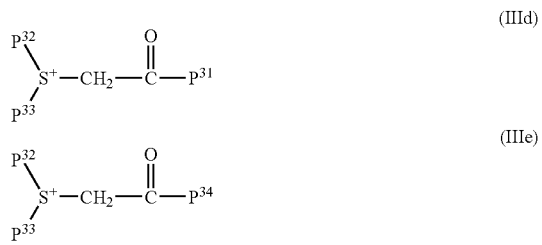

wherein $P^{31}$ represents an aromatic group which may be substituted, $P^{32}$ and $P^{33}$ are bonded together to form a C3-C12 divalent acyclic hydrocarbon group which forms a ring with the adjacent $S^+$, and at least one —$CH_2$— in the divalent acyclic hydrocarbon group may be replaced with —CO—, —O— or —S—, and $P^{34}$ represents a C1-C12 alkyl group.

23. The chemically amplified positive resist composition according to claim 18, wherein the resin contains a structural unit derived from a monomer having a bulky and acid-labile group.

24. The chemically amplified positive resist composition according to claim 18, wherein the resin contains a structural unit derived from hydroxystyrene.

25. The chemically amplified positive resist composition according to claim 24, wherein the resin contains a structural unit which is derived from hydroxystyrene and in which a part of hydroxyl groups are protected with acid-labile groups in addition to the structural unit derived from hydroxystyrene.

26. The chemically amplified positive resist composition according to claim 18, wherein the chemically amplified positive resist composition further comprises a basic compound.

* * * * *